US011608380B2

(12) United States Patent
Kirshner et al.

(10) Patent No.: US 11,608,380 B2
(45) Date of Patent: Mar. 21, 2023

(54) ANTI-EGFRVIII ANTIBODIES AND USES THEREOF

(71) Applicant: REGENERON PHARMACEUTICALS, INC., Tarrytown, NY (US)

(72) Inventors: Jessica R. Kirshner, New York, NY (US); Douglas MacDonald, New York, NY (US); Gavin Thurston, Briarcliff Manor, NY (US); Joel H. Martin, Putnam Valley, NY (US); Frank Delfino, Poughquag, NY (US); Thomas Nittoli, Pearl River, NY (US); Marcus Kelly, New York, NY (US)

(73) Assignee: REGENERON PHARMACEUTICALS, INC., Tarrytown, NY (US)

( * ) Notice: Subject to any disclaimer, the term of this patent is extended or adjusted under 35 U.S.C. 154(b) by 0 days.

(21) Appl. No.: 16/918,656

(22) Filed: Jul. 1, 2020

(65) Prior Publication Data
US 2021/0147557 A1     May 20, 2021

Related U.S. Application Data

(60) Continuation of application No. 16/033,477, filed on Jul. 12, 2018, now Pat. No. 10,738,124, which is a continuation of application No. 15/170,628, filed on Jun. 1, 2016, now Pat. No. 10,047,160, which is a division of application No. 14/643,886, filed on Mar. 10, 2015, now Pat. No. 9,475,875.

(60) Provisional application No. 61/950,963, filed on Mar. 11, 2014.

(51) Int. Cl.
| *A61K 39/00* | (2006.01) |
| *C07K 16/28* | (2006.01) |
| *A61K 39/395* | (2006.01) |
| *A61K 45/06* | (2006.01) |
| *A61K 47/68* | (2017.01) |
| *C07K 16/30* | (2006.01) |

(52) U.S. Cl.
CPC ...... *C07K 16/2863* (2013.01); *A61K 39/3955* (2013.01); *A61K 39/39558* (2013.01); *A61K 45/06* (2013.01); *A61K 47/6803* (2017.08); *A61K 47/6851* (2017.08); *C07K 16/30* (2013.01); *C07K 16/3015* (2013.01); *C07K 16/3023* (2013.01); *C07K 16/3069* (2013.01); *A61K 2039/505* (2013.01); *A61K 2039/507* (2013.01); *C07K 2317/33* (2013.01); *C07K 2317/34* (2013.01); *C07K 2317/565* (2013.01); *C07K 2317/77* (2013.01); *C07K 2317/92* (2013.01)

(58) Field of Classification Search
None
See application file for complete search history.

(56) References Cited

U.S. PATENT DOCUMENTS

| 5,208,020 | A  | 5/1993  | Chari et al. |
| 5,212,290 | A  | 5/1993  | Vogelstein et al. |
| 5,500,362 | A  | 3/1996  | Robinson et al. |
| 5,714,586 | A  | 2/1998  | Kunstmann et al. |
| 5,821,337 | A  | 10/1998 | Carter et al. |
| 6,941,229 | B1 | 9/2005  | Elleman et al. |
| 7,060,808 | B1 | 6/2006  | Goldstein et al. |
| 7,589,180 | B2 | 9/2009  | Old et al. |
| 7,705,130 | B2 | 4/2010  | Rothe et al. |
| 7,736,644 | B2 | 6/2010  | Weber et al. |
| 7,744,882 | B2 | 6/2010  | Maihle et al. |
| 7,750,116 | B1 | 7/2010  | Doronina et al. |
| 7,754,681 | B2 | 7/2010  | Feng |
| 7,767,792 | B2 | 8/2010  | Johns et al. |
| 8,795,673 | B2 | 8/2014  | Li et al. |
| 9,327,035 | B2 | 5/2016  | Fuh et al. |
| 9,475,875 | B2 | 10/2016 | Kirshner et al. |
| 10,047,160 | B2 | 8/2018  | Kirshner et al. |
| 10,738,124 | B2 | 8/2020  | Kirshner et al. |
| 2004/0248196 | A1 | 12/2004 | Adams et al. |
| 2007/0258987 | A1 | 11/2007 | Francisco et al. |
| 2008/0305497 | A1 | 12/2008 | Kosmeder et al. |
| 2009/0269343 | A1 | 10/2009 | Bigner et al. |
| 2010/0056762 | A1 | 3/2010  | Old |
| 2010/0129314 | A1 | 5/2010  | Singh et al. |

(Continued)

FOREIGN PATENT DOCUMENTS

| EP | 3126388 B1 | 5/2019 |
| WO | 2005/010151 A2 | 2/2005 |
| WO | 2005/089808 A2 | 9/2005 |

(Continued)

OTHER PUBLICATIONS

Agarwal et al. (2013)"A Pietet-Spengler Ligation for Protein Chemical Modification," Proc. Natl. Acad. Sci., 110:46-51.

(Continued)

*Primary Examiner* — Marianne P Allen
(74) *Attorney, Agent, or Firm* — FisherBroyles, LLP; Cara L. Crowley-Weber; Kajal Chowdhury

(57) ABSTRACT

The present invention provides antibodies that bind to the class Ill variant of EGFR (EGFRvIII) and methods of using the same. According to certain embodiments, the antibodies of the invention bind human EGFRvIII with high affinity. The antibodies of the invention may be fully human antibodies. The invention includes anti-EGFRvIII antibodies conjugated to a cytotoxic agent, radionuclide, or other moiety detrimental to cell growth or proliferation. The antibodies of the invention are useful for the treatment of various cancers.

11 Claims, 8 Drawing Sheets

Specification includes a Sequence Listing.

(56) References Cited

U.S. PATENT DOCUMENTS

2013/0101546 A1     4/2013    Yurkovetskiy et al.

FOREIGN PATENT DOCUMENTS

| | | |
|---|---|---|
| WO | 2006/009694 A2 | 1/2006 |
| WO | 2008/122039 A2 | 10/2008 |
| WO | 2009/067242 A2 | 5/2009 |
| WO | 2010/010324 A1 | 1/2010 |
| WO | 2010/096434 A2 | 8/2010 |
| WO | 2011/018611 A1 | 2/2011 |
| WO | 2011/130598 A1 | 10/2011 |
| WO | 2012/005982 A2 | 11/2012 |
| WO | 2012/166559 A1 | 12/2012 |
| WO | 2013/053872 A1 | 4/2013 |
| WO | 2013/053873 A1 | 4/2013 |
| WO | 2013/055990 A1 | 4/2013 |
| WO | 2013/055993 A1 | 4/2013 |
| WO | 2013/068874 A1 | 5/2013 |
| WO | 2013/085925 A1 | 6/2013 |
| WO | 2014/145090 A1 | 9/2014 |
| WO | 2015/018527 A1 | 2/2015 |

OTHER PUBLICATIONS

Batra et al. (1995) "Epidermal Growth Factor Ligand-Independent, Unregulated, Cell-Transforming Potential of a Naturally Occurring Human Mutant EGFRvIII Gene," Cell Growth and Differentiation, 6:1251-1259.

Bigner et al. (1990) "Characterization of the Epidermal Growth Factor Receptor in Human Glioma Cell Lines and Xenografts," Cancer Res, 50:8017-8022.

Carrico et al. (2007) "Introducing Genetically Encoded Aldehydes Into Proteins," Nat. Chem. Biol., 3:321-322.

Choi et al. (2013) "Systemic Administration of a Bispecific Antibody Targeting EGFRvIII Successfully Treats Intracerebral Glioma," Proc. Natl. Acad. Sci. USA, 110:270-275.

Ducry (2010) "Antibody-Drug Conjugates: Linking Cytotoxic Payloads to Monoclonal Antibodies," Bioconjugate Chem., 21:5-13.

Ekstrand et al. (1992) "Amplified and Rearranged Epidermal Growth Factor Receptor Genes in Human Glioblastomas Reveal Deletions of Sequences Encoding Portions of the N- and/or C-terminal Tails," Proc. Natl. Acad. Sci. USA, 89:4309-4313.

Frederick et al. (2000) "Diversity and Frequency of Epidermal Growth Factor Receptor Mutations in Human Glioblastomas," Cancer Res, 60:1383-1387.

Freeman (2008) "Panitumumab and Cetuximab Epitope Mapping and In Vitro Activity," J. of Clin. Oncol., vol. 26 (5S):14536 (May 20 Supplement) Abstract, 1 page.

Garcia de Palazzo et al. (1993) "Expression of Mutated Epidermal Growth Factor Receptor by Non-Small Cell Lung Carcinomas," Cancer Res, 53:3217-3220.

Gan et al. (2012) "Targeting of a Conformationally Exposed, Tumor-Specific Epitope of EGFR as a Strategy for Cancer Therapy," Cancer Res., 72:2924-2930.

Harris et al. (1992) "Epidermal Growth Factor Receptor and Other Oncogenes as Prognostic Markers," Natl. Cancer Inst. Monogr., 11:181-187.

Hofner et al. (2008) "An Engineered Selenocysteine Defines a Unique Class of Antibody Derivatives," Proc. Natl. Acad. Sci., USA 105:12451-12456.

Hollander et al. (2008) "Selection of Reaction Additives Used in the Preparation of Monomeric Antibody-Calicheamicin Conjugates," Bioconjugate Chem., 19:358-361.

Humphrey et al. (1988) "Amplification and Expression of the Epidermal Growth Factor Receptor Gene in Human Glioma Xenografts," Cancer Res., 48:2231-2238.

Humphrey et al. (1990) "Anti-Synthetic Peptide Antibody Reacting at the Fusion Junction of Deletion-Mutant Epidermal Growth Factor Receptors in Human Glioblastoma," Proc. Natl. Acad. Sci. USA, 87:4207-4211.

Jiang et al. (2011) "Growth Suppression of Human Hepatocellular Carcinoma Xenografts by a Monoclonal Antibody CH12 Directed to Epidermal Growth Factor Receptor Variant III," J. of Biol. Chem., 286(7):5913-5920.

Modjtahedi et al. (2003) "Targeting of Cells Expressing Wild-Type EGFR and Type-III Mutant EGFR (EGFRVIII) by Anti-EGFR MAB ICR62: A Two-Pronged Attack for Tumor Therapy," Int. J. Cancer, 105:273-280.

Moscatello et al. (1995) "Frequent Expression of a Mutant Epidermal growth factor receptor in multiple human tumors," Cancer Res., 55:5536-5539.

Navari, et al. (2014) "Epitope Mapping of Epidermal Growth Factor Receptor (EGFR) Monoclonal Antibody and Induction of Growth-Inhibitory Polyclonal Antibodies by Vaccination with EGFR Mimotope," Immunopharmacol Immunotoxicol, 36(5):309-315.

Nishikawa et al. (1994) "A Mutant Epidermal Growth Factor Receptor Common in Human Glioma Confers Enhanced Tumorigenicity," Proc. Natl. Acad. Sci. USA, 91:7727-7731.

Olapade-Olaopa et al. (2000) "Evidence for the Differential Expression of a Variant EGF Receptor Protein in Human Prostate Cancer," British J Cancer, 82:186-194.

Perera et al. (2005) "Treatment of Human Tumor Xenografts with Monoclonal Antibody 806 in Combination with a Prototypical Epidermal Growth Factor Receptor-Specific Antibody Generates Enhanced Antitumor Activity," Clin Cancer Res., 11(17): 6390-6399.

Perera et al. (2007) "Internalization, Intracellular Trafficking, and Biodistribution of Monoclonal Antibody 806: A Novel Anti-Epidermal Growth Factor Receptor Antibody," Neoplasia, 9(12):1099-1110.

Rabuka et al. (2012) "Site-Specific Chemical Protein Conjugation Using Genetically Encoded Aldehyde Tags," Nat. Protocols., 10:1052-1067.

Ryan et al. (2001) "Polyclonal Antibody Production Against Chito-Oligosaccharides," Food & Agriculture Immunol., 13:127-130.

Sampson et al. (2013) "EGFRvIII mCAR-Modified T-Cell Therapy Cures Mice with Established Intracerebral Glioma and Generates Host Immunity against Tumor-Antigen Loss," Clin. Cancer Res., OF1-OF13.

Sapra et al. (2013) "Monoclonal Antibody-Based Therapies in Cancer: Advances and Challenges," Pharmacol. & Therapeutics, 138:452-469.

Shaunak et al. (2006) "Site-Specific PEGylation of Native Disulfide Bonds in Therapeutic Proteins," Natl. Chem. Biol., 2:312-313.

Tinhofer et al. (2011) "Expression of Amphiregulin and EGFRvIII Affect Outcome of Patients with Squamous Cell Carcinoma of the Head and Neck Receiving Cetuximab-Docetaxel Treatment," Clin Cancer Res, 17(15)5197-5204.

Wikstrand et al. (1995) "Monoclonal Antibodies Against EGFRvIII are Tumor Specific and React with Breast and Lung Carcinomas and Malignant Gliomas," Cancer Res., 55:3140-3148.

Wikstrand et al. (1998) "The Class III Variant of the Epidermal Growth Factor Receptor (EGFRvIII): Characterization and Utilization as an Immunotherapeutic Target," J Neuro Virol, 4:148-158.

Wong et al. (1987) "Increased Expression of the Epidermal Growth Factor Receptor Gene in Malignant Gliomas is Invariably Associated with Gene Amplification," Proc. Natl. Acad. Sci. USA, 84:6899-6903.

Wong et al. (1992) "Structural Alterations of the Epidermal Growth Factor Receptor Gene in Human Gliomas," Proc. Natl. Acad. Sci. USA, 89:2965-2969.

Yamazaki et al. (1990) "A Deletion Mutation Within the Ligand Binding Domain is Responsible for Activation of Epidermal Growth Factor Receptor Gene in Human Brain Tumors," Jap. J. Cancer Res., 81:773-779.

International Search Report and Written Opinion, PCT/US2015/019722, dated May 29, 2015, 17 pages.

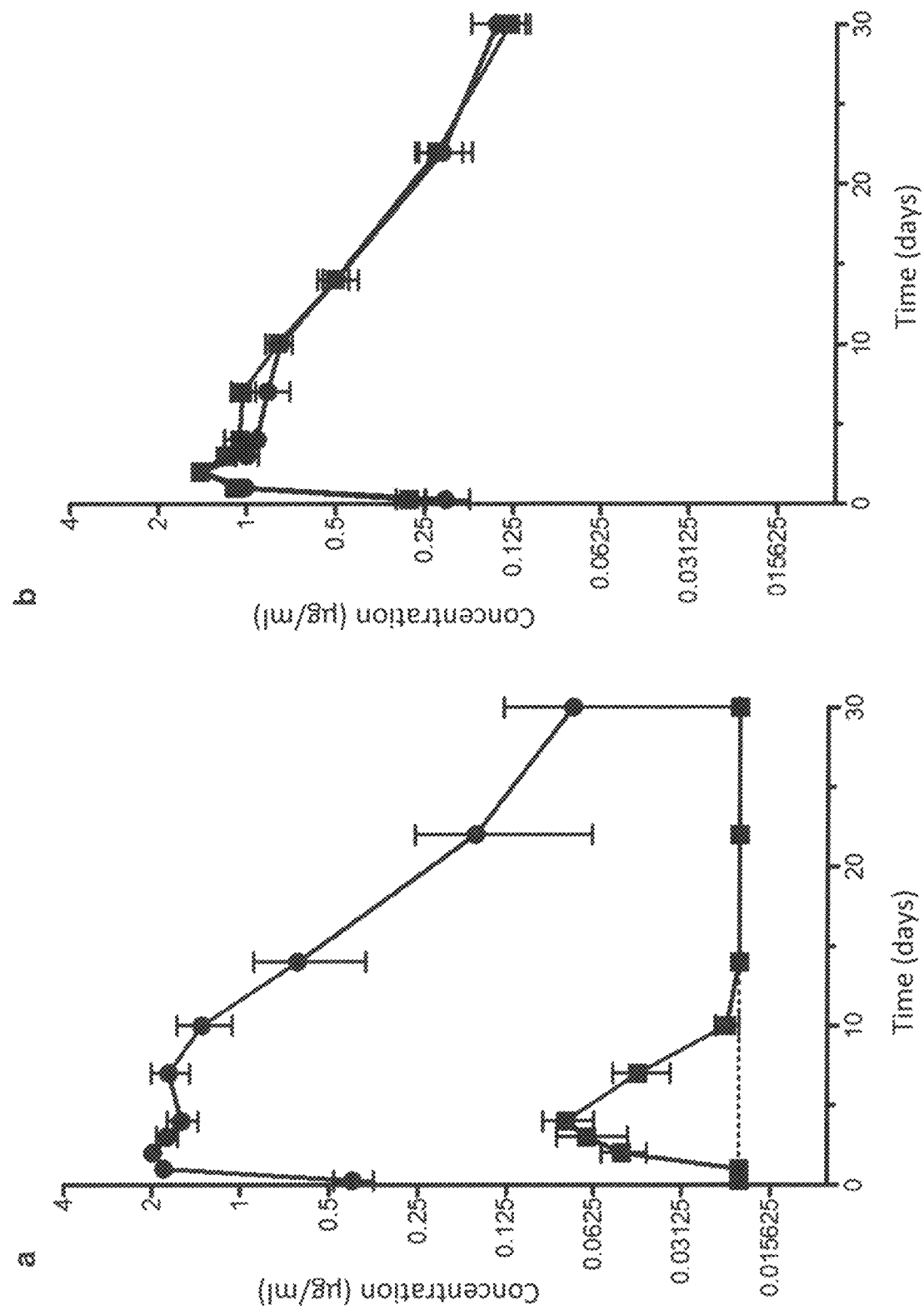
Fig. 5a-b

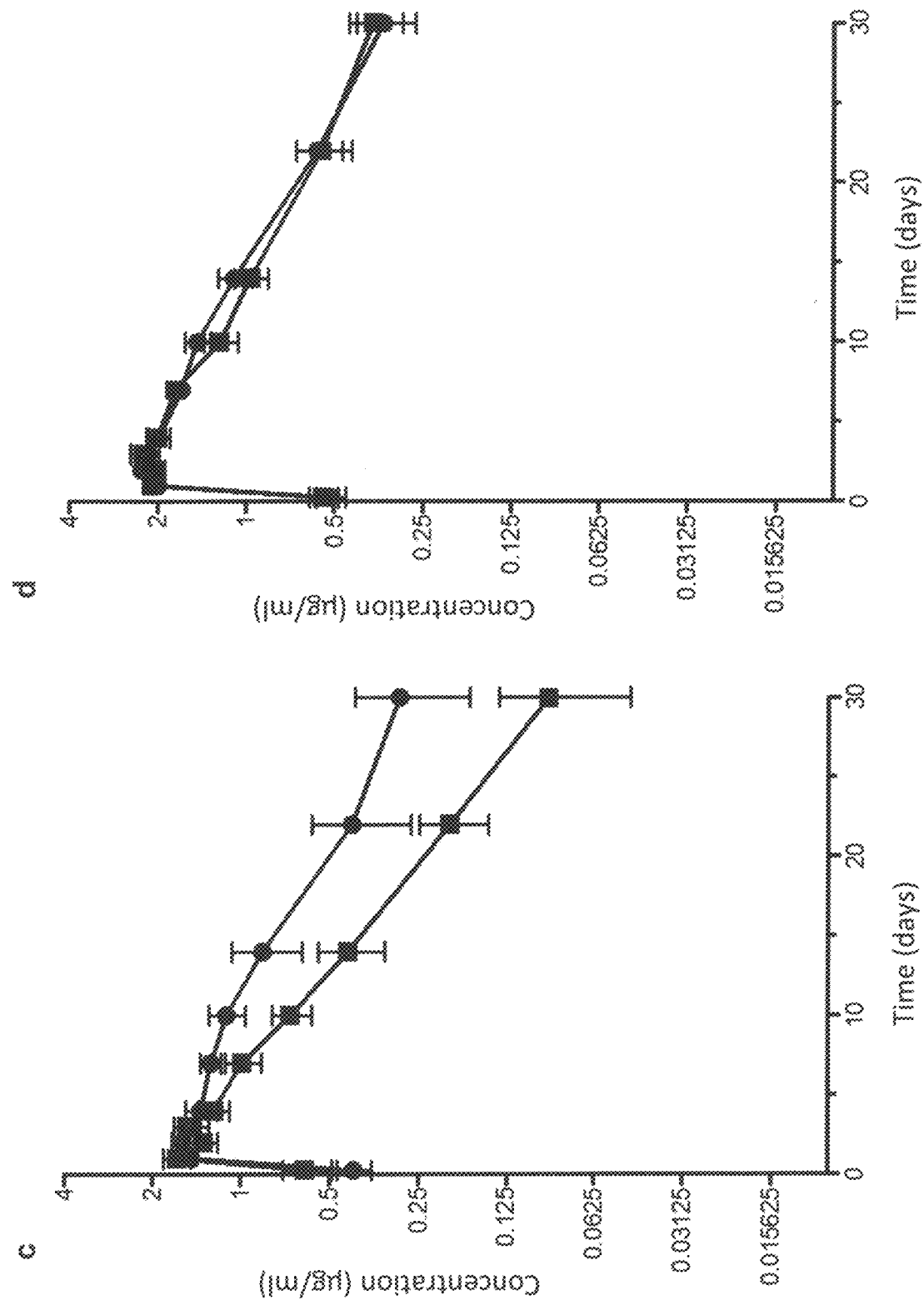
Fig. 5c-d

SEQUENCE LISTING

```
<160> NUMBER OF SEQ ID NOS: 165

<210> SEQ ID NO 1
<211> LENGTH: 354
<212> TYPE: DNA
<213> ORGANISM: Artificial Sequence
<220> FEATURE:
<223> OTHER INFORMATION: Synthetic

<400> SEQUENCE: 1
caggtgcagc tggtacagtc tggggctgag gtgaagaagc ctggggcctc agtaaaagtc      60
tcctgcaagg cttctggata caccttcacc agttatgata tcaactgggt gcgacaggcc     120
actggacagg gcttgagtg gatgggatgg attaaccctaa acagtgatta cacaggctat     180
gtacagaagt tccagggcag agtcaccatg accagggaca cctccataag tacagcctac     240
atggagctga gcagcctgag atctgaggac acggccgtgt attactgtgc gacatcacgg     300
tggtctgaac acttccacca ctggggccag ggcaccctgg tcactgtctc ctca            354

<210> SEQ ID NO 2
<211> LENGTH: 118
<212> TYPE: PRT
<213> ORGANISM: Artificial Sequence
<220> FEATURE:
<223> OTHER INFORMATION: Synthetic

<400> SEQUENCE: 2

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Asp Ile Asn Trp Val Arg Gln Ala Thr Gly Gln Gly Leu Glu Trp Met
            35                  40                  45

Gly Trp Ile Asn Pro Asn Ser Asp Tyr Thr Gly Tyr Val Gln Lys Phe
        50                  55                  60

Gln Gly Arg Val Thr Met Thr Arg Asp Thr Ser Ile Ser Thr Ala Tyr
65                  70                  75                  80

Met Glu Leu Ser Ser Leu Arg Ser Glu Asp Thr Ala Val Tyr Tyr Cys
                85                  90                  95

Ala Thr Ser Arg Trp Ser Glu His Phe His His Trp Gly Gln Gly Thr
            100                 105                 110

Leu Val Thr Val Ser Ser
        115

<210> SEQ ID NO 3
<211> LENGTH: 24
<212> TYPE: DNA
<213> ORGANISM: Artificial Sequence
<220> FEATURE:
<223> OTHER INFORMATION: Synthetic
```

```
<400> SEQUENCE: 3
ggatacacct tcaccagtta tgat                                          24

<210> SEQ ID NO 4
<211> LENGTH: 8
<212> TYPE: PRT
<213> ORGANISM: Artificial Sequence
<220> FEATURE:
<223> OTHER INFORMATION: Synthetic

<400> SEQUENCE: 4

Gly Tyr Thr Phe Thr Ser Tyr Asp
1               5

<210> SEQ ID NO 5
<211> LENGTH: 24
<212> TYPE: DNA
<213> ORGANISM: Artificial Sequence
<220> FEATURE:
<223> OTHER INFORMATION: Synthetic

<400> SEQUENCE: 5
attaacccta acagtgatta caca                                          24

<210> SEQ ID NO 6
<211> LENGTH: 8
<212> TYPE: PRT
<213> ORGANISM: Artificial Sequence
<220> FEATURE:
<223> OTHER INFORMATION: Synthetic

<400> SEQUENCE: 6

Ile Asn Pro Asn Ser Asp Tyr Thr
1               5

<210> SEQ ID NO 7
<211> LENGTH: 33
<212> TYPE: DNA
<213> ORGANISM: Artificial Sequence
<220> FEATURE:
<223> OTHER INFORMATION: Synthetic

<400> SEQUENCE: 7
gcgacatcac ggtggtctga acacttccac cac                                33

<210> SEQ ID NO 8
<211> LENGTH: 11
<212> TYPE: PRT
<213> ORGANISM: Artificial Sequence
<220> FEATURE:
<223> OTHER INFORMATION: Synthetic

<400> SEQUENCE: 8

Ala Thr Ser Arg Trp Ser Glu His Phe His His
1               5                   10

<210> SEQ ID NO 9
<211> LENGTH: 342
<212> TYPE: DNA
<213> ORGANISM: Artificial Sequence
<220> FEATURE:
<223> OTHER INFORMATION: Synthetic

<400> SEQUENCE: 9
gacatcgtga tgacccagtc tccagactcc ctggctgtgt ctctgggcga gagggccacc    60
```

-continued

| | |
|---|---|
| atcaactgca agtccagcca gagtgtttta tacagctcca acaataagaa ctacttagct | 120 |
| tggtaccagc acaaaccagg acagcctcct aacctactca tttactgggc atctacccgg | 180 |
| gaatccgggg tccctgaccg attcagtggc agcgggtctg ggacagattt cactctcacc | 240 |
| atcagcagcc tgcaggctga agatgtggca gtttattact gtcaccaata ttatagtact | 300 |
| ccattcactt tcggccctgg gaccaaagtg gatatcaaac ga | 342 |

<210> SEQ ID NO 10
<211> LENGTH: 114
<212> TYPE: PRT
<213> ORGANISM: Artificial Sequence
<220> FEATURE:
<223> OTHER INFORMATION: Synthetic

<400> SEQUENCE: 10

Asp Ile Val Met Thr Gln Ser Pro Asp Ser Leu Ala Val Ser Leu Gly
1               5                   10                  15

Glu Arg Ala Thr Ile Asn Cys Lys Ser Ser Gln Ser Val Leu Tyr Ser
            20                  25                  30

Ser Asn Asn Lys Asn Tyr Leu Ala Trp Tyr Gln His Lys Pro Gly Gln
        35                  40                  45

Pro Pro Asn Leu Leu Ile Tyr Trp Ala Ser Thr Arg Glu Ser Gly Val
    50                  55                  60

Pro Asp Arg Phe Ser Gly Ser Gly Ser Gly Thr Asp Phe Thr Leu Thr
65                  70                  75                  80

Ile Ser Ser Leu Gln Ala Glu Asp Val Ala Val Tyr Tyr Cys His Gln
                85                  90                  95

Tyr Tyr Ser Thr Pro Phe Thr Phe Gly Pro Gly Thr Lys Val Asp Ile
            100                 105                 110

Lys Arg

<210> SEQ ID NO 11
<211> LENGTH: 36
<212> TYPE: DNA
<213> ORGANISM: Artificial Sequence
<220> FEATURE:
<223> OTHER INFORMATION: Synthetic

<400> SEQUENCE: 11
cagagtgttt tatacagctc caacaataag aactac                                36

<210> SEQ ID NO 12
<211> LENGTH: 12
<212> TYPE: PRT
<213> ORGANISM: Artificial Sequence
<220> FEATURE:
<223> OTHER INFORMATION: Synthetic

<400> SEQUENCE: 12

Gln Ser Val Leu Tyr Ser Ser Asn Asn Lys Asn Tyr
1               5                   10

<210> SEQ ID NO 13
<211> LENGTH: 9
<212> TYPE: DNA
<213> ORGANISM: Artificial Sequence
<220> FEATURE:
<223> OTHER INFORMATION: Synthetic

<400> SEQUENCE: 13 tgggcatct                                                               9

<210> SEQ ID NO 14
<211> LENGTH: 3
<212> TYPE: PRT
<213> ORGANISM: Artificial Sequence
<220> FEATURE:
<223> OTHER INFORMATION: Synthetic

<400> SEQUENCE: 14

Trp Ala Ser
1

<210> SEQ ID NO 15
<211> LENGTH: 27
<212> TYPE: DNA
<213> ORGANISM: Artificial Sequence
<220> FEATURE:
<223> OTHER INFORMATION: Synthetic

<400> SEQUENCE: 15
caccaatatt atagtactcc attcact                                         27

<210> SEQ ID NO 16
<211> LENGTH: 9
<212> TYPE: PRT
<213> ORGANISM: Artificial Sequence
<220> FEATURE:
<223> OTHER INFORMATION: Synthetic

<400> SEQUENCE: 16

His Gln Tyr Tyr Ser Thr Pro Phe Thr
1               5

<210> SEQ ID NO 17
<211> LENGTH: 372
<212> TYPE: DNA
<213> ORGANISM: Artificial Sequence
<220> FEATURE:
<223> OTHER INFORMATION: Synthetic

<400> SEQUENCE: 17
caggtgcagc tggtggagtc tgggggaggc gtggtccagc ctggagggtc ccggagactc      60
tcctgtgtag tgtctggatt catcttcagt agctatggca tgcactgggt ccgccaggct     120
ccaggcaagg ggctggagtg ggtggcactt atattttatg atggaagtaa tgaatactat     180
gtagactccg tgaagggccg attcaccatc tccagagaca attccaagaa cacactgtat     240
ctccaaatga acagcctgag agccgaggac acggctgtgt attactgtgc gcgagagggc     300
tacagtcagc ggtacaagta ttacttcggt atggacgtct ggggccaagg gaccacggtc     360
accgtctcct ca                                                        372

<210> SEQ ID NO 18
<211> LENGTH: 124
<212> TYPE: PRT
<213> ORGANISM: Artificial Sequence
<220> FEATURE:
<223> OTHER INFORMATION: Synthetic

<400> SEQUENCE: 18

Gln Val Gln Leu Val Glu Ser Gly Gly Gly Val Val Gln Pro Gly Arg
1               5                   10                  15

Ser Arg Arg Leu Ser Cys Val Val Ser Gly Phe Ile Phe Ser Ser Tyr
            20                  25                  30

```
Gly Met His Trp Val Arg Gln Ala Pro Gly Lys Gly Leu Glu Trp Val
         35                  40                  45

Ala Leu Ile Phe Tyr Asp Gly Ser Asn Glu Tyr Tyr Val Asp Ser Val
 50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Arg Glu Gly Tyr Ser Gln Arg Tyr Lys Tyr Tyr Phe Gly Met Asp
            100                 105                 110

Val Trp Gly Gln Gly Thr Thr Val Thr Val Ser Ser
        115                 120
```

<210> SEQ ID NO 19
<211> LENGTH: 24
<212> TYPE: DNA
<213> ORGANISM: Artificial Sequence
<220> FEATURE:
<223> OTHER INFORMATION: Synthetic

<400> SEQUENCE: 19
ggattcatct tcagtagcta tggc                                          24

<210> SEQ ID NO 20
<211> LENGTH: 8
<212> TYPE: PRT
<213> ORGANISM: Artificial Sequence
<220> FEATURE:
<223> OTHER INFORMATION: Synthetic

<400> SEQUENCE: 20

Gly Phe Ile Phe Ser Ser Tyr Gly
 1               5

<210> SEQ ID NO 21
<211> LENGTH: 24
<212> TYPE: DNA
<213> ORGANISM: Artificial Sequence
<220> FEATURE:
<223> OTHER INFORMATION: Synthetic

<400> SEQUENCE: 21
atattttatg atggaagtaa tgaa                                          24

<210> SEQ ID NO 22
<211> LENGTH: 8
<212> TYPE: PRT
<213> ORGANISM: Artificial Sequence
<220> FEATURE:
<223> OTHER INFORMATION: Synthetic

<400> SEQUENCE: 22

Ile Phe Tyr Asp Gly Ser Asn Glu
 1               5

<210> SEQ ID NO 23
<211> LENGTH: 51
<212> TYPE: DNA
<213> ORGANISM: Artificial Sequence
<220> FEATURE:
<223> OTHER INFORMATION: Synthetic

<400> SEQUENCE: 23
gcgcgagagg gctacagtca gcggtacaag tattacttcg gtatggacgt c            51

<210> SEQ ID NO 24
<211> LENGTH: 17
<212> TYPE: PRT
<213> ORGANISM: Artificial Sequence
<220> FEATURE:
<223> OTHER INFORMATION: Synthetic

<400> SEQUENCE: 24

Ala Arg Glu Gly Tyr Ser Gln Arg Tyr Lys Tyr Tyr Phe Gly Met Asp
1               5                   10                  15

Val

<210> SEQ ID NO 25
<211> LENGTH: 324
<212> TYPE: DNA
<213> ORGANISM: Artificial Sequence
<220> FEATURE:
<223> OTHER INFORMATION: Synthetic

<400> SEQUENCE: 25
gacatccaga tgacccagtc tccatcttcc gtgtctgcat ctgtgggaga cagagtcacc      60
atcacttgtc gggcgagtca gggtattagc agctggttag cctggtatca gcagcaacca    120
gggaaagccc ctaagctcct gatctatgct gcatccagtt tgcaaagtgg ggtcccatca    180
aggttcagcg gcagtggatc tgggacagat ttcactctca ccatcagcag cctgcagcct    240
gaagattttg caacttacta ttgtcaacag actaacagtt tcccgctcac tttcggcgga    300
gggaccaagg tggagatcaa acga                                            324

<210> SEQ ID NO 26
<211> LENGTH: 108
<212> TYPE: PRT
<213> ORGANISM: Artificial Sequence
<220> FEATURE:
<223> OTHER INFORMATION: Synthetic

<400> SEQUENCE: 26

Asp Ile Gln Met Thr Gln Ser Pro Ser Ser Val Ser Ala Ser Val Gly
1               5                   10                  15

Asp Arg Val Thr Ile Thr Cys Arg Ala Ser Gln Gly Ile Ser Ser Trp
            20                  25                  30

Leu Ala Trp Tyr Gln Gln Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Thr Asn Ser Phe Pro Leu
                85                  90                  95

Thr Phe Gly Gly Gly Thr Lys Val Glu Ile Lys Arg
            100                 105

<210> SEQ ID NO 27
<211> LENGTH: 18
<212> TYPE: DNA
<213> ORGANISM: Artificial Sequence
<220> FEATURE:
<223> OTHER INFORMATION: Synthetic

<400> SEQUENCE: 27
cagggtatta gcagctgg                                                    18

<210> SEQ ID NO 28
<211> LENGTH: 6
<212> TYPE: PRT
<213> ORGANISM: Artificial Sequence
<220> FEATURE:
<223> OTHER INFORMATION: Synthetic

<400> SEQUENCE: 28

Gln Gly Ile Ser Ser Trp
1               5

<210> SEQ ID NO 29
<211> LENGTH: 9
<212> TYPE: DNA
<213> ORGANISM: Artificial Sequence
<220> FEATURE:
<223> OTHER INFORMATION: Synthetic

<400> SEQUENCE: 29 gctgcatcc                                                               9

<210> SEQ ID NO 30
<211> LENGTH: 3
<212> TYPE: PRT
<213> ORGANISM: Artificial Sequence
<220> FEATURE:
<223> OTHER INFORMATION: Synthetic

<400> SEQUENCE: 30

Ala Ala Ser
1

<210> SEQ ID NO 31
<211> LENGTH: 27
<212> TYPE: DNA
<213> ORGANISM: Artificial Sequence
<220> FEATURE:
<223> OTHER INFORMATION: Synthetic

<400> SEQUENCE: 31
caacagacta acagtttccc gctcact                                          27

<210> SEQ ID NO 32
<211> LENGTH: 9
<212> TYPE: PRT
<213> ORGANISM: Artificial Sequence
<220> FEATURE:
<223> OTHER INFORMATION: Synthetic

<400> SEQUENCE: 32

Gln Gln Thr Asn Ser Phe Pro Leu Thr
1               5

<210> SEQ ID NO 33
<211> LENGTH: 366
<212> TYPE: DNA
<213> ORGANISM: Artificial Sequence
<220> FEATURE:
<223> OTHER INFORMATION: Synthetic

<400> SEQUENCE: 33
gaggtgcagc tggtggagtc tgggggaggc ttggtacagc ctggggggtc cctgagactc        60
tcctgtgcag cctctggatt ccccttcagt agctacgaca tgcactgggt ccgccaagct       120

```
acaggaaaag gtctggagtg ggtctcagct attggtactg ctggtgccac atactatcca    180
ggctccgtga agggccgatt caccatctcc agagaaaatg ccaagaactc cttgtatctt    240
caaatgaaca gcctgagagc cggggacacg gctgtgtatt actgtgcaag aggggattac    300 gtttgggga cttatcgtcc cctctttgac tactggggcc agggaaccct ggtcaccgtc    360
tcctca                                                                366
```

<210> SEQ ID NO 34
<211> LENGTH: 122
<212> TYPE: PRT
<213> ORGANISM: Artificial Sequence
<220> FEATURE:
<223> OTHER INFORMATION: Synthetic

<400> SEQUENCE: 34

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Pro Phe Ser Ser Tyr
            20                  25                  30

Asp Met His Trp Val Arg Gln Ala Thr Gly Lys Gly Leu Glu Trp Val
        35                  40                  45

Ser Ala Ile Gly Thr Ala Gly Ala Thr Tyr Tyr Pro Gly Ser Val Lys
    50                  55                  60

Gly Arg Phe Thr Ile Ser Arg Glu Asn Ala Lys Asn Ser Leu Tyr Leu
65                  70                  75                  80

Gln Met Asn Ser Leu Arg Ala Gly Asp Thr Ala Val Tyr Tyr Cys Ala
                85                  90                  95

Arg Gly Asp Tyr Val Trp Gly Thr Tyr Arg Pro Leu Phe Asp Tyr Trp
            100                 105                 110

Gly Gln Gly Thr Leu Val Thr Val Ser Ser
        115                 120
```

<210> SEQ ID NO 35
<211> LENGTH: 24
<212> TYPE: DNA
<213> ORGANISM: Artificial Sequence
<220> FEATURE:
<223> OTHER INFORMATION: Synthetic

<400> SEQUENCE: 35

```
ggattcccct tcagtagcta cgac                                             24
```

<210> SEQ ID NO 36
<211> LENGTH: 8
<212> TYPE: PRT
<213> ORGANISM: Artificial Sequence
<220> FEATURE:
<223> OTHER INFORMATION: Synthetic

<400> SEQUENCE: 36

```
Gly Phe Pro Phe Ser Ser Tyr Asp
1               5
```

<210> SEQ ID NO 37
<211> LENGTH: 21
<212> TYPE: DNA
<213> ORGANISM: Artificial Sequence
<220> FEATURE:
<223> OTHER INFORMATION: Synthetic

<400> SEQUENCE: 37

```
attggtactg ctggtgccac a                                                   21
```

<210> SEQ ID NO 38
<211> LENGTH: 7
<212> TYPE: PRT
<213> ORGANISM: Artificial Sequence
<220> FEATURE:
<223> OTHER INFORMATION: Synthetic

<400> SEQUENCE: 38

Ile Gly Thr Ala Gly Ala Thr
1               5

<210> SEQ ID NO 39
<211> LENGTH: 48
<212> TYPE: DNA
<213> ORGANISM: Artificial Sequence
<220> FEATURE:
<223> OTHER INFORMATION: Synthetic

<400> SEQUENCE: 39

```
gcaagagggg attacgtttg ggggacttat cgtcccctct ttgactac               48
```

<210> SEQ ID NO 40
<211> LENGTH: 16
<212> TYPE: PRT
<213> ORGANISM: Artificial Sequence
<220> FEATURE:
<223> OTHER INFORMATION: Synthetic

<400> SEQUENCE: 40

Ala Arg Gly Asp Tyr Val Trp Gly Thr Tyr Arg Pro Leu Phe Asp Tyr
1               5                   10                  15

<210> SEQ ID NO 41
<211> LENGTH: 321
<212> TYPE: DNA
<213> ORGANISM: Artificial Sequence
<220> FEATURE:
<223> OTHER INFORMATION: Synthetic

<400> SEQUENCE: 41

```
gacatccagt tgacccagtc tccatccttc ctgtctgcat ctgtaggaga cagagtcacc    60
atcacttgct gggccagtca gggcattaac aattatttag cctggtatca acaaaaacca   120
gggaaagccc ctaagctcct gatctatgct gcatccactt tgcaaactgg ggtcccatca   180
aggttcagcg gcagtggatc tgggacagaa ttcactctca caatcagcag cctgcagcct   240
gaagattttg caactcatta ctgtcagcag cttaatagtt acccgctcac tttcggcgga   300
gggaccaagg tggagatcaa a                                              321
```

<210> SEQ ID NO 42
<211> LENGTH: 107
<212> TYPE: PRT
<213> ORGANISM: Artificial Sequence
<220> FEATURE:
<223> OTHER INFORMATION: Synthetic

<400> SEQUENCE: 42

Asp Ile Gln Leu Thr Gln Ser Pro Ser Phe Leu Ser Ala Ser Val Gly
1               5                   10                  15

Asp Arg Val Thr Ile Thr Cys Trp Ala Ser Gln Gly Ile Asn Asn Tyr
            20                  25                  30

Leu Ala Trp Tyr Gln Gln Lys Pro Gly Lys Ala Pro Lys Leu Leu Ile

```
                35                  40                  45
Tyr Ala Ala Ser Thr Leu Gln Thr Gly Val Pro Ser Arg Phe Ser Gly
     50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Gln Gln Leu Asn Ser Tyr Pro Leu
                 85                  90                  95

Thr Phe Gly Gly Gly Thr Lys Val Glu Ile Lys
        100                 105

<210> SEQ ID NO 43
<211> LENGTH: 18
<212> TYPE: DNA
<213> ORGANISM: Artificial Sequence
<220> FEATURE:
<223> OTHER INFORMATION: Synthetic

<400> SEQUENCE: 43
cagggcatta acaattat                                                     18

<210> SEQ ID NO 44
<211> LENGTH: 6
<212> TYPE: PRT
<213> ORGANISM: Artificial Sequence
<220> FEATURE:
<223> OTHER INFORMATION: Synthetic

<400> SEQUENCE: 44

Gln Gly Ile Asn Asn Tyr
 1               5

<210> SEQ ID NO 45
<211> LENGTH: 9
<212> TYPE: DNA
<213> ORGANISM: Artificial Sequence
<220> FEATURE:
<223> OTHER INFORMATION: Synthetic

<400> SEQUENCE: 45 gctgcatcc                                                                9

<210> SEQ ID NO 46
<211> LENGTH: 3
<212> TYPE: PRT
<213> ORGANISM: Artificial Sequence
<220> FEATURE:
<223> OTHER INFORMATION: Synthetic

<400> SEQUENCE: 46

Ala Ala Ser
 1

<210> SEQ ID NO 47
<211> LENGTH: 27
<212> TYPE: DNA
<213> ORGANISM: Artificial Sequence
<220> FEATURE:
<223> OTHER INFORMATION: Synthetic

<400> SEQUENCE: 47
cagcagctta atagttaccc gctcact                                           27

<210> SEQ ID NO 48
<211> LENGTH: 9
```

<212> TYPE: PRT
<213> ORGANISM: Artificial Sequence
<220> FEATURE:
<223> OTHER INFORMATION: Synthetic

<400> SEQUENCE: 48

Gln Gln Leu Asn Ser Tyr Pro Leu Thr
1               5

<210> SEQ ID NO 49
<211> LENGTH: 372
<212> TYPE: DNA
<213> ORGANISM: Artificial Sequence
<220> FEATURE:
<223> OTHER INFORMATION: Synthetic

<400> SEQUENCE: 49
caggtgcagc tggtggagtc tgggggaggc gtggtccagc ctggggaggtc cctgagactc      60 tcctgtgcag cgtctggatt caccttcagt agatatggca tacactgggt ccgccaggct     120
ccaggcaagg ggctggagtg ggtggcagtt atttggcatg atggaagtaa taaatactat     180
gcagactccg tgaagggccg attcaccatc tccagagaca attccaagaa cacgctgtat     240
ctgcaaatga ccagcctgag agccgaggac acggctgtgt attactgtgc gagagatgga     300
ctggagatac gagatcacta ctactacggt atggacgtct ggggccaagg gaccacggtc     360
accgtctcct ca                                                         372

<210> SEQ ID NO 50
<211> LENGTH: 124
<212> TYPE: PRT
<213> ORGANISM: Artificial Sequence
<220> FEATURE:
<223> OTHER INFORMATION: Synthetic

<400> SEQUENCE: 50

Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Arg Tyr
                20                  25                  30

Gly Ile His Trp Val Arg Gln Ala Pro Gly Lys Gly Leu Glu Trp Val
            35                  40                  45

Ala Val Ile Trp His Asp Gly Ser Asn Lys Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Thr Ser Leu Arg Ala Glu Asp Thr Ala Val Tyr Tyr Cys
                85                  90                  95

Ala Arg Asp Gly Leu Glu Ile Arg Asp His Tyr Tyr Tyr Gly Met Asp
            100                 105                 110

Val Trp Gly Gln Gly Thr Thr Val Thr Val Ser Ser
        115                 120

<210> SEQ ID NO 51
<211> LENGTH: 24
<212> TYPE: DNA
<213> ORGANISM: Artificial Sequence
<220> FEATURE:
<223> OTHER INFORMATION: Synthetic

<400> SEQUENCE: 51
ggattcacct tcagtagata tggc                                            24

<210> SEQ ID NO 52
<211> LENGTH: 8
<212> TYPE: PRT
<213> ORGANISM: Artificial Sequence
<220> FEATURE:
<223> OTHER INFORMATION: Synthetic

<400> SEQUENCE: 52

Gly Phe Thr Phe Ser Arg Tyr Gly
1               5

<210> SEQ ID NO 53
<211> LENGTH: 24
<212> TYPE: DNA
<213> ORGANISM: Artificial Sequence
<220> FEATURE:
<223> OTHER INFORMATION: Synthetic

<400> SEQUENCE: 53
atttggcatg atggaagtaa taaa                                          24

<210> SEQ ID NO 54
<211> LENGTH: 8
<212> TYPE: PRT
<213> ORGANISM: Artificial Sequence
<220> FEATURE:
<223> OTHER INFORMATION: Synthetic

<400> SEQUENCE: 54

Ile Trp His Asp Gly Ser Asn Lys
1               5

<210> SEQ ID NO 55
<211> LENGTH: 51
<212> TYPE: DNA
<213> ORGANISM: Artificial Sequence
<220> FEATURE:
<223> OTHER INFORMATION: Synthetic

<400> SEQUENCE: 55
gcgagagatg gactggagat acgagatcac tactactacg gtatggacgt c            51

<210> SEQ ID NO 56
<211> LENGTH: 17
<212> TYPE: PRT
<213> ORGANISM: Artificial Sequence
<220> FEATURE:
<223> OTHER INFORMATION: Synthetic

<400> SEQUENCE: 56

Ala Arg Asp Gly Leu Glu Ile Arg Asp His Tyr Tyr Tyr Gly Met Asp
1               5                   10                  15

Val

<210> SEQ ID NO 57
<211> LENGTH: 321
<212> TYPE: DNA
<213> ORGANISM: Artificial Sequence
<220> FEATURE:
<223> OTHER INFORMATION: Synthetic

<400> SEQUENCE: 57
gacatccaga tgacccagtc tccttccacc ctgtctgcat cggtaggaga cagagtcacc      60
atcacttgcc gggccagtca gagtactagt agttggttgg cctggtatca acagaaacca     120

```
gggaaagccc ctacgctcct gatctataag gcgtctagtt tagaaagtgg ggtcccatca      180
aaattcagcg gcagtggatc tgggacagaa ttcactctca ccatcagcag cctgcagcct      240
gatgattttg caacgtatta ctgccaacag tataacaggt attctcggac gttcggccaa      300
gggaccaagg tggaaattaa a                                                321
```

<210> SEQ ID NO 58
<211> LENGTH: 107
<212> TYPE: PRT
<213> ORGANISM: Artificial Sequence
<220> FEATURE:
<223> OTHER INFORMATION: Synthetic

<400> SEQUENCE: 58

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Thr Ser Ser Trp
            20                  25                  30

Leu Ala Trp Tyr Gln Gln Lys Pro Gly Lys Ala Pro Thr Leu Leu Ile
        35                  40                  45

Tyr Lys Ala Ser Ser Leu Glu Ser Gly Val Pro Ser Lys Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Arg Tyr Ser Arg
                85                  90                  95

Thr Phe Gly Gln Gly Thr Lys Val Glu Ile Lys
            100                 105
```

<210> SEQ ID NO 59
<211> LENGTH: 18
<212> TYPE: DNA
<213> ORGANISM: Artificial Sequence
<220> FEATURE:
<223> OTHER INFORMATION: Synthetic

<400> SEQUENCE: 59

```
cagagtacta gtagttgg                                                     18
```

<210> SEQ ID NO 60
<211> LENGTH: 6
<212> TYPE: PRT
<213> ORGANISM: Artificial Sequence
<220> FEATURE:
<223> OTHER INFORMATION: Synthetic

<400> SEQUENCE: 60

```
Gln Ser Thr Ser Ser Trp
1               5
```

<210> SEQ ID NO 61
<211> LENGTH: 9
<212> TYPE: DNA
<213> ORGANISM: Artificial Sequence
<220> FEATURE:
<223> OTHER INFORMATION: Synthetic

<400> SEQUENCE: 61

```
aaggcgtct                                                                9
```

<210> SEQ ID NO 62

<210> SEQ ID NO 62
<211> LENGTH: 3
<212> TYPE: PRT
<213> ORGANISM: Artificial Sequence
<220> FEATURE:
<223> OTHER INFORMATION: Synthetic

<400> SEQUENCE: 62

Lys Ala Ser
1

<210> SEQ ID NO 63
<211> LENGTH: 27
<212> TYPE: DNA
<213> ORGANISM: Artificial Sequence
<220> FEATURE:
<223> OTHER INFORMATION: Synthetic

<400> SEQUENCE: 63
caacagtata acaggtattc tcggacg        27

<210> SEQ ID NO 64
<211> LENGTH: 9
<212> TYPE: PRT
<213> ORGANISM: Artificial Sequence
<220> FEATURE:
<223> OTHER INFORMATION: Synthetic

<400> SEQUENCE: 64

Gln Gln Tyr Asn Arg Tyr Ser Arg Thr
1               5

<210> SEQ ID NO 65
<211> LENGTH: 378
<212> TYPE: DNA
<213> ORGANISM: Artificial Sequence
<220> FEATURE:
<223> OTHER INFORMATION: Synthetic

<400> SEQUENCE: 65
gaagtgcagt tggtggagtc tgggggaggc ttggtacagc ctggcaggtc cctgagactc        60
tcctgtgcag cctctggatt cacctttgat gattatgcca tgcactgggt ccggcaagtt       120
ccagggaagg gcctggagtg ggtctcaggt attagttgga atagtggtag cataggctat       180
gcggactctg tgaagggccg attcaccatc tccagagaca acgccaagaa ctccctgtat       240
ctgcaaatga atagtctgag agctgaggac acggccttgt attactgtgc aaaagatatc       300
catgactacg gaaaagatta ctactactac tacggtatgg acgtctgggg ccaagggacc       360
acggtcaccg tctcctca                                                     378

<210> SEQ ID NO 66
<211> LENGTH: 126
<212> TYPE: PRT
<213> ORGANISM: Artificial Sequence
<220> FEATURE:
<223> OTHER INFORMATION: Synthetic

<400> SEQUENCE: 66

Glu Val Gln Leu Val Glu Ser Gly Gly Gly Leu Val Gln Pro Gly Arg
1               5                   10                  15

Ser Leu Arg Leu Ser Cys Ala Ala Ser Gly Phe Thr Phe Asp Asp Tyr
            20                  25                  30

Ala Met His Trp Val Arg Gln Val Pro Gly Lys Gly Leu Glu Trp Val
        35                  40                  45

Ser Gly Ile Ser Trp Asn Ser Gly Ser Ile Gly Tyr Ala Asp Ser Val
        50                  55                  60

Lys Gly Arg Phe Thr Ile Ser Arg Asp Asn Ala Lys Asn Ser Leu Tyr
 65                  70                  75                  80

Leu Gln Met Asn Ser Leu Arg Ala Glu Asp Thr Ala Leu Tyr Tyr Cys
                85                  90                  95

Ala Lys Asp Ile His Asp Tyr Gly Lys Asp Tyr Tyr Tyr Tyr Tyr Gly
            100                 105                 110

Met Asp Val Trp Gly Gln Gly Thr Thr Val Thr Val Ser Ser
        115                 120                 125

<210> SEQ ID NO 67
<211> LENGTH: 24
<212> TYPE: DNA
<213> ORGANISM: Artificial Sequence
<220> FEATURE:
<223> OTHER INFORMATION: Synthetic

<400> SEQUENCE: 67
ggattcacct ttgatgatta tgcc                                        24

<210> SEQ ID NO 68
<211> LENGTH: 8
<212> TYPE: PRT
<213> ORGANISM: Artificial Sequence
<220> FEATURE:
<223> OTHER INFORMATION: Synthetic

<400> SEQUENCE: 68

Gly Phe Thr Phe Asp Asp Tyr Ala
 1               5

<210> SEQ ID NO 69
<211> LENGTH: 24
<212> TYPE: DNA
<213> ORGANISM: Artificial Sequence
<220> FEATURE:
<223> OTHER INFORMATION: Synthetic

<400> SEQUENCE: 69
attagttgga atagtggtag cata                                        24

<210> SEQ ID NO 70
<211> LENGTH: 8
<212> TYPE: PRT
<213> ORGANISM: Artificial Sequence
<220> FEATURE:
<223> OTHER INFORMATION: Synthetic

<400> SEQUENCE: 70

Ile Ser Trp Asn Ser Gly Ser Ile
 1               5

<210> SEQ ID NO 71
<211> LENGTH: 57
<212> TYPE: DNA
<213> ORGANISM: Artificial Sequence
<220> FEATURE:
<223> OTHER INFORMATION: Synthetic

<400> SEQUENCE: 71
gcaaaagata tccatgacta cggaaaagat tactactact actacggtat ggacgtc    57

<210> SEQ ID NO 72

<211> LENGTH: 19
<212> TYPE: PRT
<213> ORGANISM: Artificial Sequence
<220> FEATURE:
<223> OTHER INFORMATION: Synthetic

<400> SEQUENCE: 72

Ala Lys Asp Ile His Asp Tyr Gly Lys Asp Tyr Tyr Tyr Tyr Gly
1               5                   10                  15
Met Asp Val

<210> SEQ ID NO 73
<211> LENGTH: 324
<212> TYPE: DNA
<213> ORGANISM: Artificial Sequence
<220> FEATURE:
<223> OTHER INFORMATION: Synthetic

<400> SEQUENCE: 73
gaaattgcgt tgacgcagtc tccaggcacc ctgtctttgt ctccagggga aagagccacc      60
ctctcctgca gggccagtca gagtgttagc agcacctatt tagcctggta ccagcagaaa     120
cctggccagg ctcccaggct cctcatctat ggtgcatcca gcagggccac tggcatccca     180
gacaggttca gtggcagtgg gtctgggaca gacttcactc tcaccatcag cagactggag     240
cctgaagatt ttgcagtgta ttactgtcag cagtatgata gttcaccgat cacccttcggc    300
caagggacac gactggagat taaa                                            324

<210> SEQ ID NO 74
<211> LENGTH: 108
<212> TYPE: PRT
<213> ORGANISM: Artificial Sequence
<220> FEATURE:
<223> OTHER INFORMATION: Synthetic

<400> SEQUENCE: 74

Glu Ile Ala Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Thr
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Asp Ser Ser Pro
                85                  90                  95

Ile Thr Phe Gly Gln Gly Thr Arg Leu Glu Ile Lys
            100                 105

<210> SEQ ID NO 75
<211> LENGTH: 21
<212> TYPE: DNA
<213> ORGANISM: Artificial Sequence
<220> FEATURE:
<223> OTHER INFORMATION: Synthetic

<400> SEQUENCE: 75
cagagtgtta gcagcaccta t                                               21

```
<210> SEQ ID NO 76
<211> LENGTH: 7
<212> TYPE: PRT
<213> ORGANISM: Artificial Sequence
<220> FEATURE:
<223> OTHER INFORMATION: Synthetic

<400> SEQUENCE: 76

Gln Ser Val Ser Ser Thr Tyr
1               5

<210> SEQ ID NO 77
<211> LENGTH: 9
<212> TYPE: DNA
<213> ORGANISM: Artificial Sequence
<220> FEATURE:
<223> OTHER INFORMATION: Synthetic

<400> SEQUENCE: 77 ggtgcatcc                                                                 9

<210> SEQ ID NO 78
<211> LENGTH: 3
<212> TYPE: PRT
<213> ORGANISM: Artificial Sequence
<220> FEATURE:
<223> OTHER INFORMATION: Synthetic

<400> SEQUENCE: 78

Gly Ala Ser
1

<210> SEQ ID NO 79
<211> LENGTH: 27
<212> TYPE: DNA
<213> ORGANISM: Artificial Sequence
<220> FEATURE:
<223> OTHER INFORMATION: Synthetic

<400> SEQUENCE: 79
cagcagtatg atagttcacc gatcacc                                            27

<210> SEQ ID NO 80
<211> LENGTH: 9
<212> TYPE: PRT
<213> ORGANISM: Artificial Sequence
<220> FEATURE:
<223> OTHER INFORMATION: Synthetic

<400> SEQUENCE: 80

Gln Gln Tyr Asp Ser Ser Pro Ile Thr
1               5

<210> SEQ ID NO 81
<211> LENGTH: 354
<212> TYPE: DNA
<213> ORGANISM: Artificial Sequence
<220> FEATURE:
<223> OTHER INFORMATION: Synthetic

<400> SEQUENCE: 81
caggtgcagc tggtggaatc tgggggaggc gtggtccagc ctggagggtc cctgagactc        60
tcctgtgcag cgtctggatt caccttcagt gcctatgcca tgcactgggt ccgccaggct       120
ccaggcaagg ggctggagtg ggtggcagtt atatggtatg atggaagtaa taaaaattat       180
gcagactccg tgaagggccg attcaccgtc tccagagaca attccaagaa cacgctgtat       240
```

```
ctggaaatga acagcctgag agccgaggac acggctgtgt attactgtgc gagagatcta      300
atggtcggag ttactaacta ttggggccag ggaaccctgg tcaccgtctc caca            354
```

<210> SEQ ID NO 82
<211> LENGTH: 118
<212> TYPE: PRT
<213> ORGANISM: Artificial Sequence
<220> FEATURE:
<223> OTHER INFORMATION: Synthetic

<400> SEQUENCE: 82

```
Gln Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ala Tyr
            20                  25                  30

Ala Met His Trp Val Arg Gln Ala Pro Gly Lys Gly Leu Glu Trp Val
        35                  40                  45

Ala Val Ile Trp Tyr Asp Gly Ser Asn Lys Asn Tyr Ala Asp Ser Val
    50                  55                  60

Lys Gly Arg Phe Thr Val Ser Arg Asp Asn Ser Lys Asn Thr Leu Tyr
65                  70                  75                  80

Leu Glu Met Asn Ser Leu Arg Ala Glu Asp Thr Ala Val Tyr Tyr Cys
                85                  90                  95

Ala Arg Asp Leu Met Val Gly Val Thr Asn Tyr Trp Gly Gln Gly Thr
            100                 105                 110

Leu Val Thr Val Ser Thr
        115
```

<210> SEQ ID NO 83
<211> LENGTH: 24
<212> TYPE: DNA
<213> ORGANISM: Artificial Sequence
<220> FEATURE:
<223> OTHER INFORMATION: Synthetic

<400> SEQUENCE: 83

```
ggattcacct tcagtgccta tgcc                                              24
```

<210> SEQ ID NO 84
<211> LENGTH: 8
<212> TYPE: PRT
<213> ORGANISM: Artificial Sequence
<220> FEATURE:
<223> OTHER INFORMATION: Synthetic

<400> SEQUENCE: 84

```
Gly Phe Thr Phe Ser Ala Tyr Ala
1               5
```

<210> SEQ ID NO 85
<211> LENGTH: 24
<212> TYPE: DNA
<213> ORGANISM: Artificial Sequence
<220> FEATURE:
<223> OTHER INFORMATION: Synthetic

<400> SEQUENCE: 85

```
atatggtatg atggaagtaa taaa                                              24
```

<210> SEQ ID NO 86
<211> LENGTH: 8

<212> TYPE: PRT
<213> ORGANISM: Artificial Sequence
<220> FEATURE:
<223> OTHER INFORMATION: Synthetic

<400> SEQUENCE: 86

Ile Trp Tyr Asp Gly Ser Asn Lys
1               5

<210> SEQ ID NO 87
<211> LENGTH: 33
<212> TYPE: DNA
<213> ORGANISM: Artificial Sequence
<220> FEATURE:
<223> OTHER INFORMATION: Synthetic

<400> SEQUENCE: 87
gcgagagatc taatggtcgg agttactaac tat                                   33

<210> SEQ ID NO 88
<211> LENGTH: 11
<212> TYPE: PRT
<213> ORGANISM: Artificial Sequence
<220> FEATURE:
<223> OTHER INFORMATION: Synthetic

<400> SEQUENCE: 88

Ala Arg Asp Leu Met Val Gly Val Thr Asn Tyr
1               5                   10

<210> SEQ ID NO 89
<211> LENGTH: 339
<212> TYPE: DNA
<213> ORGANISM: Artificial Sequence
<220> FEATURE:
<223> OTHER INFORMATION: Synthetic

<400> SEQUENCE: 89
gatgttgtga tgactcagtc tccactctcc ctgcccgtcg cccttggaca gccggcctcc       60
atctcctgca ggtctagtca aagcctcgta tacactgatg aaacacccta cttgaattgg      120
tttcaccaga ggccaggcca atctccaagg cgcctaattt ataaggtttc taaccgggac      180
tctggggtcc cagacagatt caccggcagt gggtcaggca ctgatttcac actaaaaatc      240
agcagggtgg aggctgagga tgttggggtc ttttactgca tgcaaggttc acactggcct      300
ccgtacactt ttggccaggg gaccaagctg gagatcaaa                             339

<210> SEQ ID NO 90
<211> LENGTH: 113
<212> TYPE: PRT
<213> ORGANISM: Artificial Sequence
<220> FEATURE:
<223> OTHER INFORMATION: Synthetic

<400> SEQUENCE: 90

Asp Val Val Met Thr Gln Ser Pro Leu Ser Leu Pro Val Ala Leu Gly
1               5                   10                  15

Gln Pro Ala Ser Ile Ser Cys Arg Ser Ser Gln Ser Leu Val Tyr Thr
            20                  25                  30

Asp Gly Asn Thr Tyr Leu Asn Trp Phe His Gln Arg Pro Gly Gln Ser
        35                  40                  45

Pro Arg Arg Leu Ile Tyr Lys Val Ser Asn Arg Asp Ser Gly Val Pro
    50                  55                  60

Asp Arg Phe Thr Gly Ser Gly Ser Gly Thr Asp Phe Thr Leu Lys Ile
 65                  70                  75                  80

Ser Arg Val Glu Ala Glu Asp Val Gly Val Phe Tyr Cys Met Gln Gly
                 85                  90                  95

Ser His Trp Pro Pro Tyr Thr Phe Gly Gln Gly Thr Lys Leu Glu Ile
            100                 105                 110

Lys

<210> SEQ ID NO 91
<211> LENGTH: 33
<212> TYPE: DNA
<213> ORGANISM: Artificial Sequence
<220> FEATURE:
<223> OTHER INFORMATION: Synthetic

<400> SEQUENCE: 91
caaagcctcg tatacactga tggaaacacc tac                              33

<210> SEQ ID NO 92
<211> LENGTH: 11
<212> TYPE: PRT
<213> ORGANISM: Artificial Sequence
<220> FEATURE:
<223> OTHER INFORMATION: Synthetic

<400> SEQUENCE: 92

Gln Ser Leu Val Tyr Thr Asp Gly Asn Thr Tyr
1               5                   10

<210> SEQ ID NO 93
<211> LENGTH: 9
<212> TYPE: DNA
<213> ORGANISM: Artificial Sequence
<220> FEATURE:
<223> OTHER INFORMATION: Synthetic

<400> SEQUENCE: 93 aaggtttct                                                         9

<210> SEQ ID NO 94
<211> LENGTH: 3
<212> TYPE: PRT
<213> ORGANISM: Artificial Sequence
<220> FEATURE:
<223> OTHER INFORMATION: Synthetic

<400> SEQUENCE: 94

Lys Val Ser
1

<210> SEQ ID NO 95
<211> LENGTH: 30
<212> TYPE: DNA
<213> ORGANISM: Artificial Sequence
<220> FEATURE:
<223> OTHER INFORMATION: Synthetic

<400> SEQUENCE: 95
atgcaaggtt cacactggcc tccgtacact                                  30

<210> SEQ ID NO 96
<211> LENGTH: 10
<212> TYPE: PRT
<213> ORGANISM: Artificial Sequence
<220> FEATURE:

<223> OTHER INFORMATION: Synthetic

<400> SEQUENCE: 96

Met Gln Gly Ser His Trp Pro Pro Tyr Thr
1               5                   10

<210> SEQ ID NO 97
<211> LENGTH: 357
<212> TYPE: DNA
<213> ORGANISM: Artificial Sequence
<220> FEATURE:
<223> OTHER INFORMATION: Synthetic

<400> SEQUENCE: 97

```
caggttcagc tacagcagtg gggcgcagga ctgttgaagc ctgcggagac cctgtccctc      60
acctgcgctg tctatggtgg atccttcagt ggtaactact ggagctggat ccgccagtcc     120
ccagggaagg ggttggagtg gattggggaa atcaatcatc gtggaaactc caactacaac     180
ccgtccctca agagtcgagg caccatatca ttagacacgt ccaagaacca gttatccctg     240
aagctgaggt ctgtgaccgc cgcggacacg gccatgtatt attgtgtgag agggggtggg     300
gactactact tcggcatgga cgtctggggc caggggacca cggtcaccgt ctcctca       357
```

<210> SEQ ID NO 98
<211> LENGTH: 119
<212> TYPE: PRT
<213> ORGANISM: Artificial Sequence
<220> FEATURE:
<223> OTHER INFORMATION: Synthetic

<400> SEQUENCE: 98

Gln Val Gln Leu Gln Gln Trp Gly Ala Gly Leu Leu Lys Pro Ala Glu
1               5                   10                  15

Thr Leu Ser Leu Thr Cys Ala Val Tyr Gly Gly Ser Phe Ser Gly Asn
            20                  25                  30

Tyr Trp Ser Trp Ile Arg Gln Ser Pro Gly Lys Gly Leu Glu Trp Ile
        35                  40                  45

Gly Glu Ile Asn His Arg Gly Asn Ser Asn Tyr Asn Pro Ser Leu Lys
    50                  55                  60

Ser Arg Gly Thr Ile Ser Leu Asp Thr Ser Lys Asn Gln Leu Ser Leu
65                  70                  75                  80

Lys Leu Arg Ser Val Thr Ala Ala Asp Thr Ala Met Tyr Tyr Cys Val
                85                  90                  95

Arg Gly Gly Gly Asp Tyr Tyr Phe Gly Met Asp Val Trp Gly Gln Gly
            100                 105                 110

Thr Thr Val Thr Val Ser Ser
        115

<210> SEQ ID NO 99
<211> LENGTH: 24
<212> TYPE: DNA
<213> ORGANISM: Artificial Sequence
<220> FEATURE:
<223> OTHER INFORMATION: Synthetic

<400> SEQUENCE: 99

```
ggtggatcct tcagtggtaa ctac                                             24
```

<210> SEQ ID NO 100
<211> LENGTH: 8
<212> TYPE: PRT

<210> SEQ ID NO 100
<211> LENGTH: 7
<212> TYPE: PRT
<213> ORGANISM: Artificial Sequence
<220> FEATURE:
<223> OTHER INFORMATION: Synthetic

<400> SEQUENCE: 100

Gly Gly Ser Phe Ser Gly Asn Tyr
1               5

<210> SEQ ID NO 101
<211> LENGTH: 21
<212> TYPE: DNA
<213> ORGANISM: Artificial Sequence
<220> FEATURE:
<223> OTHER INFORMATION: Synthetic

<400> SEQUENCE: 101
atcaatcatc gtggaaactc c                                              21

<210> SEQ ID NO 102
<211> LENGTH: 7
<212> TYPE: PRT
<213> ORGANISM: Artificial Sequence
<220> FEATURE:
<223> OTHER INFORMATION: Synthetic

<400> SEQUENCE: 102

Ile Asn His Arg Gly Asn Ser
1               5

<210> SEQ ID NO 103
<211> LENGTH: 39
<212> TYPE: DNA
<213> ORGANISM: Artificial Sequence
<220> FEATURE:
<223> OTHER INFORMATION: Synthetic

<400> SEQUENCE: 103
gtgagagggg gtggggacta ctacttcggc atggacgtc                           39

<210> SEQ ID NO 104
<211> LENGTH: 13
<212> TYPE: PRT
<213> ORGANISM: Artificial Sequence
<220> FEATURE:
<223> OTHER INFORMATION: Synthetic

<400> SEQUENCE: 104

Val Arg Gly Gly Gly Asp Tyr Tyr Phe Gly Met Asp Val
1               5                   10

<210> SEQ ID NO 105
<211> LENGTH: 321
<212> TYPE: DNA
<213> ORGANISM: Artificial Sequence
<220> FEATURE:
<223> OTHER INFORMATION: Synthetic

<400> SEQUENCE: 105
gccatccagt tgacccagtc tccatcctcc ctgtctgcgt ctgtaggaga cagagtcacc    60
atcacttgcc gggcaagtca gggcattgga aatgatttag ctggtatca gctgagacca   120 gggaaagccc ctaaactcct gatctatgct acatccagtt tacaaagtgg ggtcccatca   180
aggttcagcg gcagtggatc tggcacagat tcactctca ccatcagcag cctgcagcct   240
gaagattttg caactattta ctgtctacaa gattacaatt atccgtggac gttcggccaa    300
gggaccaagg tggaaatcaa g                                                    321

<210> SEQ ID NO 106
<211> LENGTH: 107
<212> TYPE: PRT
<213> ORGANISM: Artificial Sequence
<220> FEATURE:
<223> OTHER INFORMATION: Synthetic

<400> SEQUENCE: 106

Ala Ile Gln Leu Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
            20                  25                  30

Leu Gly Trp Tyr Gln Leu Arg Pro Gly Lys Ala Pro Lys Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 107
<211> LENGTH: 18
<212> TYPE: DNA
<213> ORGANISM: Artificial Sequence
<220> FEATURE:
<223> OTHER INFORMATION: Synthetic

<400> SEQUENCE: 107
cagggcattg gaaatgat                                                         18

<210> SEQ ID NO 108
<211> LENGTH: 6
<212> TYPE: PRT
<213> ORGANISM: Artificial Sequence
<220> FEATURE:
<223> OTHER INFORMATION: Synthetic

<400> SEQUENCE: 108

Gln Gly Ile Gly Asn Asp
1               5

<210> SEQ ID NO 109
<211> LENGTH: 9
<212> TYPE: DNA
<213> ORGANISM: Artificial Sequence
<220> FEATURE:
<223> OTHER INFORMATION: Synthetic

<400> SEQUENCE: 109 gctacatcc                                                                    9

<210> SEQ ID NO 110
<211> LENGTH: 3
<212> TYPE: PRT
<213> ORGANISM: Artificial Sequence
<220> FEATURE:
<223> OTHER INFORMATION: Synthetic

<400> SEQUENCE: 110

Ala Thr Ser
1

<210> SEQ ID NO 111
<211> LENGTH: 27
<212> TYPE: DNA
<213> ORGANISM: Artificial Sequence
<220> FEATURE:
<223> OTHER INFORMATION: Synthetic

<400> SEQUENCE: 111
ctacaagatt acaattatcc gtggacg                                           27

<210> SEQ ID NO 112
<211> LENGTH: 9
<212> TYPE: PRT
<213> ORGANISM: Artificial Sequence
<220> FEATURE:
<223> OTHER INFORMATION: Synthetic

<400> SEQUENCE: 112

Leu Gln Asp Tyr Asn Tyr Pro Trp Thr
1               5

<210> SEQ ID NO 113
<211> LENGTH: 357
<212> TYPE: DNA
<213> ORGANISM: Artificial Sequence
<220> FEATURE:
<223> OTHER INFORMATION: Synthetic

<400> SEQUENCE: 113
caggtgcagc tacagcagtg gggcgcagga ctgttgaagc cttcggagac cctgtccctc       60
acctgcgctg tctatggagg gtccttcagt ggttactact ggagctggat ccgccagtcc      120
ccagggaagg ggctggagtg gattggggaa atcaatcata gtggaagcac caactacaac      180
ccgtccctca agagtcgagt caccatatca gtagacacgt ccaagaacca gttctccctg      240
aagttgacct ctgtgaccgc cgcggacacg gctgtatatt tctgtgcgag agggggtggg      300
acctactact acggtatgga cgtttggggc caagggacca cggtcaccgt ctcctca        357

<210> SEQ ID NO 114
<211> LENGTH: 119
<212> TYPE: PRT
<213> ORGANISM: Artificial Sequence
<220> FEATURE:
<223> OTHER INFORMATION: Synthetic

<400> SEQUENCE: 114

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Tyr
                20                  25                  30

Tyr Trp Ser Trp Ile Arg Gln Ser Pro Gly Lys Gly Leu Glu Trp Ile
            35                  40                  45

Gly Glu Ile Asn His Ser Gly Ser Thr Asn Tyr Asn Pro Ser Leu Lys
        50                  55                  60

Ser Arg Val Thr Ile Ser Val Asp Thr Ser Lys Asn Gln Phe Ser Leu
65                  70                  75                  80

Lys Leu Thr Ser Val Thr Ala Ala Asp Thr Ala Val Tyr Phe Cys Ala
                85                  90                  95

```
Arg Gly Gly Gly Thr Tyr Tyr Tyr Gly Met Asp Val Trp Gly Gln Gly
            100                 105                 110
Thr Thr Val Thr Val Ser Ser
        115
```

<210> SEQ ID NO 115
<211> LENGTH: 24
<212> TYPE: DNA
<213> ORGANISM: Artificial Sequence
<220> FEATURE:
<223> OTHER INFORMATION: Synthetic

<400> SEQUENCE: 115
ggagggtcct tcagtggtta ctac                                           24

<210> SEQ ID NO 116
<211> LENGTH: 8
<212> TYPE: PRT
<213> ORGANISM: Artificial Sequence
<220> FEATURE:
<223> OTHER INFORMATION: Synthetic

<400> SEQUENCE: 116

```
Gly Gly Ser Phe Ser Gly Tyr Tyr
1               5
```

<210> SEQ ID NO 117
<211> LENGTH: 21
<212> TYPE: DNA
<213> ORGANISM: Artificial Sequence
<220> FEATURE:
<223> OTHER INFORMATION: Synthetic

<400> SEQUENCE: 117
atcaatcata gtggaagcac c                                              21

<210> SEQ ID NO 118
<211> LENGTH: 7
<212> TYPE: PRT
<213> ORGANISM: Artificial Sequence
<220> FEATURE:
<223> OTHER INFORMATION: Synthetic

<400> SEQUENCE: 118

```
Ile Asn His Ser Gly Ser Thr
1               5
```

<210> SEQ ID NO 119
<211> LENGTH: 39
<212> TYPE: DNA
<213> ORGANISM: Artificial Sequence
<220> FEATURE:
<223> OTHER INFORMATION: Synthetic

<400> SEQUENCE: 119
gcgagagggg gtgggaccta ctactacggt atggacgtt                           39

<210> SEQ ID NO 120
<211> LENGTH: 13
<212> TYPE: PRT
<213> ORGANISM: Artificial Sequence
<220> FEATURE:
<223> OTHER INFORMATION: Synthetic

<400> SEQUENCE: 120

```
Ala Arg Gly Gly Gly Thr Tyr Tyr Tyr Gly Met Asp Val
```

<210> SEQ ID NO 121
<211> LENGTH: 321
<212> TYPE: DNA
<213> ORGANISM: Artificial Sequence
<220> FEATURE:
<223> OTHER INFORMATION: Synthetic

<400> SEQUENCE: 121

```
gccatccaga tgacccagtc tccatcctcc ctgtctgcat ctgtaggaga cagagtcacc    60
atcacttgcc gggcaagtca gggcattgga tatgatttag ctggtatca gcagaaacca   120
gggaaagccc ctaagctcct gatctatgct gcatccagtt tacaaagtgg ggtcccatca   180
aggttcagcg gcagtggatc tggcacagat ttcactctca ccatcagcag cctgcagcct   240
gaagattttg caacttatta ctgtctacag gattacaatt acccgtggac gttcggccaa   300
gggaccaagg tggatatcaa a                                             321
```

<210> SEQ ID NO 122
<211> LENGTH: 107
<212> TYPE: PRT
<213> ORGANISM: Artificial Sequence
<220> FEATURE:
<223> OTHER INFORMATION: Synthetic

<400> SEQUENCE: 122

```
Ala Ile Gln Met Thr Gln Ser Pro Ser Ser Leu Ser Ala Ser Val Gly
1               5                   10                  15
Asp Arg Val Thr Ile Thr Cys Arg Ala Ser Gln Gly Ile Gly Tyr Asp
            20                  25                  30
Leu Gly Trp Tyr Gln Gln Lys Pro Gly Lys Ala Pro Lys Leu Leu Ile
        35                  40                  45
Tyr Ala Ala Ser Ser Leu Gln Ser Gly Val Pro Ser Arg Phe Ser Gly
    50                  55                  60
Ser Gly Ser Gly Thr Asp Phe Thr Leu Thr Ile Ser Ser Leu Gln Pro
65                  70                  75                  80
Glu Asp Phe Ala Thr Tyr Tyr Cys Leu Gln Asp Tyr Asn Tyr Pro Trp
                85                  90                  95
Thr Phe Gly Gln Gly Thr Lys Val Asp Ile Lys
            100                 105
```

<210> SEQ ID NO 123
<211> LENGTH: 18
<212> TYPE: DNA
<213> ORGANISM: Artificial Sequence
<220> FEATURE:
<223> OTHER INFORMATION: Synthetic

<400> SEQUENCE: 123

```
cagggcattg gatatgat                                                  18
```

<210> SEQ ID NO 124
<211> LENGTH: 6
<212> TYPE: PRT
<213> ORGANISM: Artificial Sequence
<220> FEATURE:
<223> OTHER INFORMATION: Synthetic

<400> SEQUENCE: 124

```
Gln Gly Ile Gly Tyr Asp
1               5
```

<210> SEQ ID NO 125
<211> LENGTH: 9
<212> TYPE: DNA
<213> ORGANISM: Artificial Sequence
<220> FEATURE:
<223> OTHER INFORMATION: Synthetic

<400> SEQUENCE: 125 gctgcatcc                                                                 9

<210> SEQ ID NO 126
<211> LENGTH: 3
<212> TYPE: PRT
<213> ORGANISM: Artificial Sequence
<220> FEATURE:
<223> OTHER INFORMATION: Synthetic

<400> SEQUENCE: 126

Ala Ala Ser
1

<210> SEQ ID NO 127
<211> LENGTH: 27
<212> TYPE: DNA
<213> ORGANISM: Artificial Sequence
<220> FEATURE:
<223> OTHER INFORMATION: Synthetic

<400> SEQUENCE: 127
ctacaggatt acaattaccc gtggacg                                            27

<210> SEQ ID NO 128
<211> LENGTH: 9
<212> TYPE: PRT
<213> ORGANISM: Artificial Sequence
<220> FEATURE:
<223> OTHER INFORMATION: Synthetic

<400> SEQUENCE: 128

Leu Gln Asp Tyr Asn Tyr Pro Trp Thr
1               5

<210> SEQ ID NO 129
<211> LENGTH: 357
<212> TYPE: DNA
<213> ORGANISM: Artificial Sequence
<220> FEATURE:
<223> OTHER INFORMATION: Synthetic

<400> SEQUENCE: 129
caggtgcagc tacagcagtg gggcgcagga ctgttgaagc cttcggagac cctgtccctc        60
acctgcgctg tctatggtgg atccttcagt ggtgactact ggagctggat tcgccagtcc       120
ccagggaagg ggctggagtg gattggggaa atcaatcata gtggaagcac caactacaac       180
ccgtccctca agagtcgagt caccatatca atagacacgt ccaagaacca gttctccctg       240
aaactgagct ctgtgaccgc cgcggacacg gctgtgtatt actgtgcgag aggaggcggg       300
gactactact acggtatgga cgtctggggc ctagggacca cggtcaccgt ctcctca         357

<210> SEQ ID NO 130
<211> LENGTH: 119
<212> TYPE: PRT
<213> ORGANISM: Artificial Sequence
<220> FEATURE:

<223> OTHER INFORMATION: Synthetic

<400> SEQUENCE: 130

Gln Val Gln Leu Gln Gln Trp Gly Ala Gly Leu Leu Lys Pro Ser Glu
1               5                   10                  15

Thr Leu Ser Leu Thr Cys Ala Val Tyr Gly Gly Ser Phe Ser Gly Asp
            20                  25                  30

Tyr Trp Ser Trp Ile Arg Gln Ser Pro Gly Lys Gly Leu Glu Trp Ile
        35                  40                  45

Gly Glu Ile Asn His Ser Gly Ser Thr Asn Tyr Asn Pro Ser Leu Lys
    50                  55                  60

Ser Arg Val Thr Ile Ser Ile Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Gly Gly Gly Asp Tyr Tyr Tyr Gly Met Asp Val Trp Gly Leu Gly
            100                 105                 110

Thr Thr Val Thr Val Ser Ser
        115

<210> SEQ ID NO 131
<211> LENGTH: 24
<212> TYPE: DNA
<213> ORGANISM: Artificial Sequence
<220> FEATURE:
<223> OTHER INFORMATION: Synthetic

<400> SEQUENCE: 131
ggtggatcct tcagtggtga ctac                                          24

<210> SEQ ID NO 132
<211> LENGTH: 8
<212> TYPE: PRT
<213> ORGANISM: Artificial Sequence
<220> FEATURE:
<223> OTHER INFORMATION: Synthetic

<400> SEQUENCE: 132

Gly Gly Ser Phe Ser Gly Asp Tyr
1               5

<210> SEQ ID NO 133
<211> LENGTH: 21
<212> TYPE: DNA
<213> ORGANISM: Artificial Sequence
<220> FEATURE:
<223> OTHER INFORMATION: Synthetic

<400> SEQUENCE: 133
atcaatcata gtggaagcac c                                             21

<210> SEQ ID NO 134
<211> LENGTH: 7
<212> TYPE: PRT
<213> ORGANISM: Artificial Sequence
<220> FEATURE:
<223> OTHER INFORMATION: Synthetic

<400> SEQUENCE: 134

Ile Asn His Ser Gly Ser Thr
1               5

```
<210> SEQ ID NO 135
<211> LENGTH: 39
<212> TYPE: DNA
<213> ORGANISM: Artificial Sequence
<220> FEATURE:
<223> OTHER INFORMATION: Synthetic

<400> SEQUENCE: 135
gcgagaggag gcggggacta ctactacggt atggacgtc                                39

<210> SEQ ID NO 136
<211> LENGTH: 13
<212> TYPE: PRT
<213> ORGANISM: Artificial Sequence
<220> FEATURE:
<223> OTHER INFORMATION: Synthetic

<400> SEQUENCE: 136

Ala Arg Gly Gly Gly Asp Tyr Tyr Tyr Gly Met Asp Val
1               5                   10

<210> SEQ ID NO 137
<211> LENGTH: 321
<212> TYPE: DNA
<213> ORGANISM: Artificial Sequence
<220> FEATURE:
<223> OTHER INFORMATION: Synthetic

<400> SEQUENCE: 137
gccatccaga tgacccagtc tccatcctcc ctgtctgcat ctgtaggaga cagagtcacc         60
atcacttgcc gggcaagtca gggcattgga aatgatttag ctggtatca gcagaaacca        120 gggaaagccc ctaacctcct gatctatgct acatccagtt tacaaagtgg ggtcccatca        180
aggttcagcg gcagtggatc tggcacagat ttcactctca ccatcagcag cctgcagcct        240
gaagattttg caacttatta ctgtctacaa gattacaatt acccgtggac gttcggccaa        300
gggaccaagg tggaaatcaa a                                                  321

<210> SEQ ID NO 138
<211> LENGTH: 107
<212> TYPE: PRT
<213> ORGANISM: Artificial Sequence
<220> FEATURE:
<223> OTHER INFORMATION: Synthetic

<400> SEQUENCE: 138

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Gly Asn Asp
            20                  25                  30

Leu Gly Trp Tyr Gln Gln Lys Pro Gly Lys Ala Pro Asn Leu Leu Ile
        35                  40                  45

Tyr Ala Thr Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 139
```

```
<211> LENGTH: 18
<212> TYPE: DNA
<213> ORGANISM: Artificial Sequence
<220> FEATURE:
<223> OTHER INFORMATION: Synthetic

<400> SEQUENCE: 139
cagggcattg gaaatgat                                                    18

<210> SEQ ID NO 140
<211> LENGTH: 6
<212> TYPE: PRT
<213> ORGANISM: Artificial Sequence
<220> FEATURE:
<223> OTHER INFORMATION: Synthetic

<400> SEQUENCE: 140

Gln Gly Ile Gly Asn Asp
1               5

<210> SEQ ID NO 141
<211> LENGTH: 9
<212> TYPE: DNA
<213> ORGANISM: Artificial Sequence
<220> FEATURE:
<223> OTHER INFORMATION: Synthetic

<400> SEQUENCE: 141 gctacatcc                                                               9

<210> SEQ ID NO 142
<211> LENGTH: 3
<212> TYPE: PRT
<213> ORGANISM: Artificial Sequence
<220> FEATURE:
<223> OTHER INFORMATION: Synthetic

<400> SEQUENCE: 142

Ala Thr Ser
1

<210> SEQ ID NO 143
<211> LENGTH: 27
<212> TYPE: DNA
<213> ORGANISM: Artificial Sequence
<220> FEATURE:
<223> OTHER INFORMATION: Synthetic

<400> SEQUENCE: 143
ctacaagatt acaattaccc gtggacg                                          27

<210> SEQ ID NO 144
<211> LENGTH: 9
<212> TYPE: PRT
<213> ORGANISM: Artificial Sequence
<220> FEATURE:
<223> OTHER INFORMATION: Synthetic

<400> SEQUENCE: 144

Leu Gln Asp Tyr Asn Tyr Pro Trp Thr
1               5

<210> SEQ ID NO 145
<211> LENGTH: 3633
<212> TYPE: DNA
<213> ORGANISM: Homo sapiens
```

<400> SEQUENCE: 145

```
atgcgaccct ccgggacggc cggggcagcg ctcctggcgc tgctggctgc gctctgcccg      60
gcgagtcggg ctctggagga aaagaaagtt tgccaaggca cgagtaacaa gctcacgcag     120
ttgggcactt ttgaagatca ttttctcagc ctccagagga tgttcaataa ctgtgaggtg     180
gtccttggga atttggaaat tacctatgtg cagaggaatt atgatctttc cttcttaaag     240
accatccagg aggtggctgg ttatgtcctc attgccctca acacagtgga gcgaattcct     300
ttggaaaacc tgcagatcat cagaggaaat atgtactacg aaaattccta tgccttagca     360
gtcttatcta actatgatgc aaataaaacc ggactgaagg agctgcccat gagaaattta     420
caggaaatcc tgcatggcgc cgtgcggttc agcaacaacc ctgccctgtg caacgtggag     480
agcatccagt ggcgggacat agtcagcagt gactttctca gcaacatgtc gatggacttc     540
cagaaccacc tgggcagctg ccaaaagtgt gatccaagct gtcccaatgg gagctgctgg     600
ggtgcaggag aggagaactg ccagaaactg accaaaatca tctgtgccca gcagtgctcc     660
gggcgctgcc gtggcaagtc ccccagtgac tgctgccaca accagtgtgc tgcaggctgc     720
acaggccccc gggagagcga ctgcctggtc tgccgcaaat ccgagacga agccacgtgc     780
aaggacacct gcccccccact catgctctac aaccccacca cgtaccagat ggatgtgaac     840
cccgagggca aatacagctt tggtgccacc tgcgtgaaga agtgtccccg taattatgtg     900
gtgacagatc acggctcgtg cgtccgagcc tgtggggccg acagctatga gatggaggaa     960
gacggcgtcc gcaagtgtaa gaagtgcgaa gggccttgcc gcaaagtgtg taacggaata    1020
ggtattggtg aatttaaaga ctcactctcc ataaatgcta cgaatattaa cacttcaaa    1080
aactgcacct ccatcagtgg cgatctccac atcctgccgg tggcatttag gggtgactcc    1140
ttcacacata ctcctcctct ggatccacag gaactggata ttctgaaaac cgtaaggaa    1200
atcacagggt ttttgctgat tcaggcttgg cctgaaaaca ggacggacct ccatgccttt    1260
gagaacctag aaatcatacg cggcaggacc aagcaacatg gtcagttttc tcttgcagtc    1320
gtcagcctga acataacatc cttgggatta cgctccctca aggagataag tgatggagat    1380
gtgataattt caggaaacaa aaatttgtgc tatgcaaata caataaactg gaaaaaactg    1440
tttgggacct ccggtcagaa accaaaaatt ataagcaaca gaggtgaaaa cagctgcaag    1500
gccacaggcc aggtctgcca tgccttgtgc tcccccgagg ctgctgtggg cccggagccc    1560
agggactgcg tctcttgccg gaatgtcagc cgaggcaggg aatgcgtgga caagtgcaac    1620
cttctggagg gtgagccaag ggagtttgtg gagaactctg agtgcataca gtgccaccca    1680
gagtgcctgc ctcaggccat gaacatcacc tgcacaggac ggggaccaga caactgtatc    1740
cagtgtgccc actacattga cggccccac tgcgtcaaga cctgcccggc aggagtcatg    1800
ggagaaaaca cacccctggt ctggaagtac gcagacgccg ccatgtgtgt ccacctgtgc    1860
catccaaact gcacctacgg atgcactggg ccaggtcttg aaggctgtcc aacgaatggg    1920
cctaagatcc cgtccatcgc cactgggatg gtgggggccc cctcttgct gctggtggtg    1980
gccctgggga tcggcctctt catgcgaagg cgccacatcg ttcggaagcg cacgctgcgg    2040
aggctgctgc aggagaggga gcttgtggag cctcttacac ccagtggaga agctcccaac    2100
caagctctct tgaggatctt gaaggaaact gaattcaaaa agatcaaagt gctgggctcc    2160
ggtgcgttcg gcacggtgta taagggactc tggatcccag aaggtgagaa agttaaaatt    2220
cccgtcgcta tcaaggaatt aagagaagca acatctccga aagccaacaa ggaaatcctc    2280
gatgaagcct acgtgatggc cagcgtggac aaccccccacg tgtgccgcct gctgggcatc    2340
```

```
tgcctcacct ccaccgtgca gctcatcacg cagctcatgc ccttcggctg cctcctggac    2400
tatgtccggg aacacaaaga caatattggc tcccagtacc tgctcaactg gtgtgtgcag    2460
atcgcaaagg gcatgaacta cttggaggac cgtcgcttgg tgcaccgcga cctggcagcc    2520
aggaacgtac tggtgaaaac accgcagcat gtcaagatca cagattttgg gctggccaaa    2580
ctgctgggtg cggaagagaa agaataccat gcagaaggag gcaaagtgcc tatcaagtgg    2640
atggcattgg aatcaattt t acacagaatc tatacccacc agagtgatgt ctggagctac    2700
ggggtgactg tttgggagtt gatgaccttt ggatccaagc catatgacgg aatccctgcc    2760
agcgagatct cctccatcct ggagaaagga gaacgcctcc ctcagccacc catatgtacc    2820
atcgatgtct acatgatcat ggtcaagtgc tggatgatag acgcagatag tcgcccaaag    2880
ttccgtgagt tgatcatcga attctccaaa atggcccgag accccagcg ctaccttgtc    2940 attcaggggg atgaaagaat gcatttgcca agtcctacag actccaactt ctaccgtgcc    3000
ctgatggatg aagaagacat ggacgacgtg gtggatgccg acgagtacct catcccacag    3060
cagggcttct tcagcagccc ctccacgtca cggactcccc tcctgagctc tctgagtgca    3120
accagcaaca attccaccgt ggcttgcatt gatagaaatg gctgcaaag ctgtcccatc    3180 aaggaagaca gcttcttgca gcgatacagc tcagacccca caggcgcctt gactgaggac    3240
agcatagacg acaccttcct cccagtgcct gaatacataa accagtccgt tcccaaaagg    3300
cccgctggct ctgtgcagaa tcctgtctat cacaatcagc ctctgaaccc cgcgcccagc    3360
agagacccac actaccagga ccccacagc actgcagtgg gcaaccccga gtatctcaac    3420
actgtccagc ccacctgtgt caacagcaca ttcgacagcc ctgcccactg ggcccagaaa    3480
ggcagccacc aaattagcct ggacaaccct gactaccagc aggacttctt tcccaaggaa    3540
gccaagccaa atggcatctt taagggctcc acagctgaaa atgcagaata cctaagggtc    3600
gcgccacaaa gcagtgaatt tattggagca tga                                3633
```

<210> SEQ ID NO 146
<211> LENGTH: 1210
<212> TYPE: PRT
<213> ORGANISM: Homo sapiens

<400> SEQUENCE: 146

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

```
His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
            165                 170                 175

Ser Met Asp Phe Gln Asn His Leu Gly Ser Cys Gln Lys Cys Asp Pro
        180                 185                 190

Ser Cys Pro Asn Gly Ser Cys Trp Gly Ala Gly Glu Glu Asn Cys Gln
    195                 200                 205

Lys Leu Thr Lys Ile Ile Cys Ala Gln Gln Cys Ser Gly Arg Cys Arg
210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
            340                 345                 350

Ala Thr Asn Ile Lys His Phe Lys Asn Cys Thr Ser Ile Ser Gly Asp
        355                 360                 365

Leu His Ile Leu Pro Val Ala Phe Arg Gly Asp Ser Phe Thr His Thr
    370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
            420                 425                 430

His Gly Gln Phe Ser Leu Ala Val Val Ser Leu Asn Ile Thr Ser Leu
        435                 440                 445

Gly Leu Arg Ser Leu Lys Glu Ile Ser Asp Gly Asp Val Ile Ile Ser
    450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
            500                 505                 510

Glu Gly Cys Trp Gly Pro Glu Pro Arg Asp Cys Val Ser Cys Arg Asn
        515                 520                 525

Val Ser Arg Gly Arg Glu Cys Val Asp Lys Cys Asn Leu Leu Glu Gly
    530                 535                 540

Glu Pro Arg Glu Phe Val Glu Asn Ser Glu Cys Ile Gln Cys His Pro
545                 550                 555                 560
```

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
            580                 585                 590

Lys Thr Cys Pro Ala Gly Val Met Gly Glu Asn Asn Thr Leu Val Trp
        595                 600                 605

Lys Tyr Ala Asp Ala Gly His Val Cys His Leu Cys His Pro Asn Cys
    610                 615                 620

Thr Tyr Gly Cys Thr Gly Pro Gly Leu Glu Gly Cys Pro Thr Asn Gly
625                 630                 635                 640

Pro Lys Ile Pro Ser Ile Ala Thr Gly Met Val Gly Ala Leu Leu Leu
                645                 650                 655

Leu Leu Val Val Ala Leu Gly Ile Gly Leu Phe Met Arg Arg Arg His
            660                 665                 670

Ile Val Arg Lys Arg Thr Leu Arg Arg Leu Leu Gln Glu Arg Glu Leu
        675                 680                 685

Val Glu Pro Leu Thr Pro Ser Gly Glu Ala Pro Asn Gln Ala Leu Leu
    690                 695                 700

Arg Ile Leu Lys Glu Thr Glu Phe Lys Lys Ile Lys Val Leu Gly Ser
705                 710                 715                 720

Gly Ala Phe Gly Thr Val Tyr Lys Gly Leu Trp Ile Pro Glu Gly Glu
                725                 730                 735

Lys Val Lys Ile Pro Val Ala Ile Lys Glu Leu Arg Glu Ala Thr Ser
            740                 745                 750

Pro Lys Ala Asn Lys Glu Ile Leu Asp Glu Ala Tyr Val Met Ala Ser
        755                 760                 765

Val Asp Asn Pro His Val Cys Arg Leu Leu Gly Ile Cys Leu Thr Ser
    770                 775                 780

Thr Val Gln Leu Ile Thr Gln Leu Met Pro Phe Gly Cys Leu Leu Asp
785                 790                 795                 800

Tyr Val Arg Glu His Lys Asp Asn Ile Gly Ser Gln Tyr Leu Leu Asn
                805                 810                 815

Trp Cys Val Gln Ile Ala Lys Gly Met Asn Tyr Leu Glu Asp Arg Arg
            820                 825                 830

Leu Val His Arg Asp Leu Ala Ala Arg Asn Val Leu Val Lys Thr Pro
        835                 840                 845

Gln His Val Lys Ile Thr Asp Phe Gly Leu Ala Lys Leu Leu Gly Ala
    850                 855                 860

Glu Glu Lys Glu Tyr His Ala Glu Gly Gly Lys Val Pro Ile Lys Trp
865                 870                 875                 880

Met Ala Leu Glu Ser Ile Leu His Arg Ile Tyr Thr His Gln Ser Asp
                885                 890                 895

Val Trp Ser Tyr Gly Val Thr Val Trp Glu Leu Met Thr Phe Gly Ser
            900                 905                 910

Lys Pro Tyr Asp Gly Ile Pro Ala Ser Glu Ile Ser Ser Ile Leu Glu
        915                 920                 925

Lys Gly Glu Arg Leu Pro Gln Pro Pro Ile Cys Thr Ile Asp Val Tyr
    930                 935                 940

Met Ile Met Val Lys Cys Trp Met Ile Asp Ala Asp Ser Arg Pro Lys
945                 950                 955                 960

Phe Arg Glu Leu Ile Ile Glu Phe Ser Lys Met Ala Arg Asp Pro Gln
                965                 970                 975

Arg Tyr Leu Val Ile Gln Gly Asp Glu Arg Met His Leu Pro Ser Pro

```
                    980             985              990
Thr Asp Ser Asn Phe Tyr Arg Ala Leu Met Asp Glu Glu Asp Met Asp
            995                1000                1005

Asp Val Val Asp Ala Asp Glu Tyr Leu Ile Pro Gln Gln Gly Phe Phe
        1010                1015                1020

Ser Ser Pro Ser Thr Ser Arg Thr Pro Leu Leu Ser Ser Leu Ser Ala
1025                1030                1035                1040

Thr Ser Asn Asn Ser Thr Val Ala Cys Ile Asp Arg Asn Gly Leu Gln
            1045                1050                1055

Ser Cys Pro Ile Lys Glu Asp Ser Phe Leu Gln Arg Tyr Ser Ser Asp
        1060                1065                1070

Pro Thr Gly Ala Leu Thr Glu Asp Ser Ile Asp Asp Thr Phe Leu Pro
            1075                1080                1085

Val Pro Glu Tyr Ile Asn Gln Ser Val Pro Lys Arg Pro Ala Gly Ser
        1090                1095                1100

Val Gln Asn Pro Val Tyr His Asn Gln Pro Leu Asn Pro Ala Pro Ser
1105                1110                1115                1120

Arg Asp Pro His Tyr Gln Asp Pro His Ser Thr Ala Val Gly Asn Pro
            1125                1130                1135

Glu Tyr Leu Asn Thr Val Gln Pro Thr Cys Val Asn Ser Thr Phe Asp
        1140                1145                1150

Ser Pro Ala His Trp Ala Gln Lys Gly Ser His Gln Ile Ser Leu Asp
            1155                1160                1165

Asn Pro Asp Tyr Gln Gln Asp Phe Phe Pro Lys Glu Ala Lys Pro Asn
        1170                1175                1180

Gly Ile Phe Lys Gly Ser Thr Ala Glu Asn Ala Glu Tyr Leu Arg Val
1185                1190                1195                1200

Ala Pro Gln Ser Ser Glu Phe Ile Gly Ala
            1205                1210

<210> SEQ ID NO 147
<211> LENGTH: 943
<212> TYPE: PRT
<213> ORGANISM: Homo sapiens

<400> SEQUENCE: 147

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

Tyr Glu Met Glu Glu Asp Gly Val Arg Lys Cys Lys Lys Cys Glu Gly
50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
        115                 120                 125

Lys Thr Val Lys Glu Ile Thr Gly Phe Leu Leu Ile Gln Ala Trp Pro
    130                 135                 140
```

-continued

```
Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
            165                 170                 175

Asn Ile Thr Ser Leu Gly Leu Arg Ser Leu Lys Glu Ile Ser Asp Gly
        180                 185                 190

Asp Val Ile Ile Ser Gly Asn Lys Asn Leu Cys Tyr Ala Asn Thr Ile
    195                 200                 205

Asn Trp Lys Lys Leu Phe Gly Thr Ser Gly Gln Lys Thr Lys Ile Ile
210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
    290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Thr Gly Met Val
    370                 375                 380

Gly Ala Leu Leu Leu Leu Leu Val Val Ala Leu Gly Ile Gly Leu Phe
385                 390                 395                 400

Met Arg Arg Arg His Ile Val Arg Lys Arg Thr Leu Arg Arg Leu Leu
                405                 410                 415

Gln Glu Arg Glu Leu Val Glu Pro Leu Thr Pro Ser Gly Glu Ala Pro
            420                 425                 430

Asn Gln Ala Leu Leu Arg Ile Leu Lys Glu Thr Glu Phe Lys Lys Ile
        435                 440                 445

Lys Val Leu Gly Ser Gly Ala Phe Gly Thr Val Tyr Lys Gly Leu Trp
    450                 455                 460

Ile Pro Glu Gly Glu Lys Val Lys Ile Pro Val Ala Ile Lys Glu Leu
465                 470                 475                 480

Arg Glu Ala Thr Ser Pro Lys Ala Asn Lys Glu Ile Leu Asp Glu Ala
                485                 490                 495

Tyr Val Met Ala Ser Val Asp Asn Pro His Val Cys Arg Leu Leu Gly
            500                 505                 510

Ile Cys Leu Thr Ser Thr Val Gln Leu Ile Thr Gln Leu Met Pro Phe
        515                 520                 525

Gly Cys Leu Leu Asp Tyr Val Arg Glu His Lys Asp Asn Ile Gly Ser
    530                 535                 540

Gln Tyr Leu Leu Asn Trp Cys Val Gln Ile Ala Lys Gly Met Asn Tyr
545                 550                 555                 560

Leu Glu Asp Arg Arg Leu Val His Arg Asp Leu Ala Ala Arg Asn Val
```

```
                     565                 570                 575

Leu Val Lys Thr Pro Gln His Val Lys Ile Thr Asp Phe Gly Leu Ala
                580                 585                 590

Lys Leu Leu Gly Ala Glu Glu Lys Glu Tyr His Ala Glu Gly Gly Lys
                595                 600                 605

Val Pro Ile Lys Trp Met Ala Leu Glu Ser Ile Leu His Arg Ile Tyr
610                 615                 620

Thr His Gln Ser Asp Val Trp Ser Tyr Gly Val Thr Val Trp Glu Leu
625                 630                 635                 640

Met Thr Phe Gly Ser Lys Pro Tyr Asp Gly Ile Pro Ala Ser Glu Ile
                645                 650                 655

Ser Ser Ile Leu Glu Lys Gly Glu Arg Leu Pro Gln Pro Pro Ile Cys
                660                 665                 670

Thr Ile Asp Val Tyr Met Ile Met Val Lys Cys Trp Met Ile Asp Ala
                675                 680                 685

Asp Ser Arg Pro Lys Phe Arg Glu Leu Ile Ile Glu Phe Ser Lys Met
690                 695                 700

Ala Arg Asp Pro Gln Arg Tyr Leu Val Ile Gln Gly Asp Glu Arg Met
705                 710                 715                 720

His Leu Pro Ser Pro Thr Asp Ser Asn Phe Tyr Arg Ala Leu Met Asp
                725                 730                 735

Glu Glu Asp Met Asp Asp Val Val Asp Ala Asp Glu Tyr Leu Ile Pro
                740                 745                 750

Gln Gln Gly Phe Phe Ser Ser Pro Ser Thr Ser Arg Thr Pro Leu Leu
                755                 760                 765

Ser Ser Leu Ser Ala Thr Ser Asn Asn Ser Thr Val Ala Cys Ile Asp
770                 775                 780

Arg Asn Gly Leu Gln Ser Cys Pro Ile Lys Glu Asp Ser Phe Leu Gln
785                 790                 795                 800

Arg Tyr Ser Ser Asp Pro Thr Gly Ala Leu Thr Glu Asp Ser Ile Asp
                805                 810                 815

Asp Thr Phe Leu Pro Val Pro Glu Tyr Ile Asn Gln Ser Val Pro Lys
                820                 825                 830

Arg Pro Ala Gly Ser Val Gln Asn Pro Val Tyr His Asn Gln Pro Leu
                835                 840                 845

Asn Pro Ala Pro Ser Arg Asp Pro His Tyr Gln Asp Pro His Ser Thr
850                 855                 860

Ala Val Gly Asn Pro Glu Tyr Leu Asn Thr Val Gln Pro Thr Cys Val
865                 870                 875                 880

Asn Ser Thr Phe Asp Ser Pro Ala His Trp Ala Gln Lys Gly Ser His
                885                 890                 895

Gln Ile Ser Leu Asp Asn Pro Asp Tyr Gln Gln Asp Phe Phe Pro Lys
                900                 905                 910

Glu Ala Lys Pro Asn Gly Ile Phe Lys Gly Ser Thr Ala Glu Asn Ala
                915                 920                 925

Glu Tyr Leu Arg Val Ala Pro Gln Ser Ser Glu Phe Ile Gly Ala
                935                 940
```

<210> SEQ ID NO 148
<211> LENGTH: 13
<212> TYPE: PRT
<213> ORGANISM: Artificial Sequence
<220> FEATURE:
<223> OTHER INFORMATION: Synthetic

<400> SEQUENCE: 148

Leu Glu Glu Lys Lys Gly Asn Tyr Val Val Thr Asp His
1               5                   10

<210> SEQ ID NO 149
<211> LENGTH: 19
<212> TYPE: PRT
<213> ORGANISM: Artificial Sequence
<220> FEATURE:
<223> OTHER INFORMATION: Synthetic

<400> SEQUENCE: 149

Leu Glu Glu Lys Lys Gly Asn Tyr Val Val Thr Asp His Gly Gly
1               5                   10                  15

Gly Ser Lys

<210> SEQ ID NO 150
<211> LENGTH: 18
<212> TYPE: PRT
<213> ORGANISM: Artificial Sequence
<220> FEATURE:
<223> OTHER INFORMATION: Synthetic

<400> SEQUENCE: 150

Gly Gly Gly Gly Ser Leu Glu Glu Lys Lys Gly Asn Tyr Val Val Thr
1               5                   10                  15

Asp His

<210> SEQ ID NO 151
<211> LENGTH: 22
<212> TYPE: PRT
<213> ORGANISM: Artificial Sequence
<220> FEATURE:
<223> OTHER INFORMATION: Synthetic

<400> SEQUENCE: 151

Cys Gly Ala Asp Ser Tyr Glu Met Glu Glu Asp Gly Val Arg Lys Cys
1               5                   10                  15

Gly Gly Gly Gly Ser Lys
                20

<210> SEQ ID NO 152
<211> LENGTH: 408
<212> TYPE: PRT
<213> ORGANISM: Artificial Sequence
<220> FEATURE:
<223> OTHER INFORMATION: Synthetic

<400> SEQUENCE: 152

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
                20                  25                  30

Val Val Thr Asp His Gly Ser Cys Val Arg Ala Cys Gly Ala Asp Ser
                35                  40                  45

Tyr Glu Met Glu Glu Asp Gly Val Arg Lys Cys Lys Lys Cys Glu Gly
        50                  55                  60

Pro Cys Arg Lys Val Cys Asn Gly Ile Gly Ile Gly Glu Phe Lys Asp
65                  70                  75                  80

Ser Leu Ser Ile Asn Ala Thr Asn Ile Lys His Phe Lys Asn Cys Thr
                85                  90                  95

Ser Ile Ser Gly Asp Leu His Ile Leu Pro Val Ala Phe Arg Gly Asp
                100                 105                 110

Ser Phe Thr His Thr Pro Leu Asp Pro Gln Glu Leu Asp Ile Leu
            115                 120                 125

Lys Thr Val Lys Glu Ile Thr Gly Phe Leu Leu Ile Gln Ala Trp Pro
    130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
        195                 200                 205

Asn Trp Lys Lys Leu Phe Gly Thr Ser Gly Gln Lys Thr Lys Ile Ile
        210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
        275                 280                 285

Ile Gln Cys His Pro Glu Cys Leu Pro Gln Ala Met Asn Ile Thr Cys
        290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
        355                 360                 365

Cys Pro Thr Asn Gly Pro Lys Ile Pro Ser Ile Ala Glu Gln Lys Leu
    370                 375                 380

Ile Ser Glu Glu Asp Leu Gly Gly Glu Gln Lys Leu Ile Ser Glu Glu
385                 390                 395                 400

Asp Leu His His His His His
                405

<210> SEQ ID NO 153
<211> LENGTH: 613
<212> TYPE: PRT
<213> ORGANISM: Artificial Sequence
<220> FEATURE:
<223> OTHER INFORMATION: Synthetic

<400> SEQUENCE: 153

Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Gly Asn Tyr
            20                  25                  30

Val Val Thr Asp His Gly Ser Cys Val Arg Ala Cys Gly Ala Asp Ser
        35                  40                  45

```
Tyr Glu Met Glu Glu Asp Gly Val Arg Lys Cys Lys Lys Cys Glu Gly
 50                  55                  60

Pro Cys Arg Lys Val Cys Asn Gly Ile Gly Ile Gly Glu Phe Lys Asp
 65                  70                  75                  80

Ser Leu Ser Ile Asn Ala Thr Asn Ile Lys His Phe Lys Asn Cys Thr
                 85                  90                  95

Ser Ile Ser Gly Asp Leu His Ile Leu Pro Val Ala Phe Arg Gly Asp
            100                 105                 110

Ser Phe Thr His Thr Pro Pro Leu Asp Pro Gln Glu Leu Asp Ile Leu
            115                 120                 125

Lys Thr Val Lys Glu Ile Thr Gly Phe Leu Leu Ile Gln Ala Trp Pro
130                 135                 140

Glu Asn Arg Thr Asp Leu His Ala Phe Glu Asn Leu Glu Ile Ile Arg
145                 150                 155                 160

Gly Arg Thr Lys Gln His Gly Gln Phe Ser Leu Ala Val Val Ser Leu
                165                 170                 175

Asn Ile Thr Ser Leu Gly Leu Arg Ser Leu Lys Glu Ile Ser Asp Gly
            180                 185                 190

Asp Val Ile Ile Ser Gly Asn Lys Asn Leu Cys Tyr Ala Asn Thr Ile
            195                 200                 205

Asn Trp Lys Lys Leu Phe Gly Thr Ser Gly Gln Lys Thr Lys Ile Ile
210                 215                 220

Ser Asn Arg Gly Glu Asn Ser Cys Lys Ala Thr Gly Gln Val Cys His
225                 230                 235                 240

Ala Leu Cys Ser Pro Glu Gly Cys Trp Gly Pro Glu Pro Arg Asp Cys
                245                 250                 255

Val Ser Cys Arg Asn Val Ser Arg Gly Arg Glu Cys Val Asp Lys Cys
            260                 265                 270

Asn Leu Leu Glu Gly Glu Pro Arg Glu Phe Val Glu Asn Ser Glu Cys
            275                 280                 285

Ile Gln Cys His Pro Glu Cys Leu Pro Gln Ala Met Asn Ile Thr Cys
            290                 295                 300

Thr Gly Arg Gly Pro Asp Asn Cys Ile Gln Cys Ala His Tyr Ile Asp
305                 310                 315                 320

Gly Pro His Cys Val Lys Thr Cys Pro Ala Gly Val Met Gly Glu Asn
                325                 330                 335

Asn Thr Leu Val Trp Lys Tyr Ala Asp Ala Gly His Val Cys His Leu
            340                 345                 350

Cys His Pro Asn Cys Thr Tyr Gly Cys Thr Gly Pro Gly Leu Glu Gly
            355                 360                 365

Cys Pro Thr Asn Gly Pro Lys Ile Pro Ser Ile Ala Glu Pro Arg Gly
370                 375                 380

Pro Thr Ile Lys Pro Cys Pro Cys Lys Cys Pro Ala Pro Asn Leu
385                 390                 395                 400

Leu Gly Gly Pro Ser Val Phe Ile Phe Pro Pro Lys Ile Lys Asp Val
                405                 410                 415

Leu Met Ile Ser Leu Ser Pro Ile Val Thr Cys Val Val Val Asp Val
            420                 425                 430

Ser Glu Asp Asp Pro Asp Val Gln Ile Ser Trp Phe Val Asn Asn Val
            435                 440                 445

Glu Val His Thr Ala Gln Thr Gln Thr His Arg Glu Asp Tyr Asn Ser
450                 455                 460

Thr Leu Arg Val Val Ser Ala Leu Pro Ile Gln His Gln Asp Trp Met
```

```
                465                 470                 475                 480
        Ser Gly Lys Glu Phe Lys Cys Lys Val Asn Asn Lys Asp Leu Pro Ala
                            485                 490                 495

Pro Ile Glu Arg Thr Ile Ser Lys Pro Lys Gly Ser Val Arg Ala Pro
                        500                 505                 510

Gln Val Tyr Val Leu Pro Pro Glu Glu Met Thr Lys Lys Gln
                        515                 520                 525

Val Thr Leu Thr Cys Met Val Thr Asp Phe Met Pro Glu Asp Ile Tyr
                530                 535                 540

Val Glu Trp Thr Asn Asn Gly Lys Thr Glu Leu Asn Tyr Lys Asn Thr
        545                 550                 555                 560

Glu Pro Val Leu Asp Ser Asp Gly Ser Tyr Phe Met Tyr Ser Lys Leu
                            565                 570                 575

Arg Val Glu Lys Lys Asn Trp Val Glu Arg Asn Ser Tyr Ser Cys Ser
                        580                 585                 590

Val Val His Glu Gly Leu His Asn His His Thr Thr Lys Ser Phe Ser
                        595                 600                 605

Arg Thr Pro Gly Lys
                610

<210> SEQ ID NO 154
<211> LENGTH: 684
<212> TYPE: PRT
<213> ORGANISM: Artificial Sequence
<220> FEATURE:
<223> OTHER INFORMATION: Synthetic

<400> SEQUENCE: 154

Met Arg Pro Ser Gly Thr Ala Gly Ala Ala Leu Leu Ala Leu Leu Ala
        1               5                   10                  15

Ala Leu Cys Pro Ala Ser Arg Ala Leu Glu Glu Lys Lys Val Cys Gln
                        20                  25                  30

Gly Thr Ser Asn Lys Leu Thr Gln Leu Gly Thr Phe Glu Asp His Phe
                    35                  40                  45

Leu Ser Leu Gln Arg Met Phe Asn Asn Cys Glu Val Val Leu Gly Asn
        50                  55                  60

Leu Glu Ile Thr Tyr Val Gln Arg Asn Tyr Asp Leu Ser Phe Leu Lys
        65                  70                  75                  80

Thr Ile Gln Glu Val Ala Gly Tyr Val Leu Ile Ala Leu Asn Thr Val
                        85                  90                  95

Glu Arg Ile Pro Leu Glu Asn Leu Gln Ile Ile Arg Gly Asn Met Tyr
                    100                 105                 110

Tyr Glu Asn Ser Tyr Ala Leu Ala Val Leu Ser Asn Tyr Asp Ala Asn
                    115                 120                 125

Lys Thr Gly Leu Lys Glu Leu Pro Met Arg Asn Leu Gln Glu Ile Leu
                130                 135                 140

His Gly Ala Val Arg Phe Ser Asn Asn Pro Ala Leu Cys Asn Val Glu
        145                 150                 155                 160

Ser Ile Gln Trp Arg Asp Ile Val Ser Ser Asp Phe Leu Ser Asn Met
                        165                 170                 175

Ser Met Asp Phe Gln Asn His Leu Gly Ser Cys Gln Lys Cys Asp Pro
                    180                 185                 190

Ser Cys Pro Asn Gly Ser Cys Trp Gly Ala Gly Glu Glu Asn Cys Gln
                    195                 200                 205

Lys Leu Thr Lys Ile Ile Cys Ala Gln Gln Cys Ser Gly Arg Cys Arg
```

```
            210                 215                 220
Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
                260                 265                 270

Thr Thr Tyr Gln Met Asp Val Asn Pro Glu Gly Lys Tyr Ser Phe Gly
            275                 280                 285

Ala Thr Cys Val Lys Lys Cys Pro Arg Asn Tyr Val Val Thr Asp His
        290                 295                 300

Gly Ser Cys Val Arg Ala Cys Gly Ala Asp Ser Tyr Glu Met Glu Glu
305                 310                 315                 320

Asp Gly Val Arg Lys Cys Lys Lys Cys Glu Gly Pro Cys Arg Lys Val
                325                 330                 335

Cys Asn Gly Ile Gly Ile Gly Glu Phe Lys Asp Ser Leu Ser Ile Asn
                340                 345                 350

Ala Thr Asn Ile Lys His Phe Lys Asn Cys Thr Ser Ile Ser Gly Asp
            355                 360                 365

Leu His Ile Leu Pro Val Ala Phe Arg Gly Asp Ser Phe Thr His Thr
        370                 375                 380

Pro Pro Leu Asp Pro Gln Glu Leu Asp Ile Leu Lys Thr Val Lys Glu
385                 390                 395                 400

Ile Thr Gly Phe Leu Leu Ile Gln Ala Trp Pro Glu Asn Arg Thr Asp
                405                 410                 415

Leu His Ala Phe Glu Asn Leu Glu Ile Ile Arg Gly Arg Thr Lys Gln
                420                 425                 430

His Gly Gln Phe Ser Leu Ala Val Val Ser Leu Asn Ile Thr Ser Leu
            435                 440                 445

Gly Leu Arg Ser Leu Lys Glu Ile Ser Asp Gly Asp Val Ile Ile Ser
450                 455                 460

Gly Asn Lys Asn Leu Cys Tyr Ala Asn Thr Ile Asn Trp Lys Lys Leu
465                 470                 475                 480

Phe Gly Thr Ser Gly Gln Lys Thr Lys Ile Ile Ser Asn Arg Gly Glu
                485                 490                 495

Asn Ser Cys Lys Ala Thr Gly Gln Val Cys His Ala Leu Cys Ser Pro
                500                 505                 510

Glu Gly Cys Trp Gly Pro Glu Pro Arg Asp Cys Val Ser Cys Arg Asn
                515                 520                 525

Val Ser Arg Gly Arg Glu Cys Val Asp Lys Cys Asn Leu Leu Glu Gly
            530                 535                 540

Glu Pro Arg Glu Phe Val Glu Asn Ser Glu Cys Ile Gln Cys His Pro
545                 550                 555                 560

Glu Cys Leu Pro Gln Ala Met Asn Ile Thr Cys Thr Gly Arg Gly Pro
                565                 570                 575

Asp Asn Cys Ile Gln Cys Ala His Tyr Ile Asp Gly Pro His Cys Val
                580                 585                 590

Lys Thr Cys Pro Ala Gly Val Met Gly Glu Asn Asn Thr Leu Val Trp
            595                 600                 605

Lys Tyr Ala Asp Ala Gly His Val Cys His Leu Cys His Pro Asn Cys
        610                 615                 620

Thr Tyr Gly Cys Thr Gly Pro Gly Leu Glu Gly Cys Pro Thr Asn Gly
625                 630                 635                 640
```

-continued

```
Pro Lys Ile Pro Ser Ile Ala Cys Pro Gly Gly Glu Gln Lys Leu Ile
                645                 650                 655

Ser Glu Glu Asp Leu Gly Gly Glu Gln Lys Leu Ile Ser Glu Glu Asp
            660                 665                 670

Leu Ser Gly His His His His His His Ser Ser Gly
        675                 680
```

<210> SEQ ID NO 155
<211> LENGTH: 880
<212> TYPE: PRT
<213> ORGANISM: Artificial Sequence
<220> FEATURE:
<223> OTHER INFORMATION: Synthetic

<400> SEQUENCE: 155

```
Met Arg Pro Ser Gly Thr Ala Gly Ala Ala Leu Leu Ala Leu Leu Ala
1               5                   10                  15

Ala Leu Cys Pro Ala Ser Arg Ala Leu Glu Glu Lys Lys Val Cys Gln
            20                  25                  30

Gly Thr Ser Asn Lys Leu Thr Gln Leu Gly Thr Phe Glu Asp His Phe
        35                  40                  45

Leu Ser Leu Gln Arg Met Phe Asn Asn Cys Glu Val Val Leu Gly Asn
    50                  55                  60

Leu Glu Ile Thr Tyr Val Gln Arg Asn Tyr Asp Leu Ser Phe Leu Lys
65                  70                  75                  80

Thr Ile Gln Glu Val Ala Gly Tyr Val Leu Ile Ala Leu Asn Thr Val
                85                  90                  95

Glu Arg Ile Pro Leu Glu Asn Leu Gln Ile Ile Arg Gly Asn Met Tyr
            100                 105                 110

Tyr Glu Asn Ser Tyr Ala Leu Ala Val Leu Ser Asn Tyr Asp Ala Asn
        115                 120                 125

Lys Thr Gly Leu Lys Glu Leu Pro Met Arg Asn Leu Gln Glu Ile Leu
    130                 135                 140

His Gly Ala Val Arg Phe Ser Asn Asn Pro Ala Leu Cys Asn Val Glu
145                 150                 155                 160

Ser Ile Gln Trp Arg Asp Ile Val Ser Ser Asp Phe Leu Ser Asn Met
                165                 170                 175

Ser Met Asp Phe Gln Asn His Leu Gly Ser Cys Gln Lys Cys Asp Pro
            180                 185                 190

Ser Cys Pro Asn Gly Ser Cys Trp Gly Ala Gly Glu Glu Asn Cys Gln
        195                 200                 205

Lys Leu Thr Lys Ile Ile Cys Ala Gln Gln Cys Ser Gly Arg Cys Arg
    210                 215                 220

Gly Lys Ser Pro Ser Asp Cys Cys His Asn Gln Cys Ala Ala Gly Cys
225                 230                 235                 240

Thr Gly Pro Arg Glu Ser Asp Cys Leu Val Cys Arg Lys Phe Arg Asp
                245                 250                 255

Glu Ala Thr Cys Lys Asp Thr Cys Pro Pro Leu Met Leu Tyr Asn Pro
            260                 265                 270

Thr Thr Tyr Gln Met Asp Val Asn Pro Glu Gly Lys Tyr Ser Phe Gly
        275                 280                 285

Ala Thr Cys Val Lys Lys Cys Pro Arg Asn Tyr Val Val Thr Asp His
    290                 295                 300

Gly Ser Cys Val Arg Ala Cys Gly Ala Asp Ser Tyr Glu Met Glu Glu
305                 310                 315                 320
```

-continued

```
Asp Gly Val Arg Lys Cys Lys Cys Glu Gly Pro Cys Arg Lys Val
            325                 330                 335
Cys Asn Gly Ile Gly Ile Gly Glu Phe Lys Asp Ser Leu Ser Ile Asn
            340                 345                 350
Ala Thr Asn Ile Lys His Phe Lys Asn Cys Thr Ser Ile Ser Gly Asp
            355                 360                 365
Leu His Ile Leu Pro Val Ala Phe Arg Gly Asp Ser Phe Thr His Thr
    370                 375                 380
Pro Pro Leu Asp Pro Gln Glu Leu Asp Ile Leu Lys Thr Val Lys Glu
385                 390                 395                 400
Ile Thr Gly Phe Leu Leu Ile Gln Ala Trp Pro Glu Asn Arg Thr Asp
            405                 410                 415
Leu His Ala Phe Glu Asn Leu Glu Ile Ile Arg Gly Arg Thr Lys Gln
            420                 425                 430
His Gly Gln Phe Ser Leu Ala Val Val Ser Leu Asn Ile Thr Ser Leu
        435                 440                 445
Gly Leu Arg Ser Leu Lys Glu Ile Ser Asp Gly Asp Val Ile Ile Ser
    450                 455                 460
Gly Asn Lys Asn Leu Cys Tyr Ala Asn Thr Ile Asn Trp Lys Lys Leu
465                 470                 475                 480
Phe Gly Thr Ser Gly Gln Lys Thr Lys Ile Ile Ser Asn Arg Gly Glu
            485                 490                 495
Asn Ser Cys Lys Ala Thr Gly Gln Val Cys His Ala Leu Cys Ser Pro
            500                 505                 510
Glu Gly Cys Trp Gly Pro Glu Pro Arg Asp Cys Val Ser Cys Arg Asn
            515                 520                 525
Val Ser Arg Gly Arg Glu Cys Val Asp Lys Cys Asn Leu Leu Glu Gly
        530                 535                 540
Glu Pro Arg Glu Phe Val Glu Asn Ser Glu Cys Ile Gln Cys His Pro
545                 550                 555                 560
Glu Cys Leu Pro Gln Ala Met Asn Ile Thr Cys Thr Gly Arg Gly Pro
            565                 570                 575
Asp Asn Cys Ile Gln Cys Ala His Tyr Ile Asp Gly Pro His Cys Val
            580                 585                 590
Lys Thr Cys Pro Ala Gly Val Met Gly Glu Asn Asn Thr Leu Val Trp
            595                 600                 605
Lys Tyr Ala Asp Ala Gly His Val Cys His Leu Cys His Pro Asn Cys
    610                 615                 620
Thr Tyr Gly Cys Thr Gly Pro Gly Leu Glu Gly Cys Pro Thr Asn Gly
625                 630                 635                 640
Pro Lys Ile Pro Ser Ile Ala Glu Pro Arg Gly Pro Thr Ile Lys Pro
            645                 650                 655
Cys Pro Pro Cys Lys Cys Pro Ala Pro Asn Leu Leu Gly Gly Pro Ser
            660                 665                 670
Val Phe Ile Phe Pro Pro Lys Ile Lys Asp Val Leu Met Ile Ser Leu
        675                 680                 685
Ser Pro Ile Val Thr Cys Val Val Val Asp Val Ser Glu Asp Asp Pro
    690                 695                 700
Asp Val Gln Ile Ser Trp Phe Val Asn Asn Val Glu Val His Thr Ala
705                 710                 715                 720
Gln Thr Gln Thr His Arg Glu Asp Tyr Asn Ser Thr Leu Arg Val Val
            725                 730                 735
```

```
Ser Ala Leu Pro Ile Gln His Gln Asp Trp Met Ser Gly Lys Glu Phe
            740                 745                 750

Lys Cys Lys Val Asn Asn Lys Asp Leu Pro Ala Pro Ile Glu Arg Thr
        755                 760                 765

Ile Ser Lys Pro Lys Gly Ser Val Arg Ala Pro Gln Val Tyr Val Leu
    770                 775                 780

Pro Pro Pro Glu Glu Glu Met Thr Lys Lys Gln Val Thr Leu Thr Cys
785                 790                 795                 800

Met Val Thr Asp Phe Met Pro Glu Asp Ile Tyr Val Glu Trp Thr Asn
                805                 810                 815

Asn Gly Lys Thr Glu Leu Asn Tyr Lys Asn Thr Glu Pro Val Leu Asp
        820                 825                 830

Ser Asp Gly Ser Tyr Phe Met Tyr Ser Lys Leu Arg Val Glu Lys Lys
            835                 840                 845

Asn Trp Val Glu Arg Asn Ser Tyr Ser Cys Ser Val Val His Glu Gly
850                 855                 860

Leu His Asn His His Thr Thr Lys Ser Phe Ser Arg Thr Pro Gly Lys
865                 870                 875                 880

<210> SEQ ID NO 156
<211> LENGTH: 330
<212> TYPE: PRT
<213> ORGANISM: Artificial Sequence
<220> FEATURE:
<223> OTHER INFORMATION: Synthetic

<400> SEQUENCE: 156

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220
```

```
Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
            245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
            325                 330

<210> SEQ ID NO 157
<211> LENGTH: 327
<212> TYPE: PRT
<213> ORGANISM: Artificial Sequence
<220> FEATURE:
<223> OTHER INFORMATION: Synthetic

<400> SEQUENCE: 157

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255
```

```
Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
        290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 158
<211> LENGTH: 327
<212> TYPE: PRT
<213> ORGANISM: Artificial Sequence
<220> FEATURE:
<223> OTHER INFORMATION: Synthetic

<400> SEQUENCE: 158

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Leu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
    130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
        195                 200                 205

Pro Ser Ser Ile Glu Lys Thr Ile Ser Lys Ala Lys Gly Gln Pro Arg
    210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
        275                 280                 285
```

Arg Leu Thr Val Asp Lys Ser Arg Trp Gln Glu Gly Asn Val Phe Ser
    290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 159
<211> LENGTH: 19
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala
<220> FEATURE:
<221> NAME/KEY: VARIANT
<222> LOCATION: (2)...(2)
<223> OTHER INFORMATION: Xaa = Arg or Lys
<220> FEATURE:
<221> NAME/KEY: VARIANT
<222> LOCATION: (3)...(3)
<223> OTHER INFORMATION: Xaa = Gly or Asp
<220> FEATURE:
<221> NAME/KEY: VARIANT
<222> LOCATION: (4)...(4)
<223> OTHER INFORMATION: Xaa = Asp, Gly, Ile or absent
<220> FEATURE:
<221> NAME/KEY: VARIANT
<222> LOCATION: (5)...(5)
<223> OTHER INFORMATION: Xaa = Tyr, Leu, His or absent
<220> FEATURE:
<221> NAME/KEY: VARIANT
<222> LOCATION: (6)...(6)
<223> OTHER INFORMATION: Xaa = Val, Glu, Asp, Met or absent
<220> FEATURE:
<221> NAME/KEY: VARIANT
<222> LOCATION: (7)...(7)
<223> OTHER INFORMATION: Xaa = Trp, Ile, Tyr, Val or absent
<220> FEATURE:
<221> NAME/KEY: VARIANT
<222> LOCATION: (8)...(8)
<223> OTHER INFORMATION: Xaa = Gly or Arg
<220> FEATURE:
<221> NAME/KEY: VARIANT
<222> LOCATION: (9)...(9)
<223> OTHER INFORMATION: Xaa = Thr, Asp, Lys, Gly or Val
<220> FEATURE:
<221> NAME/KEY: VARIANT
<222> LOCATION: (10)...(10)
<223> OTHER INFORMATION: Xaa = His, Asp, Thr or absent
<220> FEATURE:
<221> NAME/KEY: VARIANT
<222> LOCATION: (11)...(11)
<223> OTHER INFORMATION: Xaa = Tyr or absent
<220> FEATURE:
<221> NAME/KEY: VARIANT
<222> LOCATION: (12)...(12)
<223> OTHER INFORMATION: Xaa = Tyr or absent
<220> FEATURE:
<221> NAME/KEY: VARIANT
<222> LOCATION: (13)...(13)
<223> OTHER INFORMATION: Xaa = Tyr or Asn
<220> FEATURE:
<221> NAME/KEY: VARIANT
<222> LOCATION: (14)...(14)
<223> OTHER INFORMATION: Xaa = Arg or Tyr
<220> FEATURE:
<221> NAME/KEY: VARIANT
<222> LOCATION: (15)...(15)
<223> OTHER INFORMATION: Xaa = Pro, Tyr or absent
<220> FEATURE:
<221> NAME/KEY: VARIANT
<222> LOCATION: (16)...(16)

-continued

```
<223> OTHER INFORMATION: Xaa = Leu, Gly or absent
<220> FEATURE:
<221> NAME/KEY: VARIANT
<222> LOCATION: (17)...(17)
<223> OTHER INFORMATION: Xaa = Phe, Met or absent
<220> FEATURE:
<221> NAME/KEY: VARIANT
<222> LOCATION: (18)...(18)
<223> OTHER INFORMATION: Xaa = Asp or absent
<220> FEATURE:
<221> NAME/KEY: VARIANT
<222> LOCATION: (19)...(19)
<223> OTHER INFORMATION: Xaa = Tyr, Val or absent

<400> SEQUENCE: 159

Xaa Xaa Xaa Xaa Xaa Xaa Xaa Xaa Xaa Xaa Xaa Xaa Xaa Xaa Xaa Xaa
1               5                   10                  15

Xaa Xaa Xaa

<210> SEQ ID NO 160
<211> LENGTH: 10
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln, Leu or Met
<220> FEATURE:
<221> NAME/KEY: VARIANT
<222> LOCATION: (2)...(2)
<223> OTHER INFORMATION: Xaa = Gln
<220> FEATURE:
<221> NAME/KEY: VARIANT
<222> LOCATION: (3)...(3)
<223> OTHER INFORMATION: Xaa = Leu, Tyr, Asp or Gly
<220> FEATURE:
<221> NAME/KEY: VARIANT
<222> LOCATION: (4)...(4)
<223> OTHER INFORMATION: Xaa = Asn, Asp, Tyr or Ser
<220> FEATURE:
<221> NAME/KEY: VARIANT
<222> LOCATION: (5)...(5)
<223> OTHER INFORMATION: Xaa = Ser, Arg, Asn or His
<220> FEATURE:
<221> NAME/KEY: VARIANT
<222> LOCATION: (6)...(6)
<223> OTHER INFORMATION: Xaa = Tyr, Ser or Trp
<220> FEATURE:
<221> NAME/KEY: VARIANT
<222> LOCATION: (7)...(7)
<223> OTHER INFORMATION: Xaa = Pro or Ser
<220> FEATURE:
<221> NAME/KEY: VARIANT
<222> LOCATION: (8)...(8)
<223> OTHER INFORMATION: Xaa = Pro or absent
<220> FEATURE:
<221> NAME/KEY: VARIANT
<222> LOCATION: (9)...(9)
<223> OTHER INFORMATION: Xaa = Leu, Arg, Ile, Trp or Tyr
<220> FEATURE:
<221> NAME/KEY: VARIANT
<222> LOCATION: (10)...(10)
<223> OTHER INFORMATION: Xaa = Thr

<400> SEQUENCE: 160

Xaa Xaa Xaa Xaa Xaa Xaa Xaa Xaa Xaa Xaa
1               5                   10

<210> SEQ ID NO 161
<211> LENGTH: 8
<212> TYPE: PRT
<213> ORGANISM: Artificial Sequence
```

```
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gly
<220> FEATURE:
<221> NAME/KEY: VARIANT
<222> LOCATION: (2)...(2)
<223> OTHER INFORMATION: Xaa = Phe or Gly
<220> FEATURE:
<221> NAME/KEY: VARIANT
<222> LOCATION: (3)...(3)
<223> OTHER INFORMATION: Xaa = Pro, Thr or Ser
<220> FEATURE:
<221> NAME/KEY: VARIANT
<222> LOCATION: (4)...(4)
<223> OTHER INFORMATION: Xaa = Phe
<220> FEATURE:
<221> NAME/KEY: VARIANT
<222> LOCATION: (5)...(5)
<223> OTHER INFORMATION: Xaa = Ser or Asp
<220> FEATURE:
<221> NAME/KEY: VARIANT
<222> LOCATION: (6)...(6)
<223> OTHER INFORMATION: Xaa = Ser, Arg, Asp, Gly or Ala
<220> FEATURE:
<221> NAME/KEY: VARIANT
<222> LOCATION: (7)...(7)
<223> OTHER INFORMATION: Xaa = Tyr or Asp
<220> FEATURE:
<221> NAME/KEY: VARIANT
<222> LOCATION: (8)...(8)
<223> OTHER INFORMATION: Xaa = Asp, Gly, Ala or Tyr

<400> SEQUENCE: 161

Xaa Xaa Xaa Xaa Xaa Xaa Xaa Xaa
1               5

<210> SEQ ID NO 162
<211> LENGTH: 8
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ile
<220> FEATURE:
<221> NAME/KEY: VARIANT
<222> LOCATION: (2)...(2)
<223> OTHER INFORMATION: Xaa = Gly, Trp, Ser or Asn
<220> FEATURE:
<221> NAME/KEY: VARIANT
<222> LOCATION: (3)...(3)
<223> OTHER INFORMATION: Xaa = His, Trp, Tyr or absent
<220> FEATURE:
<221> NAME/KEY: VARIANT
<222> LOCATION: (4)...(4)
<223> OTHER INFORMATION: Xaa = Thr, Asp, Asn or His
<220> FEATURE:
<221> NAME/KEY: VARIANT
<222> LOCATION: (5)...(5)
<223> OTHER INFORMATION: Xaa = Ala, Gly or Ser
<220> FEATURE:
<221> NAME/KEY: VARIANT
<222> LOCATION: (6)...(6)
<223> OTHER INFORMATION: Xaa = Gly or Ser
<220> FEATURE:
<221> NAME/KEY: VARIANT
<222> LOCATION: (7)...(7)
<223> OTHER INFORMATION: Xaa = Ala, Asn or Ser
<220> FEATURE:
<221> NAME/KEY: VARIANT
<222> LOCATION: (8)...(8)
<223> OTHER INFORMATION: Xaa = Thr, Lys or Ile
```

<400> SEQUENCE: 162

Xaa Xaa Xaa Xaa Xaa Xaa Xaa Xaa
1               5

<210> SEQ ID NO 163
<211> LENGTH: 11
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Gln
<220> FEATURE:
<221> NAME/KEY: VARIANT
<222> LOCATION: (2)...(2)
<223> OTHER INFORMATION: Xaa = Gly or Ser
<220> FEATURE:
<221> NAME/KEY: VARIANT
<222> LOCATION: (3)...(3)
<223> OTHER INFORMATION: Xaa = Ile, Thr, Val or Leu
<220> FEATURE:
<221> NAME/KEY: VARIANT
<222> LOCATION: (4)...(4)
<223> OTHER INFORMATION: Xaa = Asn, Ser, Gly or Val
<220> FEATURE:
<221> NAME/KEY: VARIANT
<222> LOCATION: (5)...(5)
<223> OTHER INFORMATION: Xaa = Asn, Ser or Tyr
<220> FEATURE:
<221> NAME/KEY: VARIANT
<222> LOCATION: (6)...(6)
<223> OTHER INFORMATION: Xaa = Thr or absent
<220> FEATURE:
<221> NAME/KEY: VARIANT
<222> LOCATION: (7)...(7)
<223> OTHER INFORMATION: Xaa = Asp or absent
<220> FEATURE:
<221> NAME/KEY: VARIANT
<222> LOCATION: (8)...(8)
<223> OTHER INFORMATION: Xaa = Gly or absent
<220> FEATURE:
<221> NAME/KEY: VARIANT
<222> LOCATION: (9)...(9)
<223> OTHER INFORMATION: Xaa = Asn or absent
<220> FEATURE:
<221> NAME/KEY: VARIANT
<222> LOCATION: (10)...(10)
<223> OTHER INFORMATION: Xaa = Thr or absent
<220> FEATURE:
<221> NAME/KEY: VARIANT
<222> LOCATION: (11)...(11)
<223> OTHER INFORMATION: Xaa = Tyr, Trp or Asp

<400> SEQUENCE: 163

Xaa Xaa Xaa Xaa Xaa Xaa Xaa Xaa Xaa Xaa Xaa
1               5                   10

<210> SEQ ID NO 164
<211> LENGTH: 3
<212> TYPE: PRT
<213> ORGANISM: Artificial Sequence
<220> FEATURE:
<223> OTHER INFORMATION: Synthetic
<220> FEATURE:
<221> NAME/KEY: VARIANT
<222> LOCATION: (1)...(1)
<223> OTHER INFORMATION: Xaa = Ala, Lys or Gly
<220> FEATURE:
<221> NAME/KEY: VARIANT
<222> LOCATION: (2)...(2)
<223> OTHER INFORMATION: Xaa = Ala, Thr or Val
<220> FEATURE:

-continued

```
<221> NAME/KEY: VARIANT
<222> LOCATION: (3)...(3)
<223> OTHER INFORMATION: Xaa = Ser

<400> SEQUENCE: 164

Xaa Xaa Xaa
1

<210> SEQ ID NO 165
<211> LENGTH: 16
<212> TYPE: PRT
<213> ORGANISM: Artificial Sequence
<220> FEATURE:
<223> OTHER INFORMATION: Synthetic

<400> SEQUENCE: 165

Cys Gly Ala Asp Ser Tyr Glu Met Glu Glu Asp Gly Val Arg Lys Cys
1               5                   10                  15
```

ANTI-EGFRVIII ANTIBODIES AND USES THEREOF

CROSS-REFERENCE TO RELATED APPLICATIONS

This application is a continuation of U.S. patent application Ser. No. 16/033,477, filed Jul. 12, 2018, which is a continuation of U.S. patent application Ser. No. 15/170,628, filed Jun. 1, 2016, now U.S. Pat. No. 10,047,160, issued Aug. 14, 2018, which is a divisional of U.S. patent application Ser. No. 14/643,886, filed Mar. 10, 2015, now U.S. Pat. No. 9,475,875, issued Oct. 25, 2016, which claims the benefit under 35 U.S.C. § 119(e) of U.S. Provisional Application No. 61/950,963, filed on Mar. 11, 2014, the disclosure of which is herein incorporated by reference in its entirety.

SEQUENCE LISTING

A Sequence Listing in the form of a text file entitled, "2015_03_10_A0020US01_Sequence_List_as_Filed_Text," created Apr. 12, 2018, (size 110,592 bytes) is incorporated herein by reference in its entirety.

FIELD OF THE INVENTION

The present invention relates to human antibodies and antigen-binding fragments of human antibodies that specifically bind the deletion mutants of human epidermal growth factor receptor (EGFR), in particular, the class III deletion mutant, EGFRvIII, and therapeutic and diagnostic methods of using those antibodies.

BACKGROUND

Overexpression and/or gene amplification of the epidermal growth factor (EGF) receptor, or EGFR, have been reported in multiple human tumors, including those in breast, ovarian, bladder, brain, and various squamous carcinomas (Wong, A. J. et al., 1987, *Proc. Natl. Acad. Sci. USA*, 84:6899-6903; Harris et al., 1992, *Natl. Cancer Inst. Monogr.* 11:181-187). However, targeting the EGFR as an anti-neoplastic therapeutic method has been problematic as many normal tissues also express this receptor and may get targeted along with the neoplastic targets. Meanwhile, it has been reported that many glioblastomas having EGFR gene amplification frequently contain gene rearrangement (Ekstrand, A. J. et al., 1992, *Proc. Natl. Acad. Sci. USA*, 89:4309-4313; Wong A. J. et al., 1992, *Proc. Natl. Acad. Sci. USA*, 89:2965-2969). In one study, 17 out of 44 glioblastomas were found to have one or more alterations in the EGFR coding sequence and all of these cases contained amplified EGFR, while none of the 22 cases without gene amplification showed any tumor-specific sequence abnormalities (Frederick, L. et al., 2000, *Cancer Res* 60:1383-1387). The same study also showed that multiple types of EGFR mutations could be detected in individual tumors.

The class III variant of the EGFR (EGFRvIII) is the most frequently found EGFR variant in glioblastoma (Bigner et al., 1990, *Cancer Res* 50:8017-8022; Humphrey et al., 1990, *Proc Natl Acad Sci USA* 87:4207-4211; Yamazaki et al., 1990, *Jap J Cancer Res* 81:773-779; Ekstrand et al., 1992, *Proc Natl Acad Sci USA* 89:4309-4313; Wikstrand et al., 1995, *Cancer Res* 55:3140-3148; and Frederick et al., 2000, *Cancer Res* 60:1383-1387). EGFRvIII is characterized by a deletion of exons 2-7 of the EGFR gene, resulting in an in-frame deletion of 801 base pairs of the coding region, i.e., deletion of 6-273 amino acid residues (based on the residue numbers of mature EGFR), as well as the generation of a new glycine at the fusion junction (Humphrey et al., 1988, *Cancer Res* 48:2231-2238; Yamazaki et al., 1990, supra). EGFRvIII has been shown to have a ligand-independent, weak but constitutively active kinase activity as well as enhanced tumorigenicity (Nishikawa et al., 1994, *Proc Natl Acad Sci USA* 91:7727-7731; and Batra et al., 1995, *Cell Growth and Differentiation* 6:1251-1259). In addition to gliomas, EGFRvIII has been detected in ductal and intraductal breast carcinoma (Wikstrand et al., 1995, *Cancer Res* 55:3140-3148), non-small cell lung carcinomas (Garcia de Palazzo et al., 1993, *Cancer Res* 53:3217-3220), ovarian carcinomas (Moscatello et al., 1995, *Cancer Res* 55:5536-5539), prostate cancer (Olapade-Olaopa et al., 2000, *British J Cancer* 82:186-194), and squamous cell carcinoma of the head and neck (Tinhofer et al., 2011, *Clin Cancer Res* 17(15):5197-5204). In contrast, these and other studies report that normal tissues do not express EGFRvIII (Garcia de Palazzo et al., 1993, supra; Wikstrand et al., 1995, supra; and Wikstrand et al., 1998, *J Neuro Virol* 4:148-158). The highly tumor-specific nature of EGFRvIII makes it an especially useful target for treating cancers and tumors that express this molecule.

The nucleic acid and amino acid sequences of human EGFR are shown in SEQ ID NOs: 145 and 146, respectively, and the amino acid sequence of EGFRvIII is shown in SEQ ID NO:147. Antibodies to EGFRvIII are described in, for example, U.S. Pat. Nos. 5,212,290, 7,736,644, 7,589,180 and 7,767,792.

BRIEF SUMMARY OF THE INVENTION

The present invention provides antibodies and antigen-binding fragments thereof that bind EGFRvIII. The antibodies of the invention are useful, inter alia, for targeting tumor cells that express EGFRvIII. The anti-EGFRvIII antibodies of the invention, and antigen-binding portions thereof, may be used alone in unmodified form, or may be included as part of an antibody-drug conjugate or a bispecific antibody.

The antibodies of the invention can be full-length (for example, an IgG1 or IgG4 antibody) or may comprise only an antigen-binding portion (for example, a Fab, F(ab')$_2$ or scFv fragment), and may be modified to affect functionality, e.g., to eliminate residual effector functions (Reddy et al., 2000, *J. Immunol.* 164:1925-1933).

Exemplary anti-EGFRvIII antibodies of the present invention are listed in Tables 1 and 2 herein. Table 1 sets forth the amino acid sequence identifiers of the heavy chain variable regions (HCVRs), light chain variable regions (LCVRs), heavy chain complementarity determining regions (HCDR1, HCDR2 and HCDR3), and light chain complementarity determining regions (LCDR1, LCDR2 and LCDR3) of the exemplary anti-EGFRvIII antibodies. Table 2 sets forth the nucleic acid sequence identifiers of the HCVRs, LCVRs, HCDR1, HCDR2 HCDR3, LCDR1, LCDR2 and LCDR3 of the exemplary anti-EGFRvIII antibodies.

The present invention provides antibodies or antigen-binding fragments thereof that specifically bind EGFRvIII, comprising an HCVR comprising an amino acid sequence selected from any of the HCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind EGFRvIII, comprising an LCVR comprising an amino acid sequence selected from any of the LCVR amino acid sequences listed in Table 1, or a substantially similar sequence thereof having at least 90%, at least 95%, at least 98% or at least 99% sequence identity thereto.

The present invention also provides antibodies or antigen-binding fragments thereof that specifically bind EGFRvIII, comprising an HCVR and an LCVR amino acid sequence pair (HCVR/LCVR) comprising any of the HCVR amino acid sequences listed in Table 1 paired with any of the LCVR amino acid sequences listed in Table 1. According to certain embodiments, the present invention provides antibodies, or antigen-binding fragments thereof, comprising an HCVR/LCVR amino acid sequence pair contained within any of the exemplary anti-EGFRvIII antibodies listed in Table 1. In certain embodiments, the HCVR/LCVR amino acid sequence pair is selected from the group consisting of: 2/20, 18/26, 34/42, 50/58, 66/74, 82/90, 98/106, 114/122, and 130/138.

The present invention also provides antibodies or antigen-binding fragments thereof that specifically bind EGFRvIII, comprising a heavy chain CDR1 (HCDR1) comprising an amino acid sequence selected from any of the HCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind EGFRvIII, comprising a heavy chain CDR2 (HCDR2) comprising an amino acid sequence selected from any of the HCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind EGFRvIII, comprising a heavy chain CDR3 (HCDR3) comprising an amino acid sequence selected from any of the HCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind EGFRvIII, comprising a light chain CDR1 (LCDR1) comprising an amino acid sequence selected from any of the LCDR1 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind EGFRvIII, comprising a light chain CDR2 (LCDR2) comprising an amino acid sequence selected from any of the LCDR2 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind EGFRvIII, comprising a light chain CDR3 (LCDR3) comprising an amino acid sequence selected from any of the LCDR3 amino acid sequences listed in Table 1 or a substantially similar sequence thereof having at least 90%, at least 95%, at least 98% or at least 99% sequence identity.

The present invention also provides antibodies or antigen-binding fragments thereof that specifically bind EGFRvIII, comprising an HCDR3 and an LCDR3 amino acid sequence pair (HCDR3/LCDR3) comprising any of the HCDR3 amino acid sequences listed in Table 1 paired with any of the LCDR3 amino acid sequences listed in Table 1. According to certain embodiments, the present invention provides antibodies, or antigen-binding fragments thereof, comprising an HCDR3/LCDR3 amino acid sequence pair contained within any of the exemplary anti-EGFRvIII antibodies listed in Table 1.

The present invention also provides antibodies or antigen-binding fragments thereof that specifically bind EGFRvIII, comprising a set of six CDRs (i.e., HCDR1-HCDR2-HCDR3-LCDR1-LCDR2-LCDR3) contained within any of the exemplary anti-EGFRvIII antibodies listed in Table 1. In certain embodiments, the HCDR1-HCDR2-HCDR3-LCDR1-LCDR2-LCDR3 amino acid sequences set is selected from the group consisting of: 4-6-8-12-14-16; 20-22-24-28-30-32; 36-38-40-44-46-48; 52-54-56-60-62-64; 68-70-72-76-78-80; 84-86-88-92-94-96; 100-102-104-108-110-112; 116-118-120-124-126-128; and 132-134-136-140-142-144.

In a related embodiment, the present invention provides antibodies, or antigen-binding fragments thereof that specifically bind EGFRvIII, comprising a set of six CDRs (i.e., HCDR1-HCDR2-HCDR3-LCDR1-LCDR2-LCDR3) contained within an HCVR/LCVR amino acid sequence pair as defined by any of the exemplary anti-EGFRvIII antibodies listed in Table 1. For example, the present invention includes antibodies or antigen-binding fragments thereof that specifically bind EGFRvIII, comprising the HCDR1-HCDR2-HCDR3-LCDR1-LCDR2-LCDR3 amino acid sequences set contained within an HCVR/LCVR amino acid sequence pair selected from the group consisting of: 18/26; 66/74; 274/282; 290/298; and 370/378. Methods and techniques for identifying CDRs within HCVR and LCVR amino acid sequences are well known in the art and can be used to identify CDRs within the specified HCVR and/or LCVR amino acid sequences disclosed herein. Exemplary conventions that can be used to identify the boundaries of CDRs include, e.g., the Kabat definition, the Chothia definition, and the AbM definition. In general terms, the Kabat definition is based on sequence variability, the Chothia definition is based on the location of the structural loop regions, and the AbM definition is a compromise between the Kabat and Chothia approaches. See, e.g., Kabat, "Sequences of Proteins of Immunological Interest," National Institutes of Health, Bethesda, Md. (1991); Al-Lazikani et al., *J. Mol. Biol.* 273:927-948 (1997); and Martin et al., *Proc. Natl. Acad. Sci. USA* 86:9268-9272 (1989). Public databases are also available for identifying CDR sequences within an antibody.

The present invention also provides nucleic acid molecules encoding anti-EGFRvIII antibodies or portions thereof. For example, the present invention provides nucleic acid molecules encoding any of the HCVR amino acid sequences listed in Table 1; in certain embodiments the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto.

The present invention also provides nucleic acid molecules encoding any of the LCVR amino acid sequences listed in Table 1; in certain embodiments the nucleic acid molecule comprises a polynucleotide sequence selected from any of the LCVR nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR1 amino acid sequences listed in Table 1; in certain embodiments the nucleic acid molecule comprises a polynucleotide sequence selected from any of the HCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR2 amino acid sequences listed in Table 1; in certain embodiments the nucleic acid molecule comprises a polynucleotide sequence selected from any of the HCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the HCDR3 amino acid sequences listed in Table 1; in certain embodiments the nucleic acid molecule comprises a polynucleotide sequence selected from any of the HCDR3 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR1 amino acid sequences listed in Table 1; in certain embodiments the nucleic acid molecule comprises a polynucleotide sequence selected from any of the LCDR1 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR2 amino acid sequences listed in Table 1; in certain embodiments the nucleic acid molecule comprises a polynucleotide sequence selected from any of the LCDR2 nucleic acid sequences listed in Table 2, or a substantially similar sequence thereof having at least 90%, at least 95%, at least 98% or at least 99% sequence identity thereto.

The present invention also provides nucleic acid molecules encoding any of the LCDR3 amino acid sequences listed in Table 1; in certain embodiments the nucleic acid molecule comprises a polynucleotide sequence selected from any of the LCDR3 nucleic acid sequences listed in Table 2, or a substantially similar sequence thereof having at least 90%, at least 95%, at least 98% or at least 99% sequence identity thereto.

The present invention also provides nucleic acid molecules encoding an HCVR, wherein the HCVR comprises a set of three CDRs (i.e., HCDR1-HCDR2-HCDR3), wherein the HCDR1-HCDR2-HCDR3 amino acid sequence set is as defined by any of the exemplary anti-EGFRvIII antibodies listed in Table 1.

The present invention also provides nucleic acid molecules encoding an LCVR, wherein the LCVR comprises a set of three CDRs (i.e., LCDR1-LCDR2-LCDR3), wherein the LCDR1-LCDR2-LCDR3 amino acid sequence set is as defined by any of the exemplary anti-EGFRvIII antibodies listed in Table 1.

The present invention also provides nucleic acid molecules encoding both an HCVR and an LCVR, wherein the HCVR comprises an amino acid sequence of any of the HCVR amino acid sequences listed in Table 1, and wherein the LCVR comprises an amino acid sequence of any of the LCVR amino acid sequences listed in Table 1. In certain embodiments, the nucleic acid molecule comprises a polynucleotide sequence selected from any of the HCVR nucleic acid sequences listed in Table 2, or a substantially similar sequence thereof having at least 90%, at least 95%, at least 98% or at least 99% sequence identity thereto, and a polynucleotide sequence selected from any of the LCVR nucleic acid sequences listed in Table 2, or a substantially similar sequence thereof having at least 90%, at least 95%, at least 98% or at least 99% sequence identity thereto. In certain embodiments according to this aspect of the invention, the nucleic acid molecule encodes an HCVR and LCVR, wherein the HCVR and LCVR are both derived from the same anti-EGFRvIII antibody listed in Table 1.

The present invention also provides recombinant expression vectors capable of expressing a polypeptide comprising a heavy or light chain variable region of an anti-EGFRvIII antibody. For example, the present invention includes recombinant expression vectors comprising any of the nucleic acid molecules mentioned above, i.e., nucleic acid molecules encoding any of the HCVR, LCVR, and/or CDR sequences as set forth in Table 1. Also included within the scope of the present invention are host cells into which such vectors have been introduced, as well as methods of producing the antibodies or portions thereof by culturing the host cells under conditions permitting production of the antibodies or antibody fragments, and recovering the antibodies and antibody fragments so produced.

The present invention includes anti-EGFRvIII antibodies having a modified glycosylation pattern. In some embodiments, modification to remove undesirable glycosylation sites may be useful, or an antibody lacking a fucose moiety present on the oligosaccharide chain, for example, to increase antibody dependent cellular cytotoxicity (ADCC) function (see Shield et al. (2002) JBC 277:26733). In other applications, modification of galactosylation can be made in order to modify complement dependent cytotoxicity (CDC).

In another aspect, the invention provides a pharmaceutical composition comprising a recombinant human antibody or fragment thereof which specifically binds EGFRvIII and a pharmaceutically acceptable carrier. In a related aspect, the invention features a composition which is a combination of an anti-EGFRvIII antibody and a second therapeutic agent. In one embodiment, the second therapeutic agent is any agent that is advantageously combined with an anti-EGFRvIII antibody. The present invention also provides antibody-drug conjugates (ADCs) comprising an anti-EGFRvIII antibody conjugated to a cytotoxic agent. Exemplary combination therapies, co-formulations, and ADCs involving the anti-EGFRvIII antibodies of the present invention are disclosed elsewhere herein.

In yet another aspect, the invention provides therapeutic methods for killing tumor cells or for inhibiting or attenuating tumor cell growth using an anti-EGFRvIII antibody or antigen-binding portion of an antibody of the invention. The therapeutic methods according to this aspect of the invention comprise administering a therapeutically effective amount of a pharmaceutical composition comprising an antibody or antigen-binding fragment of an antibody of the invention to a subject in need thereof. The disorder treated is any disease or condition which is improved, ameliorated, inhibited or prevented by targeting EGFRvIII and/or by inhibiting ligand-mediated cell signaling through EGFRvIII.

Other embodiments will become apparent from a review of the ensuing detailed description. Other embodiments will become apparent from a review of the ensuing detailed description.

BRIEF DESCRIPTION OF THE FIGURES

FIG. 5(a-d) shows the results of pharmacokinetics analysis for anti-EGFRvIII antibody H1H863N2(Fuc+) (FIG. 5d) and control antibodies (as described above), i.e., Control I (FIG. 5b), Control III (FIG. 5c), and Control IV (FIG. 5a), in wild-type mice (●) or mice expressing human EGFR (■).

DETAILED DESCRIPTION

Figure 1A:
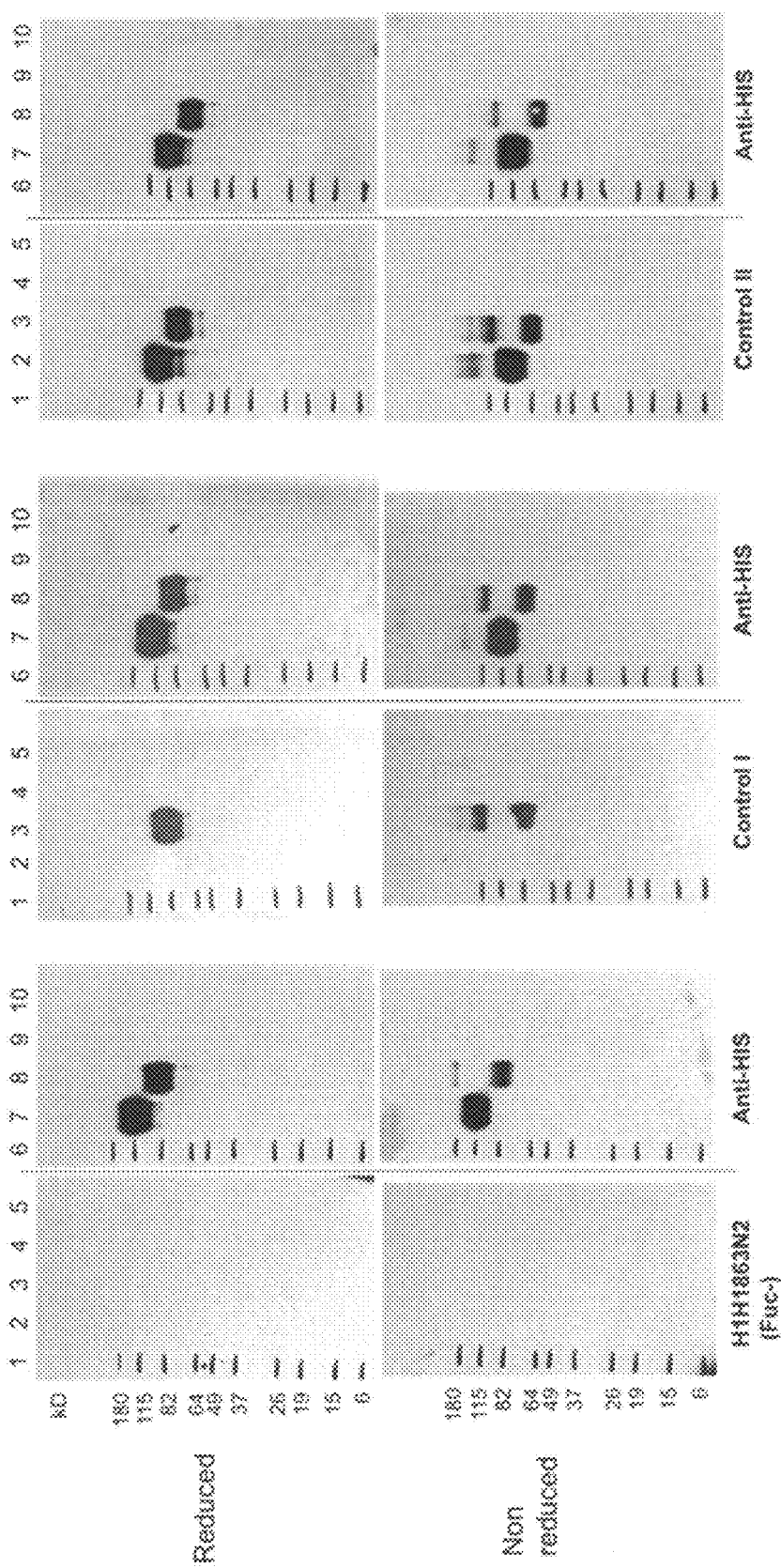
FIG. 1(a-b) shows the results of western blot of EGFR and EGFRvIII using anti-EGFRvIII antibodies [i.e., H1H1863N2(Fuc−), and Controls I and II in FIG. 1a; and H1H1911, H1H1912, and H1H1915 in FIG. 1b], or anti-His antibody, under reduced (upper panels) and non-reduced (lower panels) conditions. Lanes 1 and 6: 10 µl of BENCH-MARK™ standard (INVITROGEN™); Lanes 2 and 7: 400 ng of hEGFR-mmh (SEQ ID NO:154); Lane 3 and 8: 400 ng of hEGFRvIII-mmh (SEQ ID NO:152); and Lanes 4, 5, 9 and 10: space. Control I: Human anti-EGFRvIII junctional peptide antibody (IgG1) disclosed in U.S. Pat. No. 7,736,644; and Control II: Chimeric anti-EGFRvIII/EGFR antibody disclosed in U.S. Pat. No. 7,589,180.

Before the present invention is described, it is to be understood that this invention is not limited to particular methods and experimental conditions described, as such methods and conditions may vary. It is also to be understood that the terminology used herein is for the purpose of describing particular embodiments only, and is not intended to be limiting, since the scope of the present invention will be limited only by the appended claims.

Unless defined otherwise, all technical and scientific terms used herein have the same meaning as commonly understood by one of ordinary skill in the art to which this invention belongs. As used herein, the term "about," when used in reference to a particular recited numerical value, means that the value may vary from the recited value by no more than 1%. For example, as used herein, the expression "about 100" includes 99 and 101 and all values in between (e.g., 99.1, 99.2, 99.3, 99.4, etc.).

Although any methods and materials similar or equivalent to those described herein can be used in the practice or testing of the present invention, the preferred methods and materials are now described. All patents, applications and non-patent publications mentioned in this specification are incorporated herein by reference in their entireties.

Definitions

The term "EGFRvIII," as used herein, refers to the human EGFR class III variant having the amino acid sequence shown in SEQ ID NO:147, or a biologically active fragment thereof, which exhibits any characteristics specific for EGFRvIII, as opposed to those in common with normally expressed EGFR, unless specifically indicated otherwise. EGFRvIII lacks amino acid residues 6 through 273 of mature EGFR (i.e., SEQ ID NO:146 without the signal peptide, i.e., residues 1-24) and contains a new glycine residue at position 6 between amino acid residues 5 and 274.

All references to proteins, polypeptides and protein fragments herein are intended to refer to the human version of the respective protein, polypeptide or protein fragment unless explicitly specified as being from a non-human species. Thus, the expression "EGFRvIII" means human EGFRvIII unless specified as being from a non-human species, e.g., "mouse EGFRvIII," "monkey EGFRvIII," etc.

As used herein, the expression "cell surface-expressed EGFRvIII" means one or more EGFRvIII protein(s), or the extracellular domain thereof, that is/are expressed on the surface of a cell in vitro or in vivo, such that at least a portion of a EGFRvIII protein is exposed to the extracellular side of the cell membrane and is accessible to an antigen-binding portion of an antibody. A "cell surface-expressed EGFRvIII" can comprise or consist of an EGFRvIII protein expressed on the surface of a cell which normally expresses EGFRvIII protein. Alternatively, "cell surface-expressed EGFRvIII" can comprise or consist of EGFRvIII protein expressed on the surface of a cell that normally does not express human EGFRvIII on its surface but has been artificially engineered to express EGFRvIII on its surface.

As used herein, the expression "anti-EGFRvIII antibody" includes both monovalent antibodies with a single specificity, as well as bispecific antibodies comprising a first arm that binds EGFRvIII and a second arm that binds a second (target) antigen, wherein the anti-EGFRvIII arm comprises any of the HCVR/LCVR or CDR sequences as set forth in Table 1 herein. The expression "anti-EGFRvIII antibody" also includes antibody-drug conjugates (ADCs) comprising an anti-EGFRvIII antibody or antigen-binding portion thereof conjugated to a drug or toxin (i.e., cytotoxic agent). The expression "anti-EGFRvIII antibody" also includes antibody-radionuclide conjugates (ARCs) comprising an anti-EGFRvIII antibody or antigen-binding portion thereof conjugated to a radionuclide.

The term "antibody", as used herein, means any antigen-binding molecule or molecular complex comprising at least one complementarity determining region (CDR) that specifically binds to or interacts with a particular antigen (e.g., EGFRvIII). The term "antibody" includes immunoglobulin molecules comprising four polypeptide chains, two heavy (H) chains and two light (L) chains inter-connected by disulfide bonds, as well as multimers thereof (e.g., IgM). Each heavy chain comprises a heavy chain variable region (abbreviated herein as HCVR or $V_H$) and a heavy chain constant region. The heavy chain constant region comprises three domains, $C_H1$, $C_H2$ and $C_H3$. Each light chain comprises a light chain variable region (abbreviated herein as LCVR or $V_L$) and a light chain constant region. The light chain constant region comprises one domain ($C_L1$). The $V_H$ and $V_L$ regions can be further subdivided into regions of hypervariability, termed complementarity determining regions (CDRs), interspersed with regions that are more conserved, termed framework regions (FR). Each $V_H$ and $V_L$ is composed of three CDRs and four FRs, arranged from amino-terminus to carboxy-terminus in the following order: FR1, CDR1, FR2, CDR2, FR3, CDR3, FR4. In different embodiments of the invention, the FRs of the anti-EGFRvIII antibody (or antigen-binding portion thereof) may be identical to the human germline sequences, or may be naturally or artificially modified. An amino acid consensus sequence may be defined based on a side-by-side analysis of two or more CDRs.

The term "antibody", as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g. monovalent nanobodies, bivalent nanobodies, etc.), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a $V_H$ domain associated with a $V_L$ domain, the $V_H$ and $V_L$ domains may be situated relative to one another in any suitable arrangement. For example, the variable region may be dimeric and contain $V_H$-$V_H$, $V_H$-$V_L$ or $V_L$-$V_L$ dimers. Alternatively, the antigen-binding fragment of an antibody may contain a monomeric $V_H$ or $V_L$ domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody of the present invention include: (i) $V_H$-$C_H1$; (ii) $V_H$-$C_H2$; (iii) $V_H$-$C_H3$; (iv) $V_H$-$C_H1$-$C_H2$; (V) $V_H$-$C_H1$-$C_H2$-$C_H3$; (VI) $V_H$-$C_H2$-$C_H3$; MD $V_H$-$C_L$; (Viii) $V_L$-$C_H1$; (ix) $V_L$-$C_H2$; (x) $V_L$-$C_H3$; (Xi) $V_L$-$C_H1$-$C_H2$; (XII) $V_L$-$C_H1$-$C_H2$-$C_H3$; (Xiii) $V_L$-$C_H2$-$C_H3$; and (xiv) $V_L$-$C_L$. In any configuration of variable and constant domains, including any of the exemplary configurations listed above, the variable and constant domains may be either directly linked to one another or may be linked by a full or partial hinge or linker region. A hinge region may consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody of the present invention may comprise a homo-dimer or hetero-dimer (or other multimer) of any of the variable and constant domain configurations listed above in non-covalent association with one another and/or with one or more monomeric $V_H$ or $V_L$ domain (e.g., by disulfide bond(s)).

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may be adapted for use in the context of an antigen-binding fragment of an antibody of the present invention using routine techniques available in the art.

The antibodies of the present invention may function through complement-dependent cytotoxicity (CDC) or antibody-dependent cell-mediated cytotoxicity (ADCC). "Complement-dependent cytotoxicity" (CDC) refers to lysis of antigen-expressing cells by an antibody of the invention in the presence of complement. "Antibody-dependent cell-mediated cytotoxicity" (ADCC) refers to a cell-mediated reaction in which nonspecific cytotoxic cells that express Fc receptors (FcRs) (e.g., Natural Killer (NK) cells, neutrophils, and macrophages) recognize bound antibody on a target cell and thereby lead to lysis of the target cell. CDC and ADCC can be measured using assays that are well known and available in the art. (See, e.g., U.S. Pat. Nos. 5,500,362 and 5,821,337, and Clynes et al. (1998) Proc. Natl. Acad. Sci. (USA) 95:652-656). The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

In certain embodiments of the invention, the anti-EGFRvIII antibodies of the invention are human antibodies. The term "human antibody", as used herein, is intended to include antibodies having variable and constant regions derived from human germline immunoglobulin sequences. The human antibodies of the invention may include amino acid residues not encoded by human germline immunoglobulin sequences (e.g., mutations introduced by random or site-specific mutagenesis in vitro or by somatic mutation in vivo), for example in the CDRs and in particular CDR3. However, the term "human antibody", as used herein, is not intended to include antibodies in which CDR sequences derived from the germline of another mammalian species, such as a mouse, have been grafted onto human framework sequences.

The antibodies of the invention may, in some embodiments, be recombinant human antibodies. The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res. 20:6287-6295) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the $V_H$ and $V_L$ regions of the recombinant antibodies are sequences that, while derived from and related to human germline $V_H$ and $V_L$ sequences, may not naturally exist within the human antibody germline repertoire in vivo.

Human antibodies can exist in two forms that are associated with hinge heterogeneity. In one form, an immunoglobulin molecule comprises a stable four chain construct of approximately 150-160 kDa in which the dimers are held together by an interchain heavy chain disulfide bond. In a second form, the dimers are not linked via interchain disulfide bonds and a molecule of about 75-80 kDa is formed composed of a covalently coupled light and heavy chain (half-antibody). These forms have been extremely difficult to separate, even after affinity purification.

The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses antibodies having one or more mutations in the hinge, $C_H2$ or $C_H3$ region which may be desirable, for example, in production, to improve the yield of the desired antibody form.

The antibodies of the invention may be isolated antibodies. An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody" for purposes of the present invention. An isolated antibody also includes an antibody in situ within a recombinant cell. Isolated antibodies are antibodies that have been subjected to at least one purification or isolation step. According to certain embodiments, an isolated antibody may be substantially free of other cellular material and/or chemicals.

The anti-EGFRvIII antibodies disclosed herein may comprise one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). A person of ordinary skill in the art, starting with the heavy and light chain variable region sequences disclosed herein, can easily produce numerous antibodies and antigen-binding fragments which comprise one or more individual germline mutations or combinations thereof. In certain embodiments, all of the framework and/or CDR residues within the $V_H$ and/or $V_L$ domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies of the present invention may contain any combination of two or more germline mutations within the framework and/or CDR regions, e.g., wherein certain individual residues are mutated to the corresponding residue of a particular germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. Antibodies and antigen-binding fragments obtained in this general manner are encompassed within the present invention.

The present invention also includes anti-EGFRvIII antibodies comprising variants of any of the HCVR, LCVR, and/or CDR amino acid sequences disclosed herein having one or more conservative substitutions. For example, the present invention includes anti-EGFRvIII antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences set forth in Table 1 herein.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The term "substantial identity" or "substantially identical," when referring to a nucleic acid or fragment thereof, indicates that, when optimally aligned with appropriate nucleotide insertions or deletions with another nucleic acid (or its complementary strand), there is nucleotide sequence identity in at least about 95%, and more preferably at least about 96%, 97%, 98% or 99% of the nucleotide bases, as measured by any well-known algorithm of sequence identity, such as FASTA, BLAST or Gap, as discussed below. A nucleic acid molecule having substantial identity to a reference nucleic acid molecule may, in certain instances, encode a polypeptide having the same or substantially similar amino acid sequence as the polypeptide encoded by the reference nucleic acid molecule.

As applied to polypeptides, the term "substantial similarity" or "substantially similar" means that two peptide sequences, when optimally aligned, such as by the programs GAP or BESTFIT using default gap weights, share at least 95% sequence identity, even more preferably at least 98% or 99% sequence identity. Preferably, residue positions which are not identical differ by conservative amino acid substitutions. A "conservative amino acid substitution" is one in which an amino acid residue is substituted by another amino acid residue having a side chain (R group) with similar chemical properties (e.g., charge or hydrophobicity). In general, a conservative amino acid substitution will not substantially change the functional properties of a protein. In cases where two or more amino acid sequences differ from each other by conservative substitutions, the percent sequence identity or degree of similarity may be adjusted upwards to correct for the conservative nature of the substitution. Means for making this adjustment are well-known to those of skill in the art. See, e.g., Pearson (1994) Methods Mol. Biol. 24: 307-331, herein incorporated by reference. Examples of groups of amino acids that have side chains with similar chemical properties include (1) aliphatic side chains: glycine, alanine, valine, leucine and isoleucine; (2) aliphatic-hydroxyl side chains: serine and threonine; (3) amide-containing side chains: asparagine and glutamine; (4) aromatic side chains: phenylalanine, tyrosine, and tryptophan; (5) basic side chains: lysine, arginine, and histidine; (6) acidic side chains: aspartate and glutamate, and (7) sulfur-containing side chains are cysteine and methionine. Preferred conservative amino acids substitution groups are: valine-leucine-isoleucine, phenylalanine-tyrosine, lysine-arginine, alanine-valine, glutamate-aspartate, and asparagine-glutamine. Alternatively, a conservative replacement is any change having a positive value in the PAM250 log-likelihood matrix disclosed in Gonnet et al. (1992) Science 256: 1443-1445, herein incorporated by reference. A "moderately conservative" replacement is any change having a nonnegative value in the PAM250 log-likelihood matrix.

Sequence similarity for polypeptides, which is also referred to as sequence identity, is typically measured using sequence analysis software. Protein analysis software matches similar sequences using measures of similarity assigned to various substitutions, deletions and other modifications, including conservative amino acid substitutions. For instance, GCG software contains programs such as Gap and Bestfit which can be used with default parameters to determine sequence homology or sequence identity between closely related polypeptides, such as homologous polypeptides from different species of organisms or between a wild type protein and a mutein thereof. See, e.g., GCG Version 6.1. Polypeptide sequences also can be compared using FASTA using default or recommended parameters, a program in GCG Version 6.1. FASTA (e.g., FASTA2 and FASTA3) provides alignments and percent sequence identity of the regions of the best overlap between the query and search sequences (Pearson (2000) supra). Another preferred algorithm when comparing a sequence of the invention to a database containing a large number of sequences from different organisms is the computer program BLAST, especially BLASTP or TBLASTN, using default parameters. See, e.g., Altschul et al. (1990) J. Mol. Biol. 215:403-410 and Altschul et al. (1997) Nucleic Acids Res. 25:3389-402, each herein incorporated by reference.

pH-Dependent Binding

The present invention includes anti-EGFRvIII antibodies with pH-dependent binding characteristics. For example, an anti-EGFRvIII antibody of the present invention may exhibit reduced binding to EGFRvIII at acidic pH as compared to neutral pH. Alternatively, anti-EGFRvIII antibodies of the invention may exhibit enhanced binding to EGFRvIII at acidic pH as compared to neutral pH. The expression "acidic pH" includes pH values less than about 6.2, e.g., about 6.0, 5.95, 5, 9, 5.85, 5.8, 5.75, 5.7, 5.65, 5.6, 5.55, 5.5, 5.45, 5.4, 5.35, 5.3, 5.25, 5.2, 5.15, 5.1, 5.05, 5.0, or less. As used herein, the expression "neutral pH" means a pH of about 7.0 to about 7.4. The expression "neutral pH" includes pH values of about 7.0, 7.05, 7.1, 7.15, 7.2, 7.25, 7.3, 7.35, and 7.4.

In certain instances, "reduced binding to EGFRvIII at acidic pH as compared to neutral pH" is expressed in terms of a ratio of the $K_D$ value of the antibody binding to EGFRvIII at acidic pH to the $K_D$ value of the antibody binding to EGFRvIII at neutral pH (or vice versa). For example, an antibody or antigen-binding fragment thereof may be regarded as exhibiting "reduced binding to EGFRvIII at acidic pH as compared to neutral pH" for purposes of the present invention if the antibody or antigen-binding fragment thereof exhibits an acidic/neutral $K_D$ ratio of about 3.0 or greater. In certain exemplary embodiments, the acidic/neutral $K_D$ ratio for an antibody or antigen-binding fragment of the present invention can be about 3.0, 3.5, 4.0, 4.5, 5.0, 5.5, 6.0, 6.5, 7.0, 7.5, 8.0, 8.5, 9.0, 9.5, 10.0, 10.5, 11.0, 11.5, 12.0, 12.5, 13.0, 13.5, 14.0, 14.5, 15.0, 20.0. 25.0, 30.0, 40.0, 50.0, 60.0, 70.0, 100.0 or greater.

Antibodies with pH-dependent binding characteristics may be obtained, e.g., by screening a population of antibodies for reduced (or enhanced) binding to a particular antigen at acidic pH as compared to neutral pH. Additionally, modifications of the antigen-binding domain at the amino acid level may yield antibodies with pH-dependent characteristics. For example, by substituting one or more amino acids of an antigen-binding domain (e.g., within a CDR) with a histidine residue, an antibody with reduced antigen-binding at acidic pH relative to neutral pH may be obtained.

Anti-EGFRvIII Antibodies Comprising Fc Variants

According to certain embodiments of the present invention, anti-EGFRvIII antibodies are provided comprising an Fc domain comprising one or more mutations which enhance or diminish antibody binding to the FcRn receptor, e.g., at acidic pH as compared to neutral pH. For example, the present invention includes anti-EGFRvIII antibodies comprising a mutation in the $C_H2$ or a $C_H3$ region of the Fc domain, wherein the mutation(s) increases the affinity of the Fc domain to FcRn in an acidic environment (e.g., in an endosome where pH ranges from about 5.5 to about 6.0). Such mutations may result in an increase in serum half-life of the antibody when administered to an animal. Non-limiting examples of such Fc modifications include, e.g., a modification at position 250 (e.g., E or Q); 250 and 428 (e.g., L or F); 252 (e.g., L/Y/F/W or T), 254 (e.g., S or T), and 256 (e.g., S/R/Q/E/D or T); or a modification at position 428 and/or 433 (e.g., H/L/R/S/P/Q or K) and/or 434 (e.g., A, W, H, F or Y [N434A, N434W, N434H, N434F or N434Y]); or a modification at position 250 and/or 428; or a modification at position 307 or 308 (e.g., 308F, V308F), and 434. In one embodiment, the modification comprises a 428L (e.g., M428L) and 434S (e.g., N434S) modification; a 428L, 259I (e.g., V259I), and 308F (e.g., V308F) modification; a 433K (e.g., H433K) and a 434 (e.g., 434Y) modification; a 252, 254, and 256 (e.g., 252Y, 254T, and 256E) modification; a 250Q and 428L modification (e.g., T250Q and M428L); and a 307 and/or 308 modification (e.g., 308F or 308P). In yet another embodiment, the modification comprises a 265A (e.g., D265A) and/or a 297A (e.g., N297A) modification.

For example, the present invention includes anti-EGFRvIII antibodies comprising an Fc domain comprising one or more pairs or groups of mutations selected from the group consisting of: 250Q and 248L (e.g., T250Q and M248L); 252Y, 254T and 256E (e.g., M252Y, S254T and T256E); 428L and 434S (e.g., M428L and N434S); 257I and 311I (e.g., P257I and Q311I); 257I and 434H (e.g., P257I and N434H); 376V and 434H (e.g., D376V and N434H); 307A, 380A and 434A (e.g., T307A, E380A and N434A); and 433K and 434F (e.g., H433K and N434F). All possible combinations of the foregoing Fc domain mutations, and other mutations within the antibody variable domains disclosed herein, are contemplated within the scope of the present invention.

The present invention also includes anti-EGFRvIII antibodies comprising a chimeric heavy chain constant ($C_H$) region, wherein the chimeric $C_H$ region comprises segments derived from the $C_H$ regions of more than one immunoglobulin isotype. For example, the antibodies of the invention may comprise a chimeric $C_H$ region comprising part or all of a $C_H2$ domain derived from a human IgG1, human IgG2 or human IgG4 molecule, combined with part or all of a $C_H3$ domain derived from a human IgG1, human IgG2 or human IgG4 molecule. According to certain embodiments, the antibodies of the invention comprise a chimeric $C_H$ region having a chimeric hinge region. For example, a chimeric hinge may comprise an "upper hinge" amino acid sequence (amino acid residues from positions 216 to 227 according to EU numbering) derived from a human IgG1, a human IgG2 or a human IgG4 hinge region, combined with a "lower hinge" sequence (amino acid residues from positions 228 to 236 according to EU numbering) derived from a human IgG1, a human IgG2 or a human IgG4 hinge region. According to certain embodiments, the chimeric hinge region comprises amino acid residues derived from a human IgG1 or a human IgG4 upper hinge and amino acid residues derived from a human IgG2 lower hinge. An antibody comprising a chimeric $C_H$ region as described herein may, in certain embodiments, exhibit modified Fc effector functions without adversely affecting the therapeutic or pharmacokinetic properties of the antibody. (See, e.g., U.S. Provisional Appl. No. 61/759,578, filed Feb. 1, 2013, the disclosure of which is hereby incorporated by reference in its entirety).

Antibody-Drug Conjugates (ADCs)

The present invention provides antibody-drug conjugates (ADCs) comprising an anti-EGFRvIII antibody or antigen-binding fragment thereof conjugated to a therapeutic moiety such as a cytotoxic agent, a chemotherapeutic drug, or a radioisotope.

Cytotoxic agents include any agent that is detrimental to the growth, viability or propagation of cells. Examples of suitable cytotoxic agents and chemotherapeutic agents that can be conjugated to anti-EGFRvIII antibodies in accordance with this aspect of the invention include, e.g., 1-(2chloroethyl)-1,2-dimethanesulfonyl hydrazide, 1,8-dihydroxy-bicyclo[7.3.1]trideca-4,9-diene-2,6-diyne-13-one, 1-dehydrotestosterone, 5-fluorouracil, 6-mercaptopurine, 6-thioguanine, 9-amino camptothecin, actinomycin D, amanitins, aminopterin, anguidine, anthracycline, anthramycin (AMC), auristatins, bleomycin, busulfan, butyric acid, calicheamicins, camptothecin, carminomycins, carmustine, cemadotins, cisplatin, colchicin, combretastatins, cyclophosphamide, cytarabine, cytochalasin B, dactinomycin, daunorubicin, decarbazine, diacetoxypentyldoxorubicin, dibromomannitol, dihydroxy anthracin dione, disorazoles, dolastatin, doxorubicin, duocarmycins, echinomycins, eleutherobins, emetine, epothilones, esperamicin, estramustines, ethidium bromide, etoposide, fluorouracils, geldanamycins, gramicidin D, glucocorticoids, irinotecans, leptomycins, leurosines, lidocaine, lomustine (CCNU), maytansinoids, mechlorethamine, melphalan, mercatopurines, methopterins, methotrexate, mithramycin, mitomycin, mitoxantrone, N8-acetyl spermidine, podophyllotoxins, procaine, propranolol, pteridines, puromycin, pyrrolobenzodiazepines (PDBs), rhizoxins, streptozotocin, tallysomycins, taxol, tenoposide, tetracaine, thioepa chlorambucil, tomaymycins, topotecans, tubulysin, vinblastine, vincristine, vindesine, vinorelbines, and derivatives of any of the foregoing. According to certain embodiments, the cytotoxic agent that is conjugated to an anti-EGFRvIII antibody is a maytansinoid such as DM1 or DM4, a tomaymycin derivative, or a dolastatin derivative. Other cytotoxic agents known in the art are contemplated within the scope of the present invention, including, e.g., protein toxins such ricin, *C. difficile* toxin, *pseudomonas* exotoxin, ricin, diphtheria toxin, botulinum toxin, bryodin, saporin, pokeweed toxins (i.e., phytolaccatoxin and phytolaccigenin), and others such as those set forth in Sapra et al., *Pharmacol. & Therapeutics,* 2013, 138:452-469.

The present invention also includes antibody-radionuclide conjugates (ARCs) comprising anti-EGFRvIII antibodies conjugated to one or more radionuclides. Exemplary radionuclides that can be used in the context of this aspect of the invention include, but are not limited to, e.g., $^{225}$Ac, $^{212}$Bi, $^{213}$Bi, $^{131}$I, $^{186}$Re, $^{227}$Th, $^{222}$Rn, $^{223}$Ra, $^{224}$Ra, and $^{90}$Y.

In certain embodiments of the present invention, ADCs are provided comprising an anti-EGFRvIII antibody conjugated to a cytotoxic agent (e.g., any of the cytotoxic agents disclosed above) via a linker molecule. Any linker molecule or linker technology known in the art can be used to create or construct an ADC of the present invention. In certain embodiments, the linker is a cleavable linker. According to other embodiments, the linker is a non-cleavable linker. Exemplary linkers that can be used in the context of the present invention include, linkers that comprise or consist of e.g., MC (6-maleimidocaproyl), MP (maleimidopropanoyl), val-cit (valine-citrulline), val-ala (valine-alanine), dipeptide site in protease-cleavable linker, ala-phe (alanine-phenylalanine), dipeptide site in protease-cleavable linker, PAB (p-aminobenzyloxycarbonyl), SPP (N-Succinimidyl 4-(2-pyridylthio) pentanoate), SMCC (N-Succinimidyl 4-(N-maleimidomethyl)cyclohexane-1 carboxylate), STAB (N-Succinimidyl (4-iodo-acetyl)aminobenzoate), and variants and combinations thereof. Additional examples of linkers that can be used in the context of the present invention are disclosed, e.g., in U.S. Pat. No. 7,754,681 and in Ducry, Bioconjugate Chem., 2010, 21:5-13, and the references cited therein, the contents of which are incorporated by reference herein in their entireties.

The present invention comprises ADCs in which a linker connects an anti-EGFRvIII antibody or antigen-binding molecule to a drug or cytotoxin through an attachment at a particular amino acid within the antibody or antigen-binding molecule. Exemplary amino acid attachments that can be used in the context of this aspect of the invention include, e.g., lysine (see, e.g., U.S. Pat. No. 5,208,020; US 2010/0129314; Hollander et al., Bioconjugate Chem., 2008, 19:358-361; WO 2005/089808; U.S. Pat. No. 5,714,586; US 2013/0101546; and US 2012/0585592), cysteine (see, e.g., US 2007/0258987; WO 2013/055993; WO 2013/055990; WO 2013/053873; WO 2013/053872; WO 2011/130598; US 2013/0101546; and U.S. Pat. No. 7,750,116), selenocysteine (see, e.g., WO 2008/122039; and Hofer et al., Proc. Natl. Acad. Sci., USA, 2008, 105:12451-12456), formyl glycine (see, e.g., Carrico et al., Nat. Chem. Biol., 2007, 3:321-322; Agarwal et al., Proc. Natl. Acad. Sci., USA, 2013, 110:46-51, and Rabuka et al., Nat. Protocols, 2012, 10:1052-1067), non-natural amino acids (see, e.g., WO 2013/068874, and WO 2012/166559), and acidic amino acids (see, e.g., WO 2012/05982). Linkers can also be conjugated to an antigen-binding protein via attachment to carbohydrates (see, e.g., US 2008/0305497, and Ryan et al., Food & Agriculture Immunol., 2001, 13:127-130) and disulfide linkers (see, e.g., WO 2013/085925, WO 2010/010324, WO 2011/018611, and Shaunak et al., Nat. Chem. Biol., 2006, 2:312-313).

Any method known in the art for conjugating a chemical moiety to a peptide, polypeptide or other macromolecule can be used in the context of the present invention to make an anti-EGFRvIII ADC as described herein. An exemplary method for antibody-drug conjugation via a linker is set forth in Example 12 herein. Variations on this exemplary method will be appreciated by persons of ordinary skill in the art and are contemplated within the scope of the present invention.

According to certain embodiments, the present invention provides ADCs, wherein an anti-EGFRvIII antibody as described herein (e.g., the antibody designated H1H1863N2) is conjugated to a linker-drug composition as set forth in WO2014/145090 (e.g., compound "7," also referred to herein as "M0026"), the disclosure of which is hereby incorporated by reference herein in its entirety (see also Example 12, herein).

Epitope Mapping and Related Technologies

The epitope to which the antibodies of the present invention bind may consist of a single contiguous sequence of 3 or more (e.g., 3, 4, 5, 6, 7, 8, 9, 10, 11, 12, 13, 14, 15, 16, 17, 18, 19, 20 or more) amino acids of an EGFRvIII protein. Alternatively, the epitope may consist of a plurality of non-contiguous amino acids (or amino acid sequences) of EGFRvIII. In some embodiments, the epitope is located on or near the ligand-binding domain of EGFRvIII. In other embodiments, the epitope is located outside of the ligand-binding domain of EGFRvIII, e.g., at a location on the surface of EGFRvIII at which an antibody, when bound to such an epitope, does not interfere with ligand binding to EGFRvIII.

The present invention, according to certain embodiments, includes anti-EGFRvIII antibodies that specifically bind EGFRvIII (and do not bind EGFR), wherein the antibodies recognize the EGFRvIII junctional peptide (e.g., SEQ ID NO:148). Such antibodies may be referred to herein as "junctional peptide binders," "EGFRvIII peptide-binding antibodies," and the like. The present invention, according to other embodiments, includes anti-EGFRvIII antibodies that specifically bind EGFRvIII (and do not bind EGFR), wherein the antibodies do not recognize the EGFRvIII junctional peptide (e.g. do not recognize the junctional peptide of SEQ ID NO:148, and/or do not recognize the peptide of SEQ ID NO:165). Such antibodies may be referred to herein as "conformational binders," "EGFRvIII conformational epitope binders," and the like.

Various techniques known to persons of ordinary skill in the art can be used to determine whether an antibody "interacts with one or more amino acids" within a polypeptide or protein. Exemplary techniques include, e.g., routine cross-blocking assay such as that described Antibodies, Harlow and Lane (Cold Spring Harbor Press, Cold Spring Harb., N.Y.), alanine scanning mutational analysis, peptide blots analysis (Reineke, 2004, Methods Mol Biol 248:443-463), and peptide cleavage analysis. In addition, methods such as epitope excision, epitope extraction and chemical modification of antigens can be employed (Tomer, 2000, Protein Science 9:487-496). Another method that can be used to identify the amino acids within a polypeptide with which an antibody interacts is hydrogen/deuterium exchange detected by mass spectrometry. In general terms, the hydrogen/deuterium exchange method involves deuterium-labeling the protein of interest, followed by binding the antibody to the deuterium-labeled protein. Next, the protein/antibody complex is transferred to water to allow hydrogen-deuterium exchange to occur at all residues except for the residues protected by the antibody (which remain deuterium-labeled). After dissociation of the antibody, the target protein is subjected to protease cleavage and mass spectrometry analysis, thereby revealing the deuterium-labeled residues which correspond to the specific amino acids with which the antibody interacts. See, e.g., Ehring (1999) Analytical Biochemistry 267(2):252-259; Engen and Smith (2001) Anal. Chem. 73:256A-265A.

The present invention further includes anti-EGFRvIII antibodies that bind to the same epitope as any of the specific exemplary antibodies described herein (e.g. antibodies comprising any of the amino acid sequences as set forth in Table 1 herein). Likewise, the present invention also includes anti-EGFRvIII antibodies that compete for binding to EGFRvIII with any of the specific exemplary antibodies described herein (e.g. antibodies comprising any of the amino acid sequences as set forth in Table 1 herein).

One can easily determine whether an antibody binds to the same epitope as, or competes for binding with, a reference anti-EGFRvIII antibody by using routine methods known in the art and exemplified herein. For example, to determine if a test antibody binds to the same epitope as a reference anti-EGFRvIII antibody of the invention, the reference antibody is allowed to bind to a EGFRvIII protein. Next, the ability of a test antibody to bind to the EGFRvIII molecule is assessed. If the test antibody is able to bind to EGFRvIII following saturation binding with the reference anti-EGFRvIII antibody, it can be concluded that the test antibody binds to a different epitope than the reference anti-EGFRvIII antibody. On the other hand, if the test antibody is not able to bind to the EGFRvIII molecule following saturation binding with the reference anti-EGFRvIII antibody, then the test antibody may bind to the same epitope as the epitope bound by the reference anti-EGFRvIII antibody of the invention. Additional routine experimentation (e.g., peptide mutation and binding analyses) can then be carried out to confirm whether the observed lack of binding of the test antibody is in fact due to binding to the same epitope as the reference antibody or if steric blocking (or another phenomenon) is responsible for the lack of observed binding. Experiments of this sort can be performed using ELISA, RIA, Biacore, flow cytometry or any other quantitative or qualitative antibody-binding assay available in the art. In accordance with certain embodiments of the present invention, two antibodies bind to the same (or overlapping) epitope if, e.g., a 1-, 5-, 10-, 20- or 100-fold excess of one antibody inhibits binding of the other by at least 50% but preferably 75%, 90% or even 99% as measured in a competitive binding assay (see, e.g., Junghans et al., Cancer Res. 1990:50:1495-1502). Alternatively, two antibodies are deemed to bind to the same epitope if essentially all amino acid mutations in the antigen that reduce or eliminate binding of one antibody reduce or eliminate binding of the other. Two antibodies are deemed to have "overlapping epitopes" if only a subset of the amino acid mutations that reduce or eliminate binding of one antibody reduce or eliminate binding of the other.

To determine if an antibody competes for binding (or cross-competes for binding) with a reference anti-EGFRvIII antibody, the above-described binding methodology is performed in two orientations: In a first orientation, the reference antibody is allowed to bind to an EGFRvIII protein under saturating conditions followed by assessment of binding of the test antibody to the EGFRvIII molecule. In a second orientation, the test antibody is allowed to bind to an EGFRvIII molecule under saturating conditions followed by assessment of binding of the reference antibody to the EGFRvIII molecule. If, in both orientations, only the first (saturating) antibody is capable of binding to the EGFRvIII molecule, then it is concluded that the test antibody and the reference antibody compete for binding to EGFRvIII. As will be appreciated by a person of ordinary skill in the art, an antibody that competes for binding with a reference antibody may not necessarily bind to the same epitope as the reference antibody, but may sterically block binding of the reference antibody by binding an overlapping or adjacent epitope.

Preparation of Human Antibodies

The anti-EGFRvIII antibodies of the present invention can be fully human antibodies. Methods for generating monoclonal antibodies, including fully human monoclonal antibodies are known in the art. Any such known methods can be used in the context of the present invention to make human antibodies that specifically bind to human EGFRvIII.

Using VELOCIMMUNE™ technology, for example, or any other similar known method for generating fully human monoclonal antibodies, high affinity chimeric antibodies to EGFRvIII are initially isolated having a human variable region and a mouse constant region. As in the experimental section below, the antibodies are characterized and selected for desirable characteristics, including affinity, ligand blocking activity, selectivity, epitope, etc. If necessary, mouse constant regions are replaced with a desired human constant region, for example wild-type or modified IgG1 or IgG4, to generate a fully human anti-EGFRvIII antibody. While the constant region selected may vary according to specific use, high affinity antigen-binding and target specificity characteristics reside in the variable region. In certain instances, fully human anti-EGFRvIII antibodies are isolated directly from antigen-positive B cells.

Bioequivalents

The anti-EGFRvIII antibodies and antibody fragments of the present invention encompass proteins having amino acid sequences that vary from those of the described antibodies but that retain the ability to bind human EGFRvIII. Such variant antibodies and antibody fragments comprise one or more additions, deletions, or substitutions of amino acids when compared to parent sequence, but exhibit biological activity that is essentially equivalent to that of the described antibodies. Likewise, the anti-EGFRvIII antibody-encoding DNA sequences of the present invention encompass sequences that comprise one or more additions, deletions, or substitutions of nucleotides when compared to the disclosed sequence, but that encode an anti-EGFRvIII antibody or antibody fragment that is essentially bioequivalent to an anti-EGFRvIII antibody or antibody fragment of the invention. Examples of such variant amino acid and DNA sequences are discussed above.

Two antigen-binding proteins, or antibodies, are considered bioequivalent if, for example, they are pharmaceutical equivalents or pharmaceutical alternatives whose rate and extent of absorption do not show a significant difference when administered at the same molar dose under similar experimental conditions, either single does or multiple dose. Some antibodies will be considered equivalents or pharmaceutical alternatives if they are equivalent in the extent of their absorption but not in their rate of absorption and yet may be considered bioequivalent because such differences in the rate of absorption are intentional and are reflected in the labeling, are not essential to the attainment of effective body drug concentrations on, e.g., chronic use, and are considered medically insignificant for the particular drug product studied.

In one embodiment, two antigen-binding proteins are bioequivalent if there are no clinically meaningful differences in their safety, purity, and potency.

In one embodiment, two antigen-binding proteins are bioequivalent if a patient can be switched one or more times between the reference product and the biological product without an expected increase in the risk of adverse effects, including a clinically significant change in immunogenicity, or diminished effectiveness, as compared to continued therapy without such switching.

In one embodiment, two antigen-binding proteins are bioequivalent if they both act by a common mechanism or mechanisms of action for the condition or conditions of use, to the extent that such mechanisms are known.

Bioequivalence may be demonstrated by in vivo and in vitro methods. Bioequivalence measures include, e.g., (a) an in vivo test in humans or other mammals, in which the concentration of the antibody or its metabolites is measured in blood, plasma, serum, or other biological fluid as a function of time; (b) an in vitro test that has been correlated with and is reasonably predictive of human in vivo bioavailability data; (c) an in vivo test in humans or other mammals in which the appropriate acute pharmacological effect of the antibody (or its target) is measured as a function of time; and (d) in a well-controlled clinical trial that establishes safety, efficacy, or bioavailability or bioequivalence of an antibody.

Bioequivalent variants of anti-EGFRvIII antibodies of the invention may be constructed by, for example, making various substitutions of residues or sequences or deleting terminal or internal residues or sequences not needed for biological activity. For example, cysteine residues not essential for biological activity can be deleted or replaced with other amino acids to prevent formation of unnecessary or incorrect intramolecular disulfide bridges upon renaturation.

In other contexts, bioequivalent antibodies may include anti-EGFRvIII antibody variants comprising amino acid changes which modify the glycosylation characteristics of the antibodies, e.g., mutations which eliminate or remove glycosylation.

Species Selectivity and Species Cross-Reactivity

The present invention, according to certain embodiments, provides anti-EGFRvIII antibodies that bind to human EGFRvIII but not to EGFRvIII from other species. The present invention also includes anti-EGFRvIII antibodies that bind to human EGFRvIII and to EGFRvIII from one or more non-human species. For example, the anti-EGFRvIII antibodies of the invention may bind to human EGFRvIII and may bind or not bind, as the case may be, to one or more of mouse, rat, guinea pig, hamster, gerbil, pig, cat, dog, rabbit, goat, sheep, cow, horse, camel, cynomologous, marmoset, rhesus or chimpanzee EGFRvIII. According to certain exemplary embodiments of the present invention, anti-EGFRvIII antibodies are provided which specifically bind human EGFRvIII and cynomolgus monkey (e.g., *Macaca fascicularis*) EGFRvIII. Other anti-EGFRvIII antibodies of the invention bind human EGFRvIII but do not bind, or bind only weakly, to cynomolgus monkey EGFRvIII.

Multispecific Antibodies

The antibodies of the present invention may be monospecific or multispecific (e.g., bispecific). Multispecific antibodies may be specific for different epitopes of one target polypeptide or may contain antigen-binding domains specific for more than one target polypeptide. See, e.g., Tutt et al., 1991, J. Immunol. 147:60-69; Kufer et al., 2004, Trends Biotechnol. 22:238-244. The anti-EGFRvIII antibodies of the present invention can be linked to or co-expressed with another functional molecule, e.g., another peptide or protein. For example, an antibody or fragment thereof can be functionally linked (e.g., by chemical coupling, genetic fusion, noncovalent association or otherwise) to one or more other molecular entities, such as another antibody or antibody fragment to produce a bi-specific or a multispecific antibody with a second binding specificity.

The present invention includes bispecific antibodies wherein one arm of an immunoglobulin binds human EGFRvIII, and the other arm of the immunoglobulin is specific for a second antigen. The EGFRvIII-binding arm can comprise any of the HCVR/LCVR or CDR amino acid sequences as set forth in Table 1 herein. In certain embodiments, the EGFRvIII-binding arm binds human EGFRvIII and blocks ligand binding to EGFRvIII. In other embodiments, the EGFRvIII-binding arm binds human EGFRvIII but does not block ligand binding to EGFRvIII.

An exemplary bispecific antibody format that can be used in the context of the present invention involves the use of a first immunoglobulin (Ig) $C_H3$ domain and a second Ig $C_H3$ domain, wherein the first and second Ig $C_H3$ domains differ from one another by at least one amino acid, and wherein at least one amino acid difference reduces binding of the bispecific antibody to Protein A as compared to a bi-specific antibody lacking the amino acid difference. In one embodiment, the first Ig $C_H3$ domain binds Protein A and the second Ig $C_H3$ domain contains a mutation that reduces or abolishes Protein A binding such as an H95R modification (by IMGT exon numbering; H435R by EU numbering). The second $C_H3$ may further comprise a Y96F modification (by IMGT; Y436F by EU). Further modifications that may be found within the second $C_H3$ include: D16E, L18M, N44S, K52N, V57M, and V82I (by IMGT; D356E, L358M, N384S, K392N, V397M, and V422I by EU) in the case of IgG1 antibodies; N44S, K52N, and V82I (IMGT; N384S, K392N, and V422I by EU) in the case of IgG2 antibodies; and Q15R, N44S, K52N, V57M, R69K, E79Q, and V82I (by IMGT; Q355R, N384S, K392N, V397M, R409K, E419Q, and V422I by EU) in the case of IgG4 antibodies. Variations on the bispecific antibody format described above are contemplated within the scope of the present invention.

Other exemplary bispecific formats that can be used in the context of the present invention include, without limitation, e.g., scFv-based or diabody bispecific formats, IgG-scFv fusions, dual variable domain (DVD)-Ig, Quadroma, knobs-into-holes, common light chain (e.g., common light chain with knobs-into-holes, etc.), CrossMab, CrossFab, (SEED) body, leucine zipper, Duobody, IgG1/IgG2, dual acting Fab (DAF)-IgG, and Mabe bispecific formats (see, e.g., Klein et al. 2012, mAbs 4:6, 1-11, and references cited therein, for a review of the foregoing formats). Bispecific antibodies can also be constructed using peptide/nucleic acid conjugation, e.g., wherein unnatural amino acids with orthogonal chemical reactivity are used to generate site-specific antibody-oligonucleotide conjugates which then self-assemble into multimeric complexes with defined composition, valency and geometry. (See, e.g., Kazane et al., *J. Am. Chem. Soc.* [Epub: Dec. 4, 2012]).

Therapeutic Formulation and Administration

The invention provides pharmaceutical compositions comprising the anti-EGFRvIII antibodies or antigen-binding fragments thereof of the present invention. The pharmaceutical compositions of the invention are formulated with suitable carriers, excipients, and other agents that provide improved transfer, delivery, tolerance, and the like. A multitude of appropriate formulations can be found in the formulary known to all pharmaceutical chemists: Remington's Pharmaceutical Sciences, Mack Publishing Company, Easton, Pa. These formulations include, for example, powders, pastes, ointments, jellies, waxes, oils, lipids, lipid (cationic or anionic) containing vesicles (such as LIPOFECTIN™, Life Technologies, Carlsbad, Calif.), DNA conjugates, anhydrous absorption pastes, oil-in-water and water-in-oil emulsions, emulsions carbowax (polyethylene glycols of various molecular weights), semi-solid gels, and semi-solid mixtures containing carbowax. See also Powell et al. "Compendium of excipients for parenteral formulations" PDA (1998) J Pharm Sci Technol 52:238-311.

The dose of antibody administered to a patient may vary depending upon the age and the size of the patient, target disease, conditions, route of administration, and the like. The preferred dose is typically calculated according to body weight or body surface area. In an adult patient, it may be advantageous to intravenously administer the antibody of the present invention normally at a single dose of about 0.01 to about 20 mg/kg body weight, more preferably about 0.02 to about 7, about 0.03 to about 5, or about 0.05 to about 3 mg/kg body weight. Depending on the severity of the condition, the frequency and the duration of the treatment can be adjusted. Effective dosages and schedules for administering anti-EGFRvIII antibodies may be determined empirically; for example, patient progress can be monitored by periodic assessment, and the dose adjusted accordingly. Moreover, interspecies scaling of dosages can be performed using well-known methods in the art (e.g., Mordenti et al., 1991, *Pharmaceut. Res.* 8:1351).

Various delivery systems are known and can be used to administer the pharmaceutical composition of the invention, e.g., encapsulation in liposomes, microparticles, microcapsules, recombinant cells capable of expressing the mutant viruses, receptor mediated endocytosis (see, e.g., Wu et al., 1987, J. Biol. Chem. 262:4429-4432). Methods of introduction include, but are not limited to, intradermal, intramuscular, intraperitoneal, intravenous, subcutaneous, intranasal, epidural, and oral routes. The composition may be administered by any convenient route, for example by infusion or bolus injection, by absorption through epithelial or mucocutaneous linings (e.g., oral mucosa, rectal and intestinal mucosa, etc.) and may be administered together with other biologically active agents. Administration can be systemic or local.

A pharmaceutical composition of the present invention can be delivered subcutaneously or intravenously with a standard needle and syringe. In addition, with respect to subcutaneous delivery, a pen delivery device readily has applications in delivering a pharmaceutical composition of the present invention. Such a pen delivery device can be reusable or disposable. A reusable pen delivery device generally utilizes a replaceable cartridge that contains a pharmaceutical composition. Once all of the pharmaceutical composition within the cartridge has been administered and the cartridge is empty, the empty cartridge can readily be discarded and replaced with a new cartridge that contains the pharmaceutical composition. The pen delivery device can then be reused. In a disposable pen delivery device, there is no replaceable cartridge. Rather, the disposable pen delivery device comes prefilled with the pharmaceutical composition held in a reservoir within the device. Once the reservoir is emptied of the pharmaceutical composition, the entire device is discarded.

Numerous reusable pen and autoinjector delivery devices have applications in the subcutaneous delivery of a pharmaceutical composition of the present invention. Examples include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, Ind.), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, N.J.), OPTIPEN™, OPTIPEN PRO™, OPTIPEN STARLET™, and OPTICLIK™ (sanofi-aventis, Frankfurt, Germany), to name only a few. Examples of disposable pen delivery devices having applications in subcutaneous delivery of a pharmaceutical composition of the present invention include, but are not limited to the SOLOSTAR™ pen (sanofi-aventis), the FLEXPEN™ (Novo Nordisk), and the KWIKPEN™ (Eli Lilly), the SURECLICK™ Autoinjector (Amgen, Thousand Oaks, Calif.), the PENLET™ (Haselmeier, Stuttgart, Germany), the EPIPEN (Dey, L. P.), and the HUMIRA™ Pen (Abbott Labs, Abbott Park Ill.), to name only a few.

In certain situations, the pharmaceutical composition can be delivered in a controlled release system. In one embodiment, a pump may be used (see Langer, supra; Sefton, 1987, CRC Crit. Ref. Biomed. Eng. 14:201). In another embodiment, polymeric materials can be used; see, Medical Applications of Controlled Release, Langer and Wise (eds.), 1974, CRC Pres., Boca Raton, Fla. In yet another embodiment, a controlled release system can be placed in proximity of the composition's target, thus requiring only a fraction of the systemic dose (see, e.g., Goodson, 1984, in Medical Applications of Controlled Release, supra, vol. 2, pp. 115-138). Other controlled release systems are discussed in the review by Langer, 1990, Science 249:1527-1533.

The injectable preparations may include dosage forms for intravenous, subcutaneous, intracutaneous and intramuscular injections, drip infusions, etc. These injectable preparations may be prepared by methods publicly known. For example, the injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injection thus prepared is preferably filled in an appropriate ampoule.

Advantageously, the pharmaceutical compositions for oral or parenteral use described above are prepared into dosage forms in a unit dose suited to fit a dose of the active ingredients. Such dosage forms in a unit dose include, for example, tablets, pills, capsules, injections (ampoules), suppositories, etc. The amount of the aforesaid antibody contained is generally about 5 to about 500 mg per dosage form in a unit dose; especially in the form of injection, it is preferred that the aforesaid antibody is contained in about 5 to about 100 mg and in about 10 to about 250 mg for the other dosage forms.

Therapeutic Uses of the Antibodies

The present invention includes methods comprising administering to a subject in need thereof a therapeutic composition comprising an anti-EGFRvIII antibody or an antibody-drug conjugate comprising an anti-EGFRvIII antibody (e.g., an anti-EGFRvIII antibody or ADC comprising any of the HCVR/LCVR or CDR sequences as set forth in Table 1 herein). The therapeutic composition can comprise any of the anti-EGFRvIII antibodies, antigen-binding fragments thereof, or ADCs disclosed herein, and a pharmaceutically acceptable carrier or diluent.

The antibodies and ADCs of the invention are useful, inter alia, for the treatment, prevention and/or amelioration of any disease or disorder associated with or mediated by EGFRvIII expression or activity, or treatable by blocking the interaction between EGFRvIII and an EGFR ligand or otherwise inhibiting EGFRvIII activity and/or signaling, and/or promoting receptor internalization and/or decreasing cell surface receptor number. For example, the antibodies and ADCs of the present invention are useful for the treatment of tumors that express EGFRvIII and/or that respond to ligand-mediated signaling. The antibodies and antigen-binding fragments of the present invention may also be used to treat primary and/or metastatic tumors arising in the brain and meninges, oropharynx, lung and bronchial tree, gastrointestinal tract, male and female reproductive tract, muscle, bone, skin and appendages, connective tissue, spleen, immune system, blood forming cells and bone marrow, liver and urinary tract, and special sensory organs such as the eye. In certain embodiments, the antibodies and ADCs of the invention are used to treat one or more of the following cancers: renal cell carcinoma, pancreatic carcinoma, head and neck cancer, prostate cancer, malignant gliomas, osteosarcoma, colorectal cancer, gastric cancer (e.g., gastric cancer with MET amplification), malignant mesothelioma, multiple myeloma, ovarian cancer, small cell lung cancer, non-small cell lung cancer, synovial sarcoma, thyroid cancer, breast cancer, or melanoma.

In the context of the methods of treatment described herein, the anti-EGFRvIII antibody may be administered as a monotherapy (i.e., as the only therapeutic agent) or in combination with one or more additional therapeutic agents (examples of which are described elsewhere herein).

According to specific embodiments, the present invention provides methods for treating a cancer, reducing tumor growth and/or causing tumor regression in a patient. The methods according to this aspect of the invention comprise administering to a patient a first antibody-drug conjugate (ADC) either alone or in combination with a second anti-EGFRvIII antibody or ADC. The first ADC will typically comprise an antibody or antigen-binding fragment of an antibody and a cytotoxin, wherein the antibody or antigen-binding fragment of the first ADC specifically binds EGFRvIII but does not bind the junctional EGFRvIII peptide of SEQ ID NO:148 or the peptide of SEQ ID NO:165 (i.e., the first ADC comprises a conformational EGFRvIII-binding antibody). In embodiments in which a second antibody or ADC is administered, the second antibody or ADC will typically comprise an antibody or antigen-binding fragment of an antibody and a cytotoxin, wherein the second antibody or antigen-binding fragment specifically binds EGFRvIII and also binds the junctional EGFRvIII peptide of SEQ ID NO:148 and/or the peptide of SEQ ID NO:165 (i.e., the second antibody or ADC comprises an EGFRvIII junctional peptide-binding antibody). When two separate anti-EGFRvIII ADCs are used in the context of this aspect of the invention, both ADCs may, in certain embodiments, comprise the same cytotoxic agent or same class of cytotoxic agent. In other embodiments where two separate anti-EGFRvIII ADCs are used, each ADC may comprise a different cytotoxic agent and/or a different class of cytotoxic agent. Non-limiting exemplary embodiments of this aspect of the invention are set forth herein at Example 14. According to certain embodiments, the antibody or antigen-binding fragment of the first ADC (i.e., the conformational EGFRvIII binding antibody) comprises heavy and light chain complementarity determining regions comprising SEQ ID NOs: 36, 38, 40, 44, 46, and 48, or the heavy chain variable region comprising SEQ ID NO: 34 and a light chain variable region comprising SEQ ID NO:42.

Combination Therapies and Formulations

The present invention includes compositions and therapeutic formulations comprising any of the anti-EGFRvIII antibodies described herein in combination with one or more additional therapeutically active components, and methods of treatment comprising administering such combinations to subjects in need thereof.

The anti-EGFRvIII antibodies of the present invention may be co-formulated with and/or administered in combination with one or more additional therapeutically active component(s) selected from the group consisting of: a PRLR antagonist (e.g., an anti-PRLR antibody or small molecule inhibitor of PRLR), an EGFR antagonist (e.g., an anti-EGFR antibody [e.g., cetuximab or panitumumab] or small molecule inhibitor of EGFR [e.g., gefitinib or erlotinib]), an antagonist of another EGFR family member such as Her2/ErbB2, ErbB3 or ErbB4 (e.g., anti-ErbB2 [e.g., trastuzumab or T-DM1 {KADCYLA®}], anti-ErbB3 or anti-ErbB4 antibody or small molecule inhibitor of ErbB2, ErbB3 or ErbB4 activity), a cMET antagonist (e.g., an anti-cMET antibody), an IGF1R antagonist (e.g., an anti-IGF1R antibody), a B-raf inhibitor (e.g., vemurafenib, sorafenib, GDC-0879, PLX-4720), a PDGFR-α inhibitor (e.g., an anti-PDGFR-α antibody), a PDGFR-β inhibitor (e.g., an anti-PDGFR-β antibody or small molecule kinase inhibitor such as, e.g., imatinib mesylate or sunitinib malate), a PDGF ligand inhibitor (e.g., anti-PDGF-A, —B, —C, or —D antibody, aptamer, siRNA, etc.), a VEGF antagonist (e.g., a VEGF-Trap such as aflibercept, see, e.g., U.S. Pat. No. 7,087,411 (also referred to herein as a "VEGF-inhibiting fusion protein"), anti-VEGF antibody (e.g., bevacizumab), a small molecule kinase inhibitor of VEGF receptor (e.g., sunitinib, sorafenib or pazopanib)), a DLL4 antagonist (e.g., an anti-DLL4 antibody disclosed in US 2009/0142354 such as REGN421), an Ang2 antagonist (e.g., an anti-Ang2 antibody disclosed in US 2011/0027286 such as H1H685P), a FOLH1 antagonist (e.g., an anti-FOLH1 antibody), a STEAP1 or STEAP2 antagonist (e.g., an anti-STEAP1 antibody or an anti-STEAP2 antibody), a TMPRSS2 antagonist (e.g., an anti-TMPRSS2 antibody), a MSLN antagonist (e.g., an anti-MSLN antibody), a CA9 antagonist (e.g., an anti-CA9 antibody), a uroplakin antagonist (e.g., an anti-uroplakin [e.g., anti-UPK3A] antibody), a MUC16 antagonist (e.g., an anti-MUC16 antibody), a Tn antigen antagonist (e.g., an anti-Tn antibody), a CLEC12A antagonist (e.g., an anti-CLEC12A antibody), a TNFRSF17 antagonist (e.g., an anti-TNFRSF17 antibody), a LGR5 antagonist (e.g., an anti-LGR5 antibody), a monovalent CD20 antagonist (e.g., a monovalent anti-CD20 antibody such as rituximab), a PD-1 antibody, a PD-L1 antibody, a CD3 antibody, a CTLA-4 antibody etc. Other agents that may be beneficially administered in combination with the bispecific antigen-binding molecules of the invention include, e.g., tamoxifen, aromatase inhibitors, and cytokine inhibitors, including small-molecule cytokine inhibitors and antibodies that bind to cytokines such as IL-1, IL-2, IL-3, IL-4, IL-5, IL-6, IL-8, IL-9, IL-11, IL-12, IL-13, IL-17, IL-18, or to their respective receptors.

The present invention includes compositions and therapeutic formulations comprising any of the anti-EGFRvIII antibodies described herein in combination with one or more chemotherapeutic agents. Examples of chemotherapeutic agents include alkylating agents such as thiotepa and cyclosphosphamide (Cytoxan™); alkyl sulfonates such as busulfan, improsulfan and piposulfan; aziridines such as benzodopa, carboquone, meturedopa, and uredopa; ethylenimines and methylamelamines including altretamine, triethylenemelamine, trietylenephosphoramide, triethylenethiophosphaoramide and trimethylolomelamine; nitrogen mustards such as chlorambucil, chlornaphazine, cholophosphamide, estramustine, ifosfamide, mechlorethamine, mechlorethamine oxide hydrochloride, melphalan, novembichin, phenesterine, prednimustine, trofosfamide, uracil mustard; nitrosureas such as carmustine, chlorozotocin, fotemustine, lomustine, nimustine, ranimustine; antibiotics such as aclacinomysins, actinomycin, authramycin, azaserine, bleomycins, cactinomycin, calicheamicin, carabicin, carminomycin, carzinophilin, chromomycins, dactinomycin, daunorubicin, detorubicin, 6-diazo-5-oxo-L-norleucine, doxorubicin, epirubicin, esorubicin, idarubicin, marcellomycin, mitomycins, mycophenolic acid, nogalamycin, olivomycins, peplomycin, potfiromycin, puromycin, quelamycin, rodorubicin, streptonigrin, streptozocin, tubercidin, ubenimex, zinostatin, zorubicin; anti-metabolites such as methotrexate and 5-fluorouracil (5-FU); folic acid analogues such as denopterin, methotrexate, pteropterin, trimetrexate; purine analogs such as fludarabine, 6-mercaptopurine, thiamiprine, thioguanine; pyrimidine analogs such as ancitabine, azacitidine, 6-azauridine, carmofur, cytarabine, dideoxyuridine, doxifluridine, enocitabine, floxuridine; androgens such as calusterone, dromostanolone propionate, epitiostanol, mepitiostane, testolactone; anti-adrenals such as aminoglutethimide, mitotane, trilostane; folic acid replenisher such as frolinic acid; aceglatone; aldophosphamide glycoside; aminolevulinic acid; amsacrine; bestrabucil; bisantrene; edatraxate; defofamine; demecolcine; diaziquone; elfornithine; elliptinium acetate; etoglucid; gallium nitrate; hydroxyurea; lentinan; lonidamine; mitoguazone; mitoxantrone; mopidamol; nitracrine; pentostatin; phenamet; pirarubicin; podophyllinic acid; 2-ethylhydrazide; procarbazine; PSK™; razoxane; sizofiran; spirogermanium; tenuazonic acid; triaziquone; 2,2',2''-trichlorotriethylamine; urethan; vindesine; dacarbazine; mannomustine; mitobronitol; mitolactol; pipobroman; gacytosine; arabinoside ("Ara-C"); cyclophosphamide; thiotepa; taxanes, e.g. paclitaxel (Taxol™, Bristol-Myers Squibb Oncology, Princeton, N.J.) and docetaxel (Taxotere™; Aventis Antony, France); chlorambucil; gemcitabine; 6-thioguanine; mercaptopurine; methotrexate; platinum analogs such as cisplatin and carboplatin; vinblastine; platinum; etoposide (VP-16); ifosfamide; mitomycin C; mitoxantrone; vincristine; vinorelbine; navelbine; novantrone; teniposide; daunomycin; aminopterin; xeloda; ibandronate; CPT-11; topoisomerase inhibitor RFS 2000; difluoromethylornithine (DMFO); retinoic acid; esperamicins; capecitabine; and pharmaceutically acceptable salts, acids or derivatives of any of the above. Also included in this definition are anti-hormonal agents that act to regulate or inhibit hormone action on tumors such as anti-estrogens including for example tamoxifen, raloxifene, aromatase inhibiting 4(5)-imidazoles, 4-hydroxytamoxifen, trioxifene, keoxifene, LY 117018, onapristone, and toremifene (Fareston); and anti-androgens such as flutamide, nilutamide, bicalutamide, leuprolide, and goserelin; and pharmaceutically acceptable salts, acids or derivatives of any of the above.

The anti-EGFRvIII antibodies of the invention may also be administered and/or co-formulated in combination with antivirals, antibiotics, analgesics, corticosteroids, steroids, oxygen, antioxidants, COX inhibitors, cardioprotectants, metal chelators, IFN-gamma, and/or NSAIDs.

The additional therapeutically active component(s), e.g., any of the agents listed above or derivatives thereof, may be administered just prior to, concurrent with, or shortly after the administration of an anti-EGFRvIII antibody of the present invention; (for purposes of the present disclosure, such administration regimens are considered the administration of an anti-EGFRvIII antibody "in combination with" an additional therapeutically active component). The present invention includes pharmaceutical compositions in which an anti-EGFRvIII antibody of the present invention is co-formulated with one or more of the additional therapeutically active component(s) as described elsewhere herein.

Administration Regimens

According to certain embodiments of the present invention, multiple doses of an anti-EGFRvIII antibody (or a pharmaceutical composition comprising a combination of an anti-EGFRvIII antibody and any of the additional therapeutically active agents mentioned herein) may be administered to a subject over a defined time course. The methods according to this aspect of the invention comprise sequentially administering to a subject multiple doses of an anti-EGFRvIII antibody of the invention. As used herein, "sequentially administering" means that each dose of anti-EGFRvIII antibody is administered to the subject at a different point in time, e.g., on different days separated by a predetermined interval (e.g., hours, days, weeks or months). The present invention includes methods which comprise sequentially administering to the patient a single initial dose of an anti-EGFRvIII antibody, followed by one or more secondary doses of the anti-EGFRvIII antibody, and optionally followed by one or more tertiary doses of the anti-EGFRvIII antibody.

The terms "initial dose," "secondary doses," and "tertiary doses," refer to the temporal sequence of administration of the anti-EGFRvIII antibody of the invention. Thus, the "initial dose" is the dose which is administered at the beginning of the treatment regimen (also referred to as the "baseline dose"); the "secondary doses" are the doses which are administered after the initial dose; and the "tertiary doses" are the doses which are administered after the secondary doses. The initial, secondary, and tertiary doses may all contain the same amount of anti-EGFRvIII antibody, but generally may differ from one another in terms of frequency of administration. In certain embodiments, however, the amount of anti-EGFRvIII antibody contained in the initial, secondary and/or tertiary doses varies from one another (e.g., adjusted up or down as appropriate) during the course of treatment. In certain embodiments, two or more (e.g., 2, 3, 4, or 5) doses are administered at the beginning of the treatment regimen as "loading doses" followed by subsequent doses that are administered on a less frequent basis (e.g., "maintenance doses").

In certain exemplary embodiments of the present invention, each secondary and/or tertiary dose is administered 1 to 26 (e.g., 1, 1½, 2, 2½, 3, 3½, 4, 4½, 5, 5½, 6, 6½, 7, 7½, 8, 8½, 9, 9½, 10, 10½, 11, 11½, 12, 12½, 13, 13½, 14, 14½, 15, 15½, 16, 16½, 17, 17½, 18, 18½, 19, 19½, 20, 20½, 21, 21½, 22, 22½, 23, 23½, 24, 24½, 25, 25½, 26, 26½, or more) weeks after the immediately preceding dose. The phrase "the immediately preceding dose," as used herein, means, in a sequence of multiple administrations, the dose of anti-EGFRvIII antibody which is administered to a patient prior to the administration of the very next dose in the sequence with no intervening doses.

The methods according to this aspect of the invention may comprise administering to a patient any number of secondary and/or tertiary doses of an anti-EGFRvIII antibody. For example, in certain embodiments, only a single secondary dose is administered to the patient. In other embodiments, two or more (e.g., 2, 3, 4, 5, 6, 7, 8, or more) secondary doses are administered to the patient. Likewise, in certain embodiments, only a single tertiary dose is administered to the patient. In other embodiments, two or more (e.g., 2, 3, 4, 5, 6, 7, 8, or more) tertiary doses are administered to the patient. The administration regimen may be carried out indefinitely over the lifetime of a particular subject, or until such treatment is no longer therapeutically needed or advantageous.

In embodiments involving multiple secondary doses, each secondary dose may be administered at the same frequency as the other secondary doses. For example, each secondary dose may be administered to the patient 1 to 2 weeks or 1 to 2 months after the immediately preceding dose. Similarly, in embodiments involving multiple tertiary doses, each tertiary dose may be administered at the same frequency as the other tertiary doses. For example, each tertiary dose may be administered to the patient 2 to 12 weeks after the immediately preceding dose. In certain embodiments of the invention, the frequency at which the secondary and/or tertiary doses are administered to a patient can vary over the course of the treatment regimen. The frequency of administration may also be adjusted during the course of treatment by a physician depending on the needs of the individual patient following clinical examination.

The present invention includes administration regimens in which 2 to 6 loading doses are administered to a patient at a first frequency (e.g., once a week, once every two weeks, once every three weeks, once a month, once every two months, etc.), followed by administration of two or more maintenance doses to the patient on a less frequent basis. For example, according to this aspect of the invention, if the loading doses are administered at a frequency of once a month, then the maintenance doses may be administered to the patient once every six weeks, once every two months, once every three months, etc.

Diagnostic Uses of the Antibodies

The anti-EGFRvIII antibodies of the present invention may also be used to detect and/or measure EGFRvIII, or EGFRvIII-expressing cells in a sample, e.g., for diagnostic purposes. For example, an anti-EGFRvIII antibody, or fragment thereof, may be used to diagnose a condition or disease characterized by aberrant expression (e.g., over-expression, under-expression, lack of expression, etc.) of EGFRvIII. Exemplary diagnostic assays for EGFRvIII may comprise, e.g., contacting a sample, obtained from a patient, with an anti-EGFRvIII antibody of the invention, wherein the anti-EGFRvIII antibody is labeled with a detectable label or reporter molecule. Alternatively, an unlabeled anti-EGFRvIII antibody can be used in diagnostic applications in combination with a secondary antibody which is itself detectably labeled. The detectable label or reporter molecule can be a radioisotope, such as $^{3}$H, $^{14}$C, $^{32}$P, $^{35}$S, or $^{125}$I; a fluorescent or chemiluminescent moiety such as fluorescein isothiocyanate, or rhodamine; or an enzyme such as alkaline phosphatase, beta-galactosidase, horseradish peroxidase, or luciferase. Specific exemplary assays that can be used to detect or measure EGFRvIII in a sample include enzyme-linked immunosorbent assay (ELISA), radioimmunoassay (RIA), and fluorescence-activated cell sorting (FACS).

Samples that can be used in EGFRvIII diagnostic assays according to the present invention include any tissue or fluid sample obtainable from a patient which contains detectable quantities of EGFRvIII protein, or fragments thereof, under normal or pathological conditions. Generally, levels of EGFRvIII in a particular sample obtained from a healthy patient (e.g., a patient not afflicted with a disease or condition associated with abnormal EGFRvIII levels or activity) will be measured to initially establish a baseline, or standard, level of EGFRvIII. This baseline level of EGFRvIII can then be compared against the levels of EGFRvIII measured in samples obtained from individuals suspected of having a EGFRvIII related disease or condition.

EXAMPLES

The following examples are put forth so as to provide those of ordinary skill in the art with a complete disclosure and description of how to make and use the methods and compositions of the invention, and are not intended to limit the scope of what the inventors regard as their invention. Efforts have been made to ensure accuracy with respect to numbers used but some experimental errors and deviations should be accounted for. Unless indicated otherwise, molecular weight is average molecular weight, temperature is in degrees Centigrade, and pressure is at or near atmospheric.

Example 1. Generation of Anti-EGFRvIII Antibodies

Anti-EGFRvIII antibodies were obtained by immunizing a VELOCIMMUNE® mouse (i.e., an engineered mouse comprising DNA encoding human immunoglobulin heavy and kappa light chain variable regions) with an immunogen comprising the extracellular domain of EGFRvIII. Antibodies of the first set include the antibodies designated as H1H2194P, H1H2195P, H2M1863N2, H2M1911N, H2M1912N, H2M1915N, H2M1917N, H2M1918N, and H3M1913N (as shown in Tables 1 and 2).

The antibody immune response was monitored by an EGFRvIII-specific immunoassay. When a desired immune response was achieved splenocytes were harvested and fused with mouse myeloma cells to preserve their viability and form hybridoma cell lines. The hybridoma cell lines were screened and selected to identify cell lines that produce EGFRvIII-specific antibodies. Using this technique several anti-EGFRvIII chimeric antibodies (i.e., antibodies possessing human variable domains and mouse constant domains) were obtained. In addition, several fully human anti-EGFRvIII antibodies were isolated directly from antigen-positive B cells without fusion to myeloma cells, as described in US 2007/0280945A1.

Separately, H1H1863N2 with reduced fucosylation ["H1H1863N2(Fuc−)"] was also prepared in a CHO host cell line that was described as "8088" in US Patent Application No. 2010/0304436A1, which is specifically incorporated by reference in its entirety. Briefly, the light chain and heavy chain sequences of H1H1863N2 were cloned into expression vectors. Two million 8088 cells were transfected with the light and heavy chain plasmids, and pR4004 vector containing the gene encoding Cre. Transfected cells that survived selection with 400 µg/ml hygromycin were adapted to grow in suspension in serum-free, fucose-free medium. Cells that expressed fluorescent protein EGFP but not DsRed or ECFP from the transfected cells were isolated by flow cytometry. The sorted cells were seeded in a shaker flask at $4\times10^{5}$ cells/ml and, three days later, the culture medium was collected and the antibody protein therein [i.e., H1H1863N2 (Fuc−)] was purified by Protein A chromatography. Mass spectrometry analysis of the resulting H1H1863N2(Fuc−) confirmed that core fucose was removed relative to the H1H1863N2(Fuc+), original antibody. The designations, "H1H1863N2" and "H1H1863N2(Fuc+)" herein, both indicate the original antibody without fucosylation modifications.

Certain biological properties of the exemplary anti-EGFRvIII antibodies generated in accordance with the methods of this Example are described in detail in the Examples set forth below.

Example 2. Heavy and Light Chain Variable Region Amino Acid and Nucleic Acid Sequences Table 1 sets forth the amino acid sequence identifiers of the heavy and light chain variable regions and CDRs of selected anti-EGFRvIII antibodies of the invention. The corresponding nucleic acid sequence identifiers are set forth in Table 2.

TABLE 1

Amino Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H2194P | 2 | 4 | 6 | 8 | 10 | 12 | 14 | 16 |
| H1H2195P | 18 | 20 | 22 | 24 | 26 | 28 | 30 | 32 |
| H2M1863N2 | 34 | 36 | 38 | 40 | 42 | 44 | 46 | 48 |
| H2M1911N | 50 | 52 | 54 | 56 | 58 | 60 | 62 | 64 |
| H2M1912N | 66 | 68 | 70 | 72 | 74 | 76 | 78 | 80 |
| H2M1915N | 82 | 84 | 86 | 88 | 90 | 92 | 94 | 96 |
| H2M1917N | 98 | 100 | 102 | 104 | 106 | 108 | 110 | 112 |
| H2M1918N | 114 | 116 | 118 | 120 | 122 | 124 | 126 | 128 |
| H3M1913N | 130 | 132 | 134 | 136 | 138 | 140 | 142 | 144 |

TABLE 2

Nucleic Acid Sequence Identifiers

| Antibody Designation | SEQ ID NOs: | | | | | | | |
|---|---|---|---|---|---|---|---|---|
| | HCVR | HCDR1 | HCDR2 | HCDR3 | LCVR | LCDR1 | LCDR2 | LCDR3 |
| H1H2194P | 1 | 3 | 5 | 7 | 9 | 11 | 13 | 15 |
| H1H2195P | 17 | 19 | 21 | 23 | 25 | 27 | 29 | 31 |
| H2M1863N2 | 33 | 35 | 37 | 39 | 41 | 43 | 45 | 47 |
| H2M1911N | 49 | 51 | 53 | 55 | 57 | 59 | 61 | 63 |
| H2M1912N | 65 | 67 | 69 | 71 | 73 | 75 | 77 | 79 |
| H2M1915N | 81 | 83 | 85 | 87 | 89 | 91 | 93 | 95 |
| H2M1917N | 97 | 99 | 101 | 103 | 105 | 107 | 109 | 111 |
| H2M1918N | 113 | 115 | 117 | 119 | 121 | 123 | 125 | 127 |
| H3M1913N | 129 | 131 | 133 | 135 | 137 | 139 | 141 | 143 |

Antibodies are typically referred to herein according to the following nomenclature: Fc prefix (e.g. "H1H," "H2M," "H3M," etc.), followed by a numerical identifier (e.g. "2194," "2195," "1863," etc.), followed by a "P" or "N" suffix, as shown in Tables 1 and 2. Thus, according to this nomenclature, an antibody may be referred to herein as, e.g., "H1H2194N," "H2M1911N," "H3M1913N," etc. The H1H, H2M and H3M prefixes on the antibody designations used herein indicate the particular Fc region isotype of the antibody. For example, an "H1H" antibody has a human IgG1 Fc, an "H2M" antibody has a mouse IgG2 Fc, and an "H3M" antibody has a mouse IgG3 Fc, (all variable regions are fully human as denoted by the first 'H' in the antibody designation). As will be appreciated by a person of ordinary skill in the art, an antibody having a particular Fc isotype can be converted to an antibody with a different Fc isotype (e.g., an antibody with a mouse IgG1 Fc can be converted to an antibody with a human IgG4, etc.), but in any event, the variable domains (including the CDRs)—which are indicated by the numerical identifiers shown in Tables 1 and 2—will remain the same, and the binding properties are expected to be identical or substantially similar regardless of the nature of the Fc domain.

Control Constructs Used in the Following Examples

Control constructs were included in the following experiments for comparative purposes: Control I: Human anti-EGFRvIII antibody (IgG1) with heavy and light chain variable domains having the amino acid sequences corresponding to SEQ ID NOS:142 and 144, respectively, of the "13.1.2" antibody disclosed in U.S. Pat. No. 7,736,644; Control II: Chimeric anti-EGFRvIII antibody (hIgG1) with heavy and light chain variable domains having the amino acid sequences corresponding to SEQ ID NOS:11 and 12, respectively, of the "ch806" antibody disclosed in U.S. Pat. No. 7,589,180; Control III: Humanized anti-EGFRvIII antibody (hIgG1) with heavy and light chain variable domains having the amino acid sequences corresponding to SEQ ID NOS:42 and 47, respectively, of the "hu806" antibody disclosed in US Patent Application Publication No. 2010/0056762; Control IV: a chimeric anti-EGFR antibody with heavy and light chain variable domains having the amino acid sequences of the corresponding domains of "C225," as set forth in U.S. Pat. No. 7,060,808; and Control V: Human anti-EGFRvIII antibody (IgG1) with heavy and light chain variable domains having the amino acid sequences corresponding to SEQ ID NOS: 2 and 19, respectively, of the "131" antibody of U.S. Pat. No. 7,736,644 B2. The "13.1.2" antibody is known to be specific for the junctional peptide (SEQ ID NO:148) of EGFRvIII; and the "ch806" and "hu806" antibodies are known to bind to residues 311-326 (SEQ ID NO:165) of EGFR (SEQ ID NO:146), which is amplified or overexpressed, or residues 44-59 of EGFRvIII (SEQ ID NO:147).

Example 3. EGFRvIII Binding Affinity Determination

Binding affinities and kinetic constants of human monoclonal anti-EGFRvIII antibodies were determined by surface plasmon resonance at 37° C. Measurements were conducted on a T100 BIACORE™ instrument. Antibodies, expressed as human IgG1 Fc (i.e., "H1H" designations), were captured onto an anti-human Fc sensor surface (mAb-capture format), and soluble monomeric [EGFR-mmh (SEQ ID NO:154) and EGFRvIII-mmh (SEQ ID NO:152)] or dimeric [EGFR-mFc (SEQ ID NO:155) and EGFRvIII-mFc (SEQ ID NO:153)] proteins were injected over the surface. In the receptor-capture format, either EGFRvIII-mFc or EGFR-mFc, was captured on the BIACORE™ chip and the respective antibodies flowed over. Kinetic association ($k_a$) and dissociation ($k_d$) rate constants were determined by processing and fitting the data to a 1:1 binding model using Scrubber 2.0 curve fitting software. Binding dissociation equilibrium constants ($K_D$) and dissociative half-lives ($t_{1/2}$) were calculated from the kinetic rate constants as: $K_D$ (M)=$k_d/k_a$; and $t_{1/2}$ (min)=ln 2/(60*$k_d$).

Results are shown in Tables 3 and 4. NB=no binding under the conditions tested; NT=not tested.

TABLE 3

(Binding kinetics of human Fc antibodies)
Binding at 37° C./MAb-Capture Format

| Ab | Analyte | $k_a$ ($M^{-1}s^{-1}$) | $k_d$ ($s^{-1}$) | $K_D$ (M) | T½ |
|---|---|---|---|---|---|
| H1H1863N2 (Fuc+) | EGFRvIII-mmh | 1.97E+04 | 8.95E−03 | 4.54E−07 | 1.3 |
| | EGFR-mmh | NT | NT | NT | NT |
| | EGFRvIII-mFc | 7.28E+04 | 8.07E−04 | 1.11E−08 | 14 |
| | EGFR-mFc | NT | NT | NT | NT |
| H1H1863N2 (Fuc−) | EGFRvIII-mmh | 3.02E+04 | 1.02E−02 | 3.39E−07 | 1.1 |
| | EGFR-mmh | NB | NB | NB | NB |
| | EGFRvIII-mFc | 1.12E+05 | 6.42E−04 | 5.73E−09 | 18 |
| | EGFR-mFc | NB | NB | NB | NB |
| H1H1911N | EGFRvIII-mmh | NB | NB | NB | NB |
| | EGFR-mmh | NB | NB | NB | NB |
| | EGFRvIII-mFc | NB | NB | NB | NB |
| | EGFR-mFc | NB | NB | NB | NB |
| H1H1912N | EGFRvIII-mmh | 1.83E+04 | 1.64E−02 | 8.99E−07 | 0.7 |
| | EGFR-mmh | NB | NB | NB | NB |
| | EGFRvIII-mFc | 2.04E+04 | 9.71E−04 | 4.77E−08 | 12 |
| | EGFR-mFc | NB | NB | NB | NB |
| H1H1913N | EGFRvIII-mmh | 1.63E+02 | 1.14E−03 | 7.03E−06 | 10 |
| | EGFR-mmh | NB | NB | NB | NB |

TABLE 3-continued (Binding kinetics of human Fc antibodies)
Binding at 37° C./MAb-Capture Format

| Ab | Analyte | $k_a$ ($M^{-1}s^{-1}$) | $k_d$ ($s^{-1}$) | $K_D$ (M) | T½ |
|---|---|---|---|---|---|
| | EGFRvIII-mFc | 1.40E+04 | 3.16E−04 | 2.26E−08 | 37 |
| | EGFR-mFc | NB | NB | NB | NB |
| H1H1915N | EGFRvIII-mmh | NB | NB | NB | NB |
| | EGFR-mmh | NB | NB | NB | NB |
| | EGFRvIII-mFc | NB | NB | NB | NB |
| | EGFR-mFc | NB | NB | NB | NB |
| H1H2194P | EGFRvIII-mmh | 8.10E+04 | 1.37E−03 | 1.70E−08 | 8 |
| | EGFR-mmh | 7.60E+04 | 9.60E−04 | 1.26E−08 | 12 |
| | EGFRvIII-mFc | 9.54E+04 | 2.22E−04 | 2.33E−09 | 52 |
| | EGFR-mFc | 8.10E+04 | 1.99E−04 | 2.43E−09 | 58 |
| H1H2195P | EGFRvIII-mmh | 6.48E+04 | 6.94E−04 | 1.07E−08 | 17 |
| | EGFR-mmh | 5.66E+04 | 5.23E−04 | 9.20E−09 | 22 |
| | EGFRvIII-mFc | 1.02E+05 | 1.13E−04 | 1.10E−09 | 103 |
| | EGFR-mFc | 9.20E+04 | 1.89E−04 | 2.05E−09 | 61 |
| Control I | EGFRvIII-mmh | 1.29E+05 | 1.53E−01 | 1.19E−06 | 0.1 |
| | EGFR-mmh | NB | NB | NB | NB |
| | EGFRvIII-mFc | 7.15E+04 | 7.36E−03 | 1.03E−07 | 1.6 |
| | EGFR-mFc | NB | NB | NB | NB |
| Control II | EGFRvIII-mmh | 4.90E+04 | 7.33E−03 | 1.50E−07 | 2 |
| | EGFR-mmh | NB | NB | NB | NB |
| | EGFRvIII-mFc | 2.02E+05 | 4.08E−04 | 2.02E−09 | 28 |
| | EGFR-mFc | NB | NB | NB | NB |
| Control III | EGFRvIII-mmh | 8.57E+04 | 5.16E−03 | 6.02E−08 | 2.2 |
| | EGFR-mmh | NB | NB | NB | NB |
| | EGFRvIII-mFc | 2.52E+05 | 2.98E−04 | 1.18E−09 | 39 |
| | EGFR-mFc | NB | NB | NB | NB |
| Control V | EGFRvIII-mmh | 1.94E+05 | 1.59E−02 | 8.20E−08 | 1 |
| | EGFR-mmh | NB | NB | NB | NB |
| | EGFRvIII-mFc | 1.91E+05 | 3.71E−04 | 1.95E−09 | 31 |
| | EGFR-mFc | NT | NT | NT | NT |

TABLE 4

(Binding kinetics of human Fc antibodies)
Binding at 37° C./Receptor-Capture Format

| Ab | Receptor Captured | ka ($M^{-1}s^{-1}$) | kd ($s^{-1}$) | $K_D$ (M) | T½ |
|---|---|---|---|---|---|
| H1H1863N2 (Fuc+) | EGFRvIII-mFc | 9.00E+05 | 2.06E−04 | 2.30E−10 | 56 |
| | EGFR-mFc | 2.11E+05 | 1.82E−01 | 8.65E−07 | 0.1 |
| H1H1863N2 (Fuc−) | EGFRvIII-mFc | 1.01E+06 | 2.15E−04 | 2.10E−10 | 54 |
| | EGFR-mFc | 1.99E+05 | 4.67E−01 | 2.34E−06 | 0.02 |
| H1H1911N | EGFRvIII-mFc | 3.29E+04 | 6.43E−04 | 1.95E−08 | 18 |
| | EGFR-mFc | 7.77E+03 | 1.74E−03 | 2.24E−07 | 7 |
| H1H1912N | EGFRvIII-mFc | 9.90E+04 | 5.37E−04 | 5.40E−09 | 22 |
| | EGFR-mFc | 3.99E+04 | 9.14E−04 | 2.29E−08 | 13 |
| H1H1913N | EGFRvIII-mFc | 6.30E+04 | 1.00E−06 | 1.58E−11 | 11550 |
| | EGFR-mFc | 5.93E+03 | 1.00E−06 | 1.69E−10 | 11550 |
| H1H1915N | EGFRvIII-mFc | 1.00E+05 | 3.28E−04 | 3.20E−09 | 35 |
| | EGFR-mFc | 4.35E+04 | 8.01E−03 | 1.84E−07 | 1.4 |
| H1H2193N | EGFRvIII-mFc | 2.17E+05 | 5.85E−05 | 2.68E−10 | 197 |
| | EGFR-mFc | 2.04E+05 | 9.15E−05 | 4.47E−10 | 126 |
| H1H2194N | EGFRvIII-mFc | 1.88E+05 | 7.38E−05 | 3.94E−10 | 157 |
| | EGFR-mFc | 1.87E+05 | 7.07E−05 | 3.80E−10 | 163 |
| H1H2195N | EGFRvIII-mFc | 2.37E+05 | 2.53E−05 | 1.06E−10 | 456 |
| | EGFR-mFc | 2.25E+05 | 5.20E−05 | 2.31E−10 | 222 |
| Control I | EGFRvIII-mFc | 4.46E+05 | 4.04E−03 | 9.06E−09 | 2.9 |
| | EGFR-mFc | NB | NB | NB | NB |
| Control II | EGFRvIII-mFc | 1.25E+06 | 7.31E−05 | 5.90E−11 | 158 |
| | EGFR-mFc | 4.44E+05 | 1.46E−04 | 3.29E−10 | 79 |
| Control III | EGFRvIII-mFc | 1.49E+06 | 1.00E−06 | 6.70E−13 | 11550 |
| | EGFR-mFc | 2.86E+05 | 6.17E−05 | 2.15E−10 | 187 |

As shown in Tables 3 and 4, several antibodies showed selectivity for EGFRvIII and did not bind wild-type EGFR in the mAb-capture format. In the receptor capture format (Table 4) H1H863N2, H1H1915N and Control I showed the greatest selectivity.

Experiment 4: Antibody Specificity Determined by ELISA

To further characterize anti-hEGFRvIII mAbs, their binding specificity was examined by ELISA. Plates were coated with one of the following: EGFR-mmh (SEQ ID NO:154); EGFRvIII-mmh (SEQ ID NO:152); and a junctional peptide (J-peptide) (SEQ ID NO:148). For the junctional peptides that were linked to biotin either at C-terminal (SEQ ID NO:149) or N-terminal (SEQ ID NO:150) via a linker, plates were pre-coated with avidin. Also, coated was an irrelevant peptide (control peptide) with or without biotin at its N-terminal. Anti-EGFRvIII antibodies as well as an isotype control antibody were added to coated plates and allowed to incubate for 1 hour at 25° C. The plates were then washed and bound anti-EGFRvIII mAbs were detected with anti-human Fc antibodies conjugated with horse-radish peroxidase (HRP). Plates were developed with a tetra-methyl-benzidine (TMB) substrate solution to produce a colorimetric reaction and neutralized with sulfuric acid before reading absorbance at 450 nm on a VICTOR™ X5 plate reader. Data analysis used a sigmoidal dose-response model within PRISM™ software. The calculated $EC_{50}$ value, defined as 50% of antibody concentration required to develop maximal response, was used as an indicator of binding potency. The results are shown in Table 5. NT: Not tested. Controls I-III: As described above.

reduced and non-reduced conditions. EGFR-mmh (SEQ ID NO:154) or EGFRvIII-mmh (SEQ ID NO:152) was loaded onto Tris-Glycine SDS PAGE gels, run and then transferred to nitrocellulose. After blocking, membranes were cut in half and probed with either anti-EGFRvIII antibodies or anti-His antibody. Controls I and II are as described above.

Figure 1B:
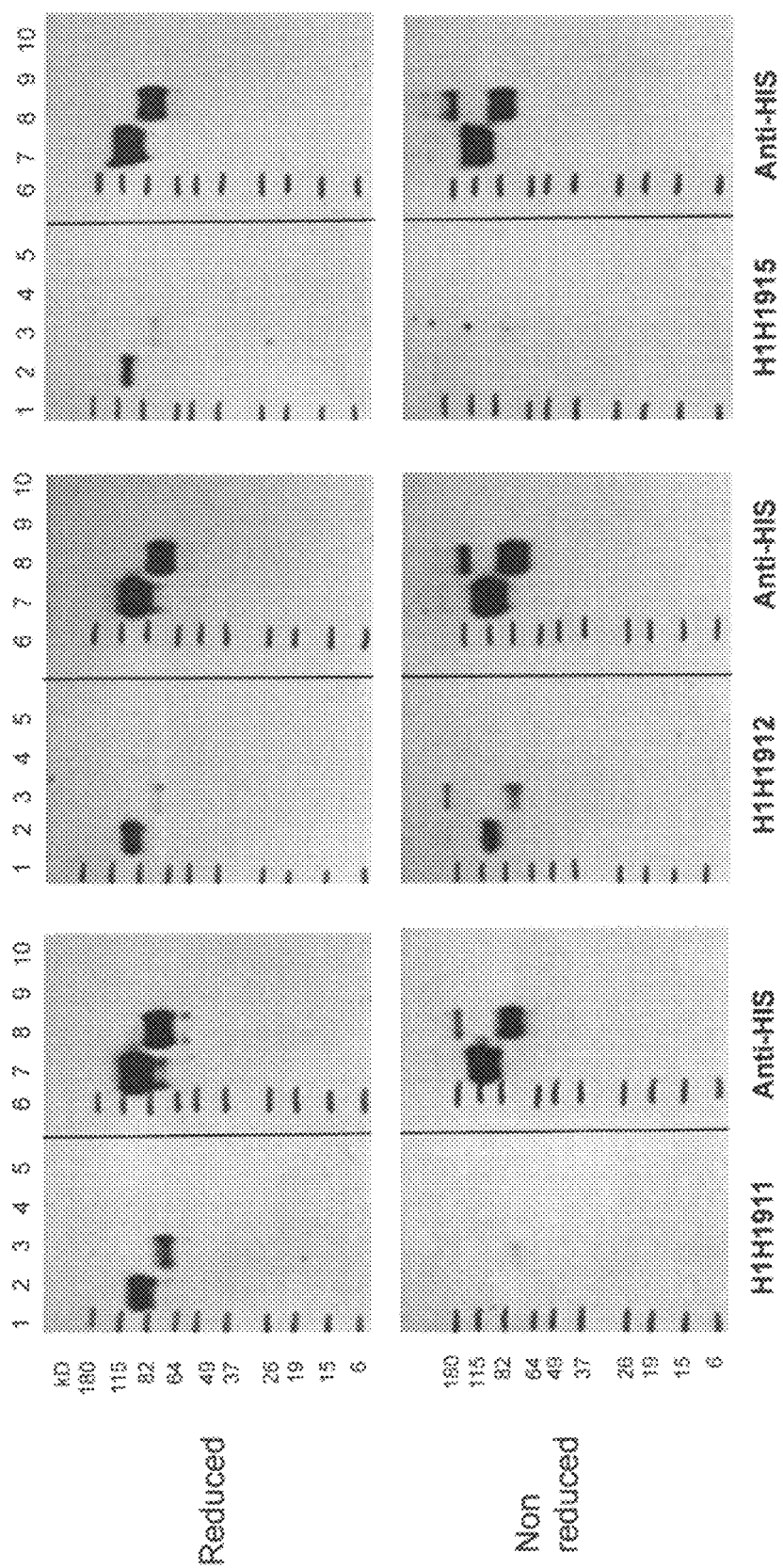

As shown in FIG. 1a, H1H1862N2 (Fuc−) does not bind reduced or non-reduced EGFRvIII-mmh or EGFR-mmh and thus has a conformational epitope to EGFRvIII. In contrast, Control II binds both wildtype and variant III EGFR under reduced and non-reduced conditions, while Control I, a junctional peptide binder, is specific for EGFRvIII. Both Control I and II, in contrast to H1H1863N2, have linear binding epitopes. FIG. 1b shows other EGFRvIII antibodies, which show mixed behaviors on Western blots.

Example 6: EGFR/EGFRvIII Peptide Binding and Antibody Competition Assays

H1H1863N2(Fuc−) was tested for its binding characteristics using peptide binding and antibody competition assays. For peptide binding experiments the EGFRvIII junctional peptide (SEQ ID NO:148) tagged via a linker with biotin at its C-terminus [i.e., LEEKKGNYVVTDHGGGGSK (SEQ ID NO:149)-biotin] or the peptide consisting of residues 311-326 of EGFR (the "EGFR 311-326 peptide"; SEQ ID NO:165) tagged via a linker with biotin at its C-terminus [i.e., CGADSYEMEEDGVRKCGGGGSK (SEQ ID NO:151)-biotin] were captured to ~0.4 nM of thickness using streptavidin coated OCTET® tips on a FORTEBIO® OCTET® RED instru-

TABLE 5

| | EC50 (nM) | | | | | | |
|---|---|---|---|---|---|---|---|
| Antibody | EGFR-mmh (25° C.) | EGFRvIII-mmh (25° C.) | J-peptide | C-term biotin J-peptide | N-term biotin J-peptide | Control peptide | N-term Biotin control peptide |
| H1H1863N2 (Fuc−) | >10 | 0.0766 | >10 | >10 | >10 | >10 | >10 |
| H1H1863N2 (Fuc+) | >10 | 0.113 | >10 | >10 | >10 | >10 | >10 |
| H1H1911N | 9.06 | 0.0748 | >10 | >10 | >10 | >10 | >10 |
| H1H1912N | 0.0405 | 0.0118 | >10 | >10 | >10 | >10 | >10 |
| H1H1913N | 2.55 | 2.14 | >10 | >10 | >10 | >10 | >10 |
| H1H1915N | >10 | 0.167 | >10 | >10 | >10 | >10 | >10 |
| H1H2193P | 0.0040 | 0.0035 | >10 | >10 | >10 | >10 | >10 |
| H1H2194P | 0.0037 | 0.0032 | >10 | >10 | >10 | >10 | >10 |
| H1H2195P | 0.0052 | 0.0049 | >10 | >10 | >10 | >10 | >10 |
| Control I | >10 | 0.0094 | 0.118 | 0.0153 | 0.0106 | >10 | >10 |
| Control II | 0.0095 | 0.0057 | >10 | >10 | >10 | >10 | >10 |
| Control III | 0.0079 | 0.0048 | NT | NT | NT | NT | NT |
| Isotype Control | >10 | >10 | >10 | >10 | >10 | >10 | >10 |

Antibodies H1H1863N2, H1H1915 and Control I showed strong binding to EGFRvIII but no binding (>10 nM) to wild-type EGFR. None of the antibodies, except Control I (having the sequences that correspond to the heavy and light chain sequences of the "13.1.2" antibody derived from mice immunized with junctional peptide (U.S. Pat. No. 7,736,644), showed binding to the junctional peptides.

Example 5: Western Blot of EGFR and EGFRvIII Using Anti-EGFRvIII Antibodies

Figure 2:
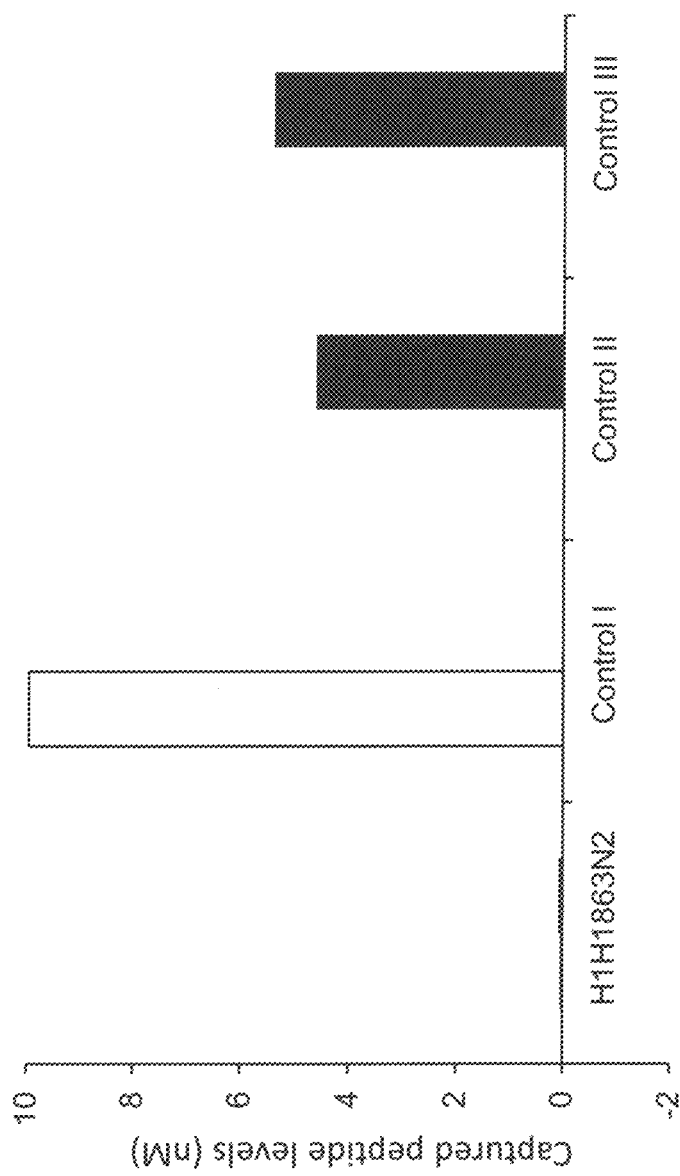
FIG. 2 shows the binding characteristics of H1H1863N2 (Fuc−). The EGFRvIII junctional peptide or the peptide of residues 311-326 of EGFR ("EGFR311-326 peptide"), each of which was tagged via a linker with biotin at the C-terminus, was captured to streptavidin-coated OCTET® tips on a FORTEBIO® OCTET® RED instrument and reacted with H1H1863N2(Fuc−) or Control I-III. Controls I and II: Same as above; and Control III: Humanized anti-EGFRvIII antibody (hIgG1) disclosed in US Patent Application Publication No. 2010/0056762. (□): C-terminal biotin-labeled EGFRvIII junctional peptide (SEQ ID NO:149); and (■): C-terminal biotin-labeled EGFR311-326 peptide (SEQ ID NO:151).

One of the antibodies, H1H1863N2, was tested for its binding characteristics with western blots under both ment. After peptide capture, the coated tips were placed in 1 μM solutions of antibody and the binding responses were recorded (see FIG. 2). Controls I-Ill are the same as those described above.

As predicted Control I bound the junctional peptide with C-terminal biotin and Controls II and III bound the EGFR 311-326 peptide with C-terminal biotin. H1H1863N2(Fuc−) failed to bind either of the peptides.

For antibody cross competition, ~200 resonance units (RU) of hEGFRvIII-mmh (SEQ ID NO:152) was captured onto a BIACORE™ surface coated with a high-density, anti-penta-Histidine polyclonal antibody (cat. #34660, QUIAGEN). Using a coinjection methodology, captured hEGFRvIII-mmh was saturated by a 5-minute injection of 500 nM of a first mAb immediately followed by another 5-minute injection of a second mAb (500 nM) which was supplemented with 500 nM of the first mAb. Significant binding, expressed as RU, of the second mAb was interpreted that it does not compete for binding with the first mAb. For control experiments isotype matched mAbs were used as either a first mAb or a second mAb. Results are shown in Table 6.

TABLE 6

| BIACORE™ Surface (First Antibody) | Second Antibody Binding (RU) | | | |
|---|---|---|---|---|
| | H1H1863N2 (Fuc−) Binding Response | Control I Binding Response | Control II Binding Response | Control III Binding Response |
| EGFRvIII alone | 270 | 234 | 247 | 247 |
| EGFRvIII - H1H1863N2(Fuc−) Complex | 5 | 253 | 191 | 208 |
| EGFRvIII - Control I Complex | 291 | 5 | 258 | 272 |
| EGFRvIII - Control II Complex | 225 | 252 | 6 | 25 |
| EGFRvIII - Control III Complex | 223 | 254 | 13 | 7 |

H1H1863N2(Fuc−) did not compete with any of control antibodies I-III for binding to the hEGFRvIII-mmh capture surface. As expected controls II and III, both of which are known to bind to residues 311-326 of EGFR, competed with each other for binding to the EGFRvIII-mmh capture surface.

Example 7: Cell Binding Selectivity of Anti-EGFRvIII Antibodies

To determine the specificity of the anti-EGFRvIII mAbs, their binding to HEK293, HEK293 cells expressing EGFRvIII (HEK293/EGFRvIII) and A431 cells, was analyzed by fluorescence activated cell sorting (FACS). HEK293/EGFRvIII cells were prepared by transfecting HEK293 cells with neomycin resistant DNA vectors constitutively expressing full-length hEGFRvIII (SEQ ID NO:147) using LIPOFECTAMINE™ 2000 transfection reagent (INVITROGEN™). At two days post-transfection, cells were placed under G418 selection for approximately two weeks. Populations positively expressing EGFRvIII were isolated via fluorescence activated cell sorting (FACS). The HEK293 cells expressing ~3×10$^6$ copies of EGFRvIII per cell were used in the experiment. Briefly, the anti-EGFRvIII antibodies at 10 μg/ml were incubated with cells for 30 minutes at room temperature, washed, incubated with secondary antibody, i.e., phycoerythrin (PE)-labeled goat F(ab')2 against human IgG (cat #109-116-170, Jackson ImmunoResearch Laboratories), followed by a final wash before FACS analysis. In another set of experiment, anti-EGFRvIII antibodies were directly conjugated via their lysine residues with the fluorescent dye, ALEXA FLUOR® 488 Dye (INVITROGEN™), thereby eliminating the step using the secondary antibody. The results from HEK293 cells and HEK293/EGFRvIII cells using directly labeled anti-EGFRvIII antibodies are shown in Table 7 and those using the secondary PE-labeled anti-Fc (human or mouse) are shown in Table 8. The results from A431 cells using directly labeled anti-EGFRvIII antibodies are shown in Table 9 and those using the secondary PE-labeled anti-Fc (human or mouse) are shown in Table 10. Controls I, II, III, IV and V are described above. MFI: Mean Fluorescence Intensity.

TABLE 7

| Antibody | Parental HEK293 MFI | HEK 293/ EGFRvIII MFI | Ratio (EGFRvIII MFI/ parental MFI) |
|---|---|---|---|
| Unstained | 3548 | 4005 | 1.1 |
| H1H1863N2 (Fuc−) | 3776 | 361000 | 95.6 |
| H1H1863N2 (Fuc+) | 3805 | 360000 | 94.6 |
| H1H1911N | 3593 | 55064 | 15.3 |
| H1H1912N | 3727 | 122000 | 32.7 |
| H1H1913N | 4801 | 239000 | 49.8 |
| H1H1915N | 3461 | 73413 | 21.2 |
| Control I | 3559 | 258000 | 72.5 |
| Control II | 3582 | 313000 | 87.4 |
| Control IV | 24954 | 439000 | 17.6 |

TABLE 8

| Antibody | Parental HEK293 MFI | HEK 293/ EGFRvIII MFI | Ratio (EGFRvIII MFI/ parental MFI) |
|---|---|---|---|
| Unstained | 819 | 920 | 1.1 |
| PE anti-human IgG | 1027 | 1106 | 1.1 |
| H1H1863N2 (Fuc−) | 1671 | 301000 | 180.1 |
| H1H1911N | 1812 | 107000 | 59.1 |
| H1H2194P | 981 | 18583 | 18.9 |
| H1H2195P | 1176 | 13517 | 11.5 |
| Control I | 1480 | 272000 | 183.8 |
| Control II | 1015 | 313000 | 308.4 |
| Control IV | 23325 | 354000 | 15.2 |
| Control V | 11732 | 997062 | 85.0 |

TABLE 9

| Antibody | A431 MFI | Fold Above Background |
|---|---|---|
| Unstained | 6708 | 1.0 |
| H1H1863N2 (Fuc−) | 26036 | 3.9 |
| H1H1911N | 15984 | 2.4 |
| H1H1912N | 14343 | 2.1 |
| H1H1915N | 8440 | 1.2 |
| Control I | 9652 | 1.4 |
| Control II | 15716 | 2.3 |
| Control III | 71514 | 10.7 |
| Control IV | 962000 | 143.4 |

TABLE 10

| Antibody | A431 MFI | Fold Above Background |
|---|---|---|
| Unstained | 1314 | 0.9 |
| PE anti-human IgG | 1428 | 1.0 |
| H1H1863N2 (Fuc−) | 3385 | 2.4 |
| H1H1911N | 3140 | 2.2 |
| H1H2194P | 2291 | 1.6 |
| H1H2195P | 2227 | 1.6 |
| Control I | 1448 | 1.0 |
| Control II | 5576 | 3.9 |
| Control IV | 395000 | 276.6 |
| Control V | 4240 | 3.0 |

Several anti-EGFRvIII antibodies showed a distinct binding preference for the HEK293/EGFRVIII cell line over the parental HEK293 cells when either detected using directly labeled anti-EGFRvIII antibodies (Table 7) or a secondary PE labeled anti-human IgG (Table 8). Most antibodies when incubated with A431 cells (30 minutes at 4° C.) displayed minimal to no binding, except for Controls III and IV antibodies (Tables 9 and 10).

Example 8: Internalization of Anti-EGFRvIII mAbs by HEK293/EGFRvIII Cells

Figure 3:
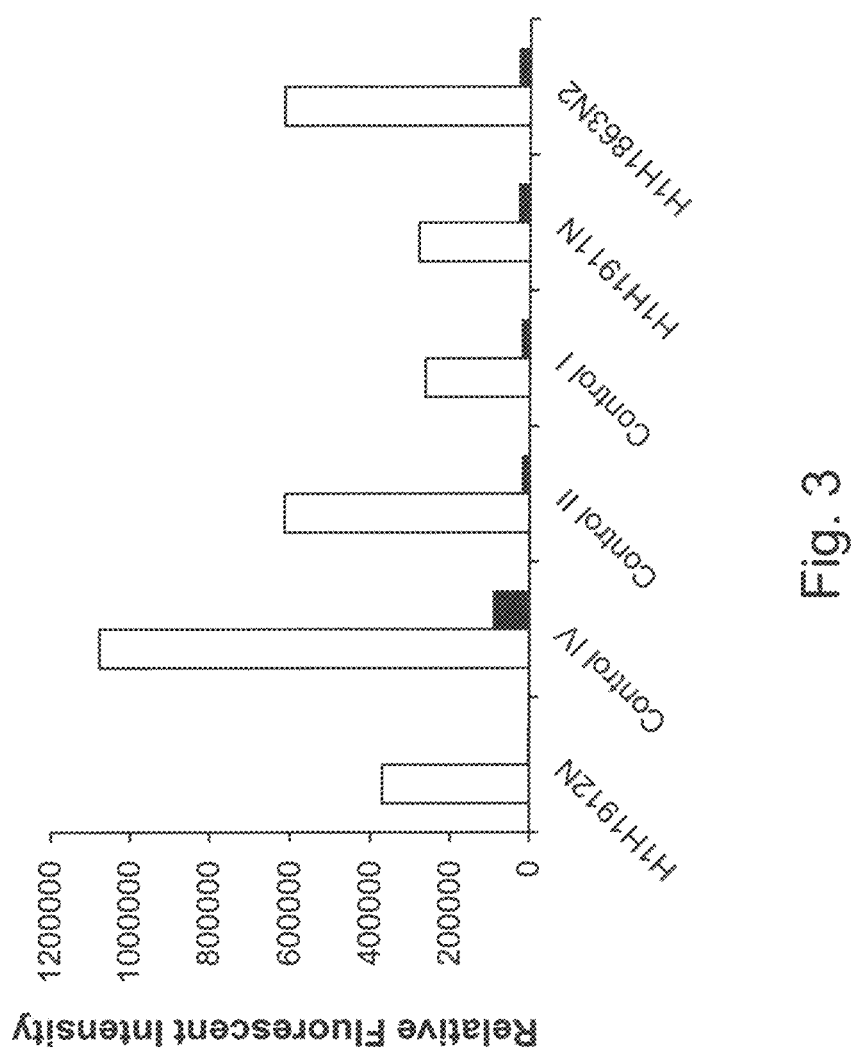
FIG. 3 shows the internalization of anti-EGFRvIII mAb by HEK293 cells expressing EGFRvIII (HEK293/EGFRvIII). Cell-surface bound anti-EGFRvIII antibodies and control antibodies were detected by dye-conjugated secondary antibody (Fab); images were acquired at 40× and internalized vesicles were quantitated. Controls I and II: Same as above; and Control IV: Chimeric anti-EGFR antibody disclosed in U.S. Pat. No. 7,060,808. (□): Internalization at 37° C.; and (■): Internalization at 4° C.

Anti-EGFRvIII mAbs (10 ug/ml) were incubated with HEK293/EGFRVIII (see Example 7, supra) cells for 2 hours on ice followed by two PBS washes. Cells were then subjected to a 30-min incubation on ice with secondary DYLIGHT™ 488-conjugated anti-human IgG Fab fragments (Jackson ImmunoResearch Laboratories) followed by two additional PBS washes. Antibodies were allowed to internalize for 1 h at 37° C. in internalization buffer (PBS+FBS) or remained at 4° C. Cells were fixed in 4% formaldehyde, and nuclei stained with DRAQ5® DNA dye (Cell Signaling Technology, Inc.). Images were acquired at 40× on the IMAGEXPRESS™ high content system (Molecular Devices) and internalized vesicles were quantitated using Columbus software (Perkin Elmer). The results are shown in Tables 11 and FIG. 3.

TABLE 11

| Ab | Fluorescent Intensity of vesicles 4° C. | | Fluorescent Intensity of vesicles 37° C. | |
| --- | --- | --- | --- | --- |
|  | Mean | ±SD | Mean | ±SD |
| H1H1863N2(Fuc−) | 29896 | 8333 | 617184 | 46823 |
| H1H1911N | 29834 | 11879 | 280439 | 61121 |
| H1H1912N | 4912 | 1774 | 370201 | 12205 |
| Control I | 21981 | 4613 | 263506 | 28067 |
| Control II | 20339 | 5644 | 615239 | 144397 |
| Control IV | 92311 | 19386 | 1078196 | 106073 |

Robust internalization occurred at 37° C. for H1H1863N2, Control II, and Control IV. Internalization was also observed for H1H1911N, H1H1912N and Control I.

Example 9: Binding of Anti-EGFRvIII Antibody to U87/EGFRvIII Tumor Xenograft To further determine the specificity of H1H1863N2, human glioblastoma cell line U87 expressing EGFRvIII was prepared as described for HEK293/EGFRvIII cells in Example 7. U87 cells expressing ~1.5×10$^5$ copies of EGFRvIII per cell (U87/EGFRvIII) were used in the experiment. U87/EGFRvIII cells (3×10$^6$ cells) were xenografted in severe combined immunodeficient (SCID) mice and tumors were allowed to grow until a median size of 200-300 mm$^3$ was obtained. Mice were then injected with H1H1863N2 (Fuc−) or isotype control via tail vein. At 10 minutes, 4 hours and 24 hours post injection of the antibody, mice were sacrificed and tumors were removed and placed into PBS. Tumors were immediately dissociated and stained with an allophycocyanin (APC)-conjugated anti-human Fc (hFc-APC) antibody. Stained cells were washed 3 times with flow PBS containing 2% fetal calf serum and 0.1% sodium azide. Tumors at the 10-min and 4-hour time points were fixed overnight and then measured by flow cytometer. Tumors collected at 24-hour time point were measured without being fixed. All samples were collected on an ACCURI® C6 FLOW CYTOMETER® (Accuri Cytometers, Inc.) and the mean fluorescence intensity (MFI) determined. The results are shown in Table 12. MFI values are the average of 2-3 biological replicates±the standard error of the mean (SEM).

TABLE 12

| | MFI ± SEM (U87/EGFRvIII) | |
| --- | --- | --- |
| Time Post-Injection | Isotype Control | H1H1863N2(Fuc−) |
| 10 minutes | 708 ± 4 | 2259 ± 115 |
| 4 hours | 741 ± 34 | 10620 ± 2881 |
| 24 hours | 664 ± 34 | 27923 ± 3297 |

Compared to isotype-control, H1H1863N2(Fuc−) antibody bound U87/EGFRvIII tumor cells efficiently in a time-dependent manner.

Figure 4A:
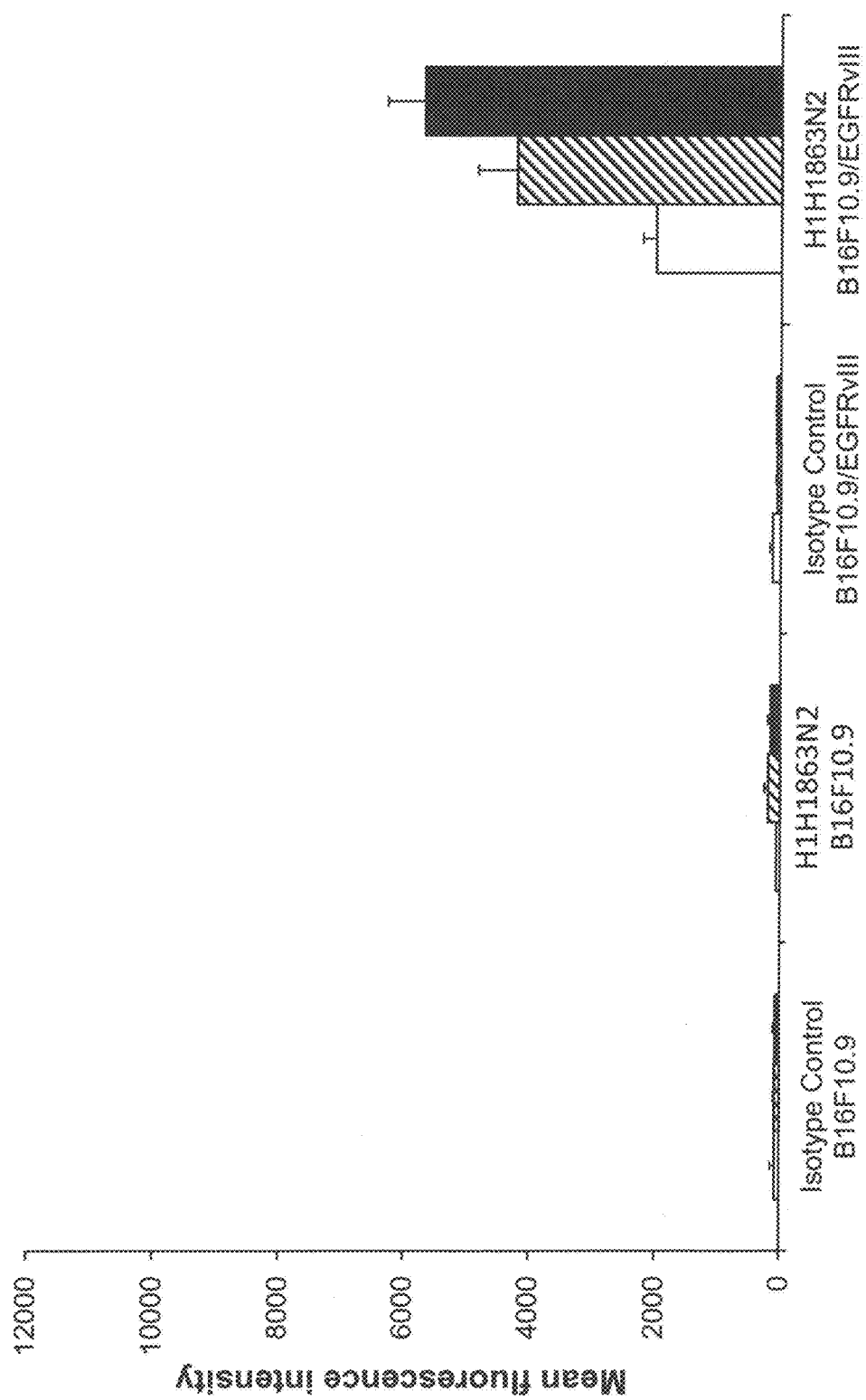
FIG. 4(a-b) shows the binding and internalization of anti-EGFRvIII antibody H1H1863N2(Fuc−) by B16F10.9 tumors or B16F10.9 tumors expressing EGFRvIII (B16F10.9/EGFRvIII) that were xenografted in severe combined immunodeficient (SCID) mice. Cell-surface bound (FIG. 4a) or cell-surface-bound plus internalized (FIG. 4b) anti-EGFRvIII antibody or isotype control antibody, was detected by allophycocyanin conjugated anti-human Fc (hFc-APC) antibody using flow cytometry. Mean fluorescent intensities (MIF) at 10 minutes (□), 4 hours (▨), and 24 hours (■), post-antibody injection, are shown.
Figure 4B:
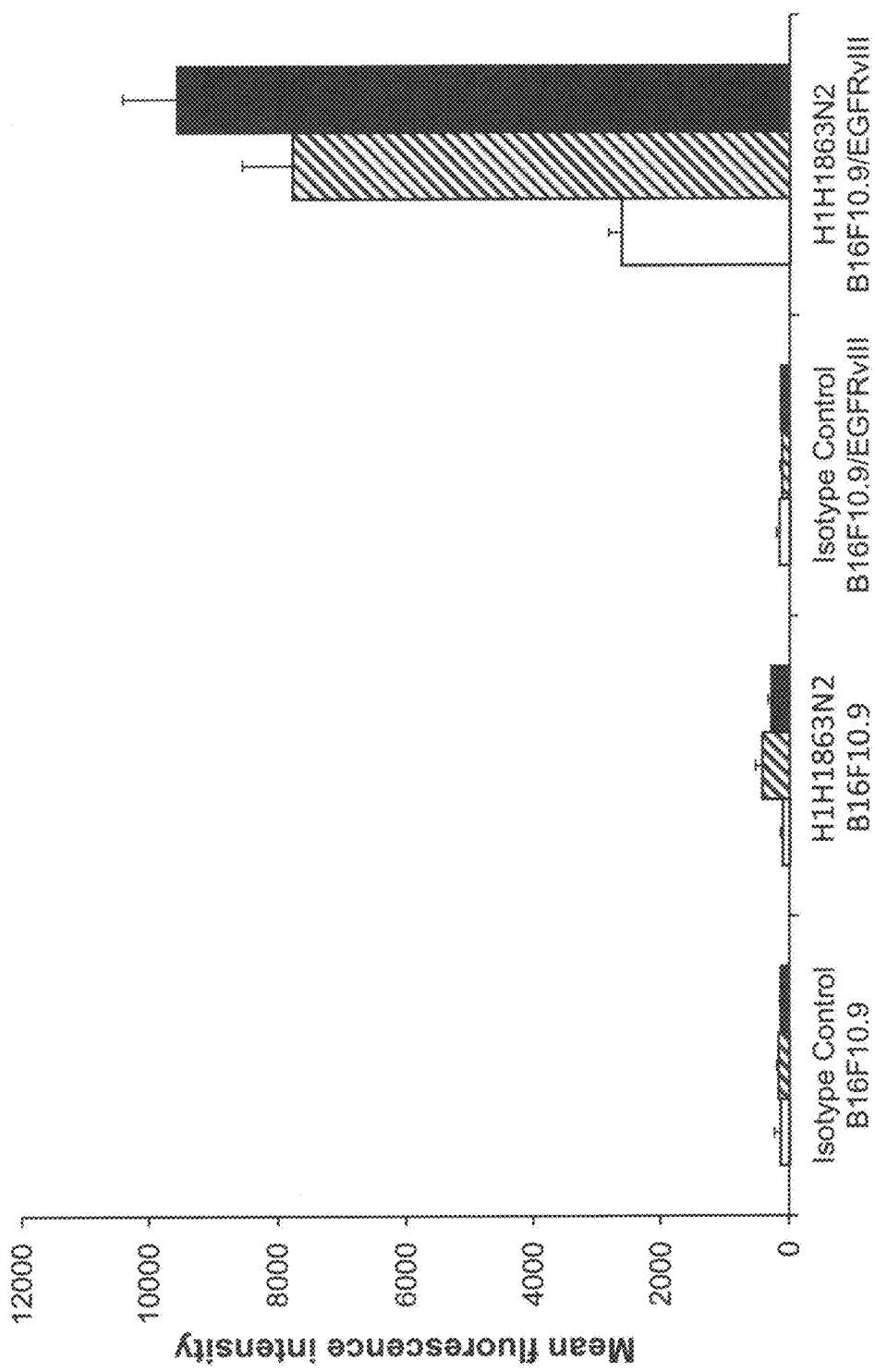

Example 10: Binding of Anti-EGFRvIII Antibody to B16F10.9/EGFRvIII Tumor Xenograft SCID mice were implanted with fifty thousand of murine melanoma cells B16F10.9 or B16F10.9 over-expressing EGFRvIII (B16F10.9/EGFRvIII). B16F10.9/EGFRvIII cells were prepared as described for HEK293/EGFRvIII cells in Example 7. B16F10.9 cells expressing ~1.5×10$^5$ copies of EGFRvIII per cell are used for this experiment. Tumors were allowed to grow for approximately 14 days, until a median size of 200-300 mm$^3$ was obtained. Mice were then injected with H1H1863N2(Fuc−) or isotype control via their tail vein. At 10 minutes, 4 hours and 24 hours post injection of antibody, mice were sacrificed and tumors were removed and placed into PBS. Tumors were immediately dissociated and stained with an allophycocyanin conjugated anti-human Fc (hFc-APC) antibody. Stained cells were washed 3× with flow PBS (1×PBS, 2% fetal calf serum, 0.1% sodium azide), fixed and permealized using standard methods. Flow cytometry was used to detect cell surface-bound H1H1863N2(Fuc−) and analysis was performed using FlowJo software (Tree Star, Inc.). The results are shown in Table 13 and FIG. 4a. To detect both cell surface-bound and intracellularly-bound antibodies, cells were stained a second time using the same anti-human Fc (hFc-APC) antibody following the fixation and permeabilization steps. This allowed for intracellular antibody to be detected. The results are shown in Table 14 and FIG. 4b. All samples were collected on an ACCURI® C6 FLOW CYTOMETER® and the mean fluorescence intensity (MFI) determined. MFI for each sample was reported after subtracting the MFI of the unstained control. MFI values are the average of two biological replicates (N=2)±the standard error of the mean (SEM). * N=1 for this time point.

TABLE 13

| | MFI ± SEM (B16F10.9/EGFRvIII) - Surface Staining | | | |
| --- | --- | --- | --- | --- |
| | B16F10.9 | | B16F10.9/EGFRvIII | |
| Time Post-Injection | Isotype Control | H1H1863N2 (Fuc−) | Isotype Control | H1H1863N2 (Fuc−) |
| 10 minutes | 74 ± 67 | 56 ± 2 | 128 ± 49 | 2003 ± 216 |
| 4 hour | 80 ± 15 | 195 ± 52 | 54 ± 21 | 4224 ± 610 |
| 24 hour | 79 ± 21 | 155 ± 42 | 72* | 5692 ± 595 |

TABLE 14

| | MFI ± SEM (B16F10.9/EGFRvIII) - Surface & Internal Staining | | | |
|---|---|---|---|---|
| | B16F10.9 | | B16F10.9/EGFRvIII | |
| Time Post-Injection | Isotype Control | H1H1863N2 (Fuc−) | Isotype Control | H1H1863N2 (Fuc−) |
| 10 minutes | 132 ± 92 | 117 ± 18 | 155 ± 44 | 2627 ± 192 |
| 4 hour | 165 ± 22 | 422 ± 106 | 120 ± 22 | 7785 ± 782 |
| 24 hour | 135 ± 11 | 281 ± 51 | 132* | 9578 ± 852 |

H1H1863N2(Fuc−) bound efficiently to the surface of B16F10.9 cells expressing EGFRvIII in a time-dependent manner, while the binding of isotype control was minimal. The increase in total binding (i.e., cell surface bound plus internally bound) of H1H1863N2(Fuc−), compared to its binding to cell surface only, indicated that the cell surface-bound antibodies were effectively internalized by B16F10.0 cells.

Example 11: Pharmacokinetics of Anti-EGFRvIII Antibodies in Mice

To determine the in vivo selectivity of anti-EGFRvIII antibodies a pharmacokinetic study using wild-type mice ("WT mice") naturally expressing mouse EGFR, and humanized EGFR mice ("hEGFR mice") expressing human EGFR, was carried out. Mice were from cross-bred strains with a background containing C57BL6 (75%) and 129Sv (25%). Cohorts contained 5 each of either WT or hEGFR mice. All antibodies were administered subcutaneously at a dose of 0.2 mg/kg. Bleeds were collected at 0 hour, 6 hours, 1 day, 2 days, 3 days, 4 days, 7 days, 10 days, 14 days, 21 days, and 30 days after the administration. Serum levels of human antibodies were determined by sandwich ELISA. Briefly, a goat polyclonal anti-human IgG (Fc-specific) antibody (Jackson ImmunoResearch) was coated in 96-well plates at a concentration of one μg/ml and incubated overnight at 4° C. After the plates were blocked with BSA, serum samples in six-dose serial dilutions and reference standards of the respective antibodies in twelve-dose serial dilutions were added to the plate and incubated for one hour at room temperature. After washing to remove unbound antibody, captured human antibodies were detected using the same goat polyclonal anti-human IgG (Fc-specific) antibody conjugated with horseradish peroxidase (HRP) (Jackson ImmunoResearch) and developed by standard colorimetric tetramethylbenzidine (TMB) substrate according to the manufacturer's recommendation. Absorbances at 450 nm were recorded on a plate reader and the concentration of hIgG in serum samples were calculated using the reference standard curve generated in the sample plate. Mouse anti-human antibodies (MAHA) were measured using standard methods and were generally low.

FIGS. 5a-5d show the antibody concentration vs. time plots for the four tested antibodies. Control IV ("Mab C225") is known to bind human EGFR but not its mouse homologue. As expected, this antibody displayed fast clearance in hEGFR mice and slow clearance (i.e., no target-mediated clearance) in WT mice (FIG. 5a). Control I ("Mab 13.1.2") is known to bind the EGFRvIII junctional peptide "LEEKKGNYVVTDH" that is not present in human or mouse EGFR. The antibody does not bind human or mouse EGFR in vivo. As expected, this antibody displayed identical slow pharmacokinetic clearance rates in both types of mice (FIG. 5b) and no target-mediated clearance was observed. Control III antibody ("Mab hu806") showed increased clearance in hEGFR mice relative to WT mice (FIG. 5c). This finding is consistent with its ability to bind hEGFR in vitro as determined by Biacore (see Example 3, Table 4) and FACS (Example 7, Table 9). FIG. 5d shows the clearance of H1H1863N2(Fuc+). This antibody, similar to control I, displayed identical slow clearance rates in both types of mice. Thus, H1H1863N2 does not bind human or mouse EGFR in vivo.

Example 12: An Anti-EGFRvIII Antibody-Drug Conjugate Inhibits Tumor Growth in In Vivo EGFRvIII-Positive Breast Cancer Allograft Models In this Example, two different antibody-drug conjugates of the exemplary anti-EGFRvIII antibody H1H1863N2 were tested for their ability to inhibit tumor growth in vivo. A first ADC was produced by conjugating H1H1863N2 to the maytansinoid toxin DM1 via a non-cleavable MCC linker (see, e.g., U.S. Pat. No. 5,208,020 and US application 2010/0129314) to produce "H1H1863N2-MCC-DM1." A second ADC was produced by conjugating H1H1863N2 to a modified version of DM1 attached to a novel cleavable linker, referred to as "M0026" (also known as "compound 7" in WO2014/145090, the disclosure of which is incorporated by reference herein in its entirety), to yield "H1H1863N2-M0026." When tested for cytotoxicity in vitro against MMT/EGFRvIII cells, H1H1863N2-MCC-DM1 exhibited an $IC_{50}$ of 12 nM whereas H1H1863N2-7 exhibited an $IC_{50}$ of 0.8 nM based on drug equivalents.

To compare the in vivo efficacy of the anti-EGFRvIII antibodies conjugated to DM1 and M0026, studies were performed in immunocompromised mice bearing EGFRvIII positive breast cancer allografts.

Briefly, tumor allografts were established by subcutaneous implantation of $0.5 \times 10^6$ MMT/EGFRvIII cells into the left flank of female CB17 SCID mice (Taconic, Hudson, N.Y.). Once tumors had reached an average volume of 140 mm³ (~Day 8), mice were randomized into groups of seven, and dosed with anti-EGFRvIII ADCs using either the MCC-DM1 or M0026 linker-drug format. Control reagents, including non-binding ADCs using either the MCC-DM1 or M0026 linker-drug format, and PBS vehicle were also assessed. ADCs were dosed at 1 and 5 mg/kg three times over one week and thereafter monitored until an average tumor size of approximately 2000 mm³ was attained in the group administered with vehicle alone. At this point the Tumor Growth Inhibition was calculated as described below.

Average tumor size relative to the vehicle treated group was calculated as follows: tumors were measured with calipers twice a week until the average size of the vehicle group reached 1000 mm³; tumor size was calculated using the formula (length×width²)/2. Tumor growth inhibition was calculated according to the following formula: $(1-((T_{final}-T_{initial})/(C_{final}-C_{initial})))*100$, where T (treated group) and C (control group) represent the mean tumor mass on the day the vehicle group reached 1000 mm³. Results are summarized in Table 15.

TABLE 15

| Treatment Group | Final Tumor size at Day 8 mm³ (mean ± SD) | Average Tumor Growth Inhibition (%) |
|---|---|---|
| PBS Vehicle | 2253 ± 217 | 0 |
| Control-MCC-DM1 1 mg/kg | 2827 ± 278 | −27 |
| Control-MCC-DM1 5 mg/kg | 2402 ± 256 | −7 |

TABLE 15-continued

| Treatment Group | Final Tumor size at Day 8 mm³ (mean ± SD) | Average Tumor Growth Inhibition (%) |
|---|---|---|
| Control-M0026 1 mg/kg | 2729 ± 470 | −22 |
| Control-M0026 5 mg/kg | 2787 ± 503 | −25 |
| H1H1863N2-MCC-DM1 1 mg/kg | 931 ± 292 | 62 |
| H1H1863N2-MCC-DM1 5 mg/kg | 471 ± 227 | 84 |
| H1H1863N2-M0026 1 mg/kg | 679 ± 265 | 74 |
| H1H1863N2-M0026 5 mg/kg | 96 ± 34 | 102 |

As summarized in Table 15, the greatest tumor inhibition was observed in mice dosed with 5 mg/kg H1H1863N2-M0026, where regression of the initial tumor was observed. The tumor growth inhibition of 102% resulting from treatment with 5 mg/kg H1H1863N2-M0026 was significantly greater relative to that observed following treatment of tumor with 5 mg/kg H1H1862N2-MCC-DM1 (83%). The superiority of the tumor growth inhibition induced by H1H1863N2-M0026 compared to H1H1863N2-mcc-DM1 was maintained at the 1 mg/kg dose as well. No anti-tumor effect was observed in groups treated with Control ADC using MCC-DM1 or M0026.

This Example therefore shows that anti-EGFRvIII antibodies of the present invention, when administered in the form of antibody-drug conjugates, are highly potent at inhibiting tumor growth. The present Example additionally supports a role for the ADCs of the invention to actually promote tumor regression, especially in the context of anti-EGFRvIII antibodies of the invention (e.g., H1H1863N2) conjugated to the novel linker/drug molecule M0026.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

Example 13: Anti-EGFRvIII-DM1 Antibodies Show Specificity for EGFRvIII-Expressing Cells and Demonstrate Potent Cell Killing Activity In this Example, the ability of anti-human EGFRvIII antibodies conjugated to maytansine toxin DM1 to reduce cell viability was determined using in vitro cell based assays.

Full length human EGFRvIII (SEQ ID NO:147) or wild-type human EGFR (SEQ ID NO:146) was stably introduced into HEK293 (293/hEGFRvIII, 293/hEGFRwt), U251 (U251/hEGFRvIII) and MMT 060562 (MMT/hEGFRvIII) cell lines. All cells were generated via lipofectamine 2000 based methodologies and were cultured in complete growth media in the presence of G418.

Cell surface expression of EGFR wt or EGFRvIII was measured via FACS analysis. Briefly, 1×10⁶ cells were incubated with 10 μg/ml of anti-EGFRvIII antibody H1H1863N2, an anti-EGFRwt control mAb (Control IV) or isotype control for 30 min. on ice in antibody dilution buffer. Following two washes with antibody dilution buffer, cells were incubated with 10 μg/ml of PE conjugated anti-human secondary antibody for 30 min on ice. After two additional washes, samples were run on an Accuri C6 (BD) or Hypercyt (Intellicyt) cytometer and analyzed data analyzed using FlowJo software. Results are summarized in Table 16. n.d.=not determined.

TABLE 16

Cell Surface Expression in EGFRwt and EGFRvIII Engineered Cell Lines

| | FACS Binding (MFI Fold Above Isotype Control) | | | | |
|---|---|---|---|---|---|
| Cell Line | Un-stained | H1H1863N2 (anti-EGFRvIII) | Control IV (Anti-EGFRwt) | Secondary Alone | Isotype Control |
| HEK293 | 1X | 1X | 49x | 1X | 1X |
| HEK293/hEGFRwt | 1X | n.d. | 332x | 1X | 1X |
| HEK293/hEGFRvIII | 1X | 264X | n.d. | 1X | 1X |
| U251 | 1X | 1X | n.d. | 1X | 1X |
| U251/hEGFRvIII | 1X | 13X | n.d. | 1X | 1X |
| MMT/ | 1X | 1X | n.d. | 1X | 1X |
| MMT/hEGFRvIII | 1X | 280X | n.d. | 1X | 1X |

These results show that EGFRvIII surface expression was comparable in the HEK293/hEGFRvIII and MMT/hEGFRvIII cells lines, whereas U251/EGFRvIII expression levels were approximately 20-fold lower than in the HEK293/hEGFRvIII and MMT/hEGFRvIII cell systems. EGFRvIII binding via H1H1863N2 was not detectable in the parental cell lines. In contrast, the anti-EGFRwt control antibody (Control IV) bound to HEK293 parental cells at 49-fold above the isotype control. Stable incorporation of an EGFRwt expression vector into HEK293 cells increased expression to 332 fold above background and was comparable to EGFRvIII expression in HEK293/hEGFRvIII and MMT/hEGFRvIII cells.

The selective binding of anti-EGFRvIII antibody H1H1863N2 to EGFRvIII was assessed via FACS using HEK293 parental, HEK293/hEGFRwt, HEK293/hEGFRvIII, and A431 cell lines. Results are shown in Table 17.

TABLE 17

Binding Specificity of anti-EGFRvIII Antibody to EGFRvIII-Expressing Cell Lines

| | FACS Binding (MFI Fold Above Isotype Control) | | | |
|---|---|---|---|---|
| mAb | HEK293 | HEK293/EGFRwt | HEK293/EGFRvIII | A431 |
| Control IV (Anti-EGFRwt) | 83 | 251 | 855 | 621 |
| H1H1863N2 (anti-EGFRvIII) | 1 | 3 | 662 | 13 |
| Isotype Control | 1 | 1 | 1 | 1 |
| Secondary Ab Alone | 1 | 1 | 1 | 1 |
| Unstained Cells | 1 | 1 | 1 | 1 |

As shown in Table 17, both H1H1863N2 and anti-EGFRwt control antibody (Control IV) exhibited strong binding (>650 fold above background) to HEK293/EGFRvIII cells relative to an isotype control. In contrast, H1H1863N2 bound weakly to the wt-EGFR HEK293 cell line (3-fold above background) and endogenously expressing EGFR cell line A431 (13-fold above control). Anti-EGFR-wt Control Antibody bound strongly to the wt EGFR-expressing cells, confirming the selectivity of H1H1863N2 for EGFRvIII over wild-type EGFR.

Next, the ability of anti-human EGFRvIII antibodies conjugated to the maytansine toxin DM1 to reduce cell viability was determined using in vitro cell based assays. Cells were seeded in PDL-coated 96 well plates at 250-2000 cells per well in complete growth media and allowed to grow overnight. For cell viability curves, ADCs or free drug (DM1-SMe) was added to cells at final concentrations ranging from 500 nM to 5 µM and incubated for 3 days. Cells were incubated with CCK8 (Dojindo) for the final 1-3 h and the absorbance at 450 nm ($OD_{450}$) was determined on the Flexstation3 (Molecular Devices). Background OD450 levels from digitonin (40 nM) treated cells was subtracted from all wells and viability is expressed as a percentage of the untreated controls. IC50 values were determined from a four-parameter logistic equation over a 10-point response curve (Graph Pad Prism). Results are shown in Tables 18A and 18B. $IC_{50}$ values are in nM and are normalized for the particular drug/antibody ratio (DAR).

TABLE 18A

Cell Kill Potency of Anti-EGFRvIII-DM1 Antibody-Drug Conjugates

| Cell Line ADC | HEK293 | | HEK293/ hEGFRvIII | | HEK293/ hEGFRwt | | U251 | |
|---|---|---|---|---|---|---|---|---|
| | $IC_{50}$ (nM) | % Kill | $IC_{50}$ (nM) | % Kill | $IC_{50}$ (nM) | % Kill | $IC_{50}$ (nM) | % Kill |
| H1H1863N2-MCC-DM1 | >100 | 90 | 1 | 97 | >100 | 91 | 48 | 77 |
| Anti-EGFRwt-MCC-DM1 | 76 | 94 | 0.2 | 97 | ~1.0 | 94 | ND | ND |
| DM1-SMe | 0.31 | 97 | 0.6 | 99 | 0.57 | 95 | 1.8 | 81 |
| Isotype Control-MCC-DM1 | >100 | 92 | >100 | 96 | >100 | 91 | 40 | 77 |

TABLE 18B

Cell Kill Potency of Anti-EGFRvIII-DM1 Antibody-Drug Conjugates

| Cell Line ADC | U251/hEGFRvIII | | MMT | | MMT/hEGFRvIII | |
|---|---|---|---|---|---|---|
| | $IC_{50}$ (nM) | % Kill | $IC_{50}$ (nM) | % Kill | $IC_{50}$ (nM) | % Kill |
| H1H1863N2-MCC-DM1 | 4 | 78 | >150 | 40 | 3 | 100 |
| Anti-EGFRwt-MCC-DM1 | ND | ND | ND | ND | ND | ND |
| DM1-SMe | 1.2 | 83 | 0.6 | 96 | 0.7 | 100 |
| Isotype Control-MCC-DM1 | 35 | 76 | >150 | 66 | NK | 72 |

As shown in Tables 18A and 18B, H1H1863N2-MCC-DM1 reduced the viability of HEK293/hEGFRvIII, U251/hEGFRvIII, and MMT/hEGFRvIII cell lines with IC50s ranging from 1.0 to 4.0 nM. In contrast, an isotype control conjugated to DM1 reduced the viability of 293/EGFRvIII and MMT/hEGFRvIII cells with IC50s greater than 100 nM and U251/hEGFRvIII cells with an IC50 of 35 nM. H1H1863N2-MCC-DM1 had no impact on HEK293 cells expressing wild-type EGFR (293/hEGFRwt) or on the control parental cell lines suggesting specificity for EGFRvIII expressing cells.

Thus, this Example demonstrates that the EGFRvIII antibody H1H1863N2 has specificity for EGFRvIII-expressing cell lines and demonstrates specific cell killing ability when conjugated to the DM1 toxin.

Example 14: Improved Cell Killing Potency is Achieved when an EGFRvIII Conformational-Binding Antibody-Drug Conjugate is Dosed in Combination with an EGFRvIII Junctional Peptide-Binding Antibody-Drug Conjugate In this example, the ability to enhance cell killing by co-administering two different types of anti-EGFRvIII antibody-drug conjugates was determined. For this Example the combinations tested consisted of two different anti-EGFRvIII antibodies: (1) an anti-EGFRvIII specific antibody that does not recognize the EGFRvIII junctional peptide ADC (referred to herein as a "conformational binder"); and (2) an anti-EGFRvIII specific antibody that does recognize the EGFRvIII junctional peptide (referred to herein as a "peptide binder"). As demonstrated in Example 6, the anti-EGFRvIII antibody H1H1863N2 does not bind to the EGFRvIII junctional peptide or residues 311-326 of human EGFR and is therefore regarded as a "conformational binder".

Cross Competition In Vitro

First, the ability of H1H1863N2 to cross compete with an antibody that binds the EGFRvIII junctional peptide was determined via a binding competition assay. The junctional peptide binding anti-EGFRvIII antibody used in this example was Control V.

Cross competition was determined using a real time, label-free bio-layer interferometry (BLI) assay on an Octet HTX biosensor (ForteBio Corp., A Division of Pall Life Sciences). The entire experiment was performed at 25° C. in buffer comprised of 0.01M HEPES pH7.4, 0.15M NaCl, 3 mM EDTA, 0.05% v/v Surfactant P20, 1.0 mg/mL BSA (Octet HBST buffer) with the plate shaking at a speed of 1000 rpm. To assess whether two antibodies cross-competed for binding on recombinant human EGFRvIII (hEGFRvIII.mmh; SEQ ID:152), approximately ~0.35 nm of hEGFRvIII.mmh was captured onto anti-penta-His coated Octet biosensors. The antigen-captured biosensors were then saturated with the first anti-EGFRvIII monoclonal antibody (subsequently referred to as mAb-1) by immersion into wells containing a 50 µg/mL solution of mAb-1 for 5 minutes. The biosensors were then subsequently submerged into wells containing a 50 µg/mL solution of a second anti-EGFRvIII monoclonal antibody (subsequently referred to as mAb-2) for 3 minutes. All the biosensors were washed in Octet HBST buffer in between each step of the experiment. The real-time binding response was monitored during the course of the experiment and the binding response at the end of every step was recorded. The response of mAb-2 binding to hEGFRvIII pre-complexed with mAb-1 was compared and competitive/non-competitive behavior of different anti-EGFRvIII monoclonal antibodies was determined.

Using this experimental cross-competition format, H1H1863N2 did not exhibit cross competition with the EGFRvIII junctional peptide binder tested, nor did it cross compete for binding to EGFRvIII with Control II or Control IV. The results of this cross competition assay therefore indicate that H1H1863N2 has a distinct binding epitope to that of the EGFRvIII junctional peptide binder, as well as Controls II and IV.

Cell Killing Activity of Individual Anti-EGFRvIII Antibody-Drug Conjugates

Next, the ability of H1H1863N2-MCC-DM1 and an anti-EGFRvIII peptide-binding ADC to reduce cell viability when administered in combination was assessed. The ability of Control V to induce cell kill when conjugated to SMCC-DM1 (i.e., Control V-MCC-DM1) was determined using an in vitro cell based assay as described in Example 13. Results are summarized in Table 19.

TABLE 19

Cell Kill Potency of Anti-EGFRvIII-DM1 Antibody-Drug Conjugates

| Cell Line | HEK293 | | HEK293/ hEGFRvIII (high) | | MMT | | MMT/ hEGFRvIII (high) | |
|---|---|---|---|---|---|---|---|---|
| ADC | $IC_{50}$ | % Kill | $IC_{50}$ | % Kill | $IC_{50}$ | % Kill | $IC_{50}$ | % Kill |
| DM1-SMe (free DM1) | 0.19 | 98 | 0.25 | 99 | 0.15 | 100 | 0.18 | 99 |
| Isotype Ctrl - MCC-DM1 | 200 | 91 | 150 | 92 | 110 | 68 | 250 | 72 |
| H1H1863N2-MCC-DM1 | 80 | 97 | 0.37 | 99 | 200 | 95 | 3.25 | 97 |
| Control V-MCC-DM1 | 90 | 95 | 0.25 | 100 | 200 | 89 | 0.35 | 97 |

As summarized in Table 19, anti-EGFRvIII ADCs reduced cell viability of various EGFRvIII overexpressing cell lines with $IC_{50}$ values ranging from 0.25 nM to 3.25 nM.

Cell Killing Activity of Pairwise Combinations of Anti-EGFRvIII Antibody-Drug Conjugates Next, the cell killing potency of H1H1863N2-MCC-DM1 paired with the anti-EGFRvIII peptide-binding ADC was tested on EGFRvIII over-expressing cell lines in a 1:1 ratio. Results are shown in Table 20.

TABLE 20

Cell Kill Potency of Pairwise Combinations of Anti-EGFRvIII-DM1 ADCs

| | | HEK293 | | HEK293/ hEGFRvIII | | MMT | | MMT/ hEGFRvIII | |
|---|---|---|---|---|---|---|---|---|---|
| Cell Line: | | $IC_{50}$ | | $IC_{50}$ | | $IC_{50}$ | | $IC_{50}$ | |
| ADC 1 | ADC 2 | (nM) | % Kill | (nM) | % Kill | (nM) | % Kill | (nM) | % Kill |
| H1H1863N2-MCC-DM1 | None | 250 | 87 | 1.52 | 95 | 250 | 59 | 11.1 | 98 |
| Control V-MCC-DM1 | None | 100 | 85 | 0.14 | 98 | 100 | 67 | 0.7 | 95 |
| H1H1863N2-MCC-DM1 | Control V-MCC-DM1 | 100 | 91 | 0.19 | 99 | 200 | 98 | 0.58 | 100 |
| DM1-SMe (Free DM1) | None | 0.21 | 96 | 0.28 | 97 | 0.19 | 100 | 0.19 | 100 |
| Isotype Ctrl-MCC-DM1 | None | 200 | 93 | 95 | 93 | 150 | 32 | 100 | 36 |

As summarized in Table 20, the combination of H1H1863N2-MCC-DM1 (a conformational epitope binder) and the Control V-MCC-DM1 (a junctional peptide binder) resulted in cell killing potency that was at least equivalent to, or in certain instances, enhanced as compared with the single-ADC treatments. The lack of interference between the two types of antibodies suggests the effective use of two non-competing antibodies with different cytotoxins, or different classes of cytotoxins having distinct mechanisms of action.

In summary, this example demonstrates that H1H1863N2 does not cross-compete with the control EGFRvIII peptide binding antibody. This unique epitope allows for its combination with EGFRvIII peptide-binding ADCs to improve cell killing potency. This novel combination of EGFRvIII ADCs may allow for better therapeutic efficacy.

What is claimed is:

1. An isolated nucleic acid molecule comprising a nucleic acid sequence encoding a heavy chain immunoglobulin variable domain region (HCVR) of an antibody that binds human EGFRvIII, wherein the HCVR comprises a heavy chain CDR1 (HCDR1) comprising SEQ ID NO: 36, a heavy chain CDR2 (HCDR2) comprising SEQ ID NO: 38, and a heavy chain CDR3 (HCDR3) comprising SEQ ID NO: 40.

2. The nucleic acid molecule of claim 1, wherein the HCVR comprises the amino acid sequence of SEQ ID NO: 34.

3. The nucleic acid molecule of claim 1, wherein the nucleic acid molecule comprises the nucleotide sequence of SEQ ID NO: 33.

4. An isolated nucleic acid molecule comprising a nucleic acid sequence encoding an HCVR of an antibody that binds human EGFRvIII, wherein the nucleic acid molecule comprises (i) the nucleotide sequence as set forth in SEQ ID NO: 33 or (ii) a nucleotide sequence with a substantially identical sequence having at least 95% sequence identity to SEQ ID NO: 33 and comprising within said nucleotide sequence the nucleotide sequences as set forth in SEQ ID NO: 35, SEQ ID NO: 37, and SEQ ID NO: 39.

5. An isolated nucleic acid molecule comprising a nucleic acid sequence encoding a light chain immunoglobulin variable region (LCVR) of an antibody that binds human EGFRvIII, wherein the LCVR comprises a light chain CDR1 (LCDR1) comprising SEQ ID NO: 44, a light chain CDR2 (LCDR2) comprising SEQ ID NO: 46, and a light chain CDR3 (LCDR3) comprising SEQ ID NO: 48.

6. The nucleic acid molecule of claim 5, wherein the LCVR comprises SEQ ID NO: 42.

7. The nucleic acid molecule of claim 5, wherein the nucleic acid molecule comprises the nucleotide sequence of SEQ ID NO: 41.

8. An isolated nucleic acid molecule comprising a nucleic acid sequence encoding an LCVR of an antibody that binds human EGFRvIII, wherein the nucleic acid molecule comprises: (i) the nucleotide sequence as set forth in SEQ ID NO: 41 or (ii) a nucleotide sequence with a substantially identical sequence having at least 95% sequence identity to SEQ ID NO: 41; and comprising within said nucleotide sequence the nucleotide sequences as set forth in SEQ ID NO: 43, SEQ ID NO: 45, and SEQ ID NO: 47.

9. An expression vector comprising:
   (a) a nucleic acid molecule comprising a nucleic acid sequence encoding a heavy chain immunoglobulin variable domain region (HCVR) of an antibody that binds human EGFRvIII, wherein the HCVR comprises a heavy chain CDR1 (HCDR1) comprising SEQ ID NO: 36, a heavy chain CDR2 (HCDR2) comprising SEQ ID NO: 38, and a heavy chain CDR3 (HCDR3) comprising SEQ ID NO: 40; or
   (b) a nucleic acid molecule comprising a nucleic acid sequence encoding a light chain immunoglobulin variable domain region (LCVR) of an antibody that binds human EGFRvIII, wherein the LCVR comprises a light chain CDR1 (LCDR1) comprising SEQ ID NO: 44, a light chain CDR2 (LCDR2) comprising SEQ ID NO: 46, and a light chain CDR3 (LCDR3) comprising SEQ ID NO: 48.

10. An isolated host cell comprising an expression vector of claim claim 9.

11. An isolated nucleic acid molecule encoding an HCVR or an LCVR of an anti-EGFRvIII antibody or antigen-binding fragment thereof, wherein the HCVR comprises a heavy chain CDR1 (HCDR1) comprising SEQ ID NO: 36, a heavy chain CDR2 (HCDR2) comprising SEQ ID NO: 38, and a heavy chain CDR3 (HCDR3) comprising SEQ ID NO: 40, and the LCVR comprises a light chain CDR1 (LCDR1) comprising SEQ ID NO: 44, a light chain CDR2 (LCDR2) comprising SEQ ID NO: 46, and a light chain CDR3 (LCDR3) comprising SEQ ID NO: 48.

* * * * *